(12) United States Patent
Bennett et al.

(10) Patent No.: US 7,976,483 B2
(45) Date of Patent: *Jul. 12, 2011

(54) ULTRASOUND ASSEMBLY WITH INCREASED EFFICACY

(75) Inventors: Frederick J. Bennett, Issaquah, WA (US); James E. Rodriguey, Seattle, WA (US)

(73) Assignee: Ekos Corporation, Bothell, WA (US)

( * ) Notice: Subject to any disclaimer, the term of this patent is extended or adjusted under 35 U.S.C. 154(b) by 1585 days.

This patent is subject to a terminal disclaimer.

(21) Appl. No.: 10/735,588

(22) Filed: Dec. 12, 2003

(65) Prior Publication Data
US 2005/0010112 A1 Jan. 13, 2005

Related U.S. Application Data

(63) Continuation of application No. 09/374,642, filed on Aug. 16, 1999, now Pat. No. 6,676,626, which is a continuation-in-part of application No. 09/375,162, filed on Aug. 16, 1999, now Pat. No. 6,582,392, and a continuation-in-part of application No. 09/129,980, filed on Aug. 5, 1998, now Pat. No. 6,210,356, and a continuation-in-part of application No. 09/107,078, filed on Jun. 29, 1998, now Pat. No. 6,723,063, and a continuation-in-part of application No. 09/071,285, filed on May 1, 1998, now Pat. No. 6,001,069.

(60) Provisional application No. 60/045,268, filed on May 1, 1997.

(51) Int. Cl.
*A61B 17/20* (2006.01)

(52) U.S. Cl. ........... 601/2; 600/439; 600/446; 600/459; 600/462; 600/467; 600/469; 600/471; 600/472; 601/3; 601/4; 604/22; 604/500; 604/17

(58) Field of Classification Search .................. 600/437, 600/439, 471, 446, 459, 465, 462, 469, 467, 600/472; 601/2; 604/22, 500
See application file for complete search history.

(56) References Cited

U.S. PATENT DOCUMENTS
2,961,382 A 11/1960 Singher et al.
(Continued)

FOREIGN PATENT DOCUMENTS
DE 39 19 592 A1 2/1990
(Continued)

OTHER PUBLICATIONS
Hynynen et al.; "Small Cylindrical Ultrasound Sources for Induction of Hyperthermia Via Body Cavities or Interstitial Implants"; Arizona Cancer Center and DEuropeartment of Radiation Oncology, University of Arizona Health Sciences Center; vol. 9, No. 2; pp. 263-274; 1993.
(Continued)

*Primary Examiner* — Tse Chen
*Assistant Examiner* — Baisakhi Roy
(74) *Attorney, Agent, or Firm* — Knobbe, Martens, Olson & Bear, LLP

(57) ABSTRACT

A catheter system is disclosed. The catheter system includes a catheter body having an external surface and an ultrasound transducer having a side between a first end and a second end. A first medium is positioned adjacent to the first end of the ultrasound transducer and a second medium is positioned adjacent to the external side of the ultrasound transducer. The second medium is harder than the first medium to encourage flexibility of the catheter body adjacent to the first end of the ultrasound transducer and efficient transmission of ultrasound energy from the external side of the ultrasound transducer.

43 Claims, 42 Drawing Sheets

U.S. PATENT DOCUMENTS

| | | | |
|---|---|---|---|
| 3,433,226 A | 3/1969 | Boyd | |
| 3,565,062 A | 2/1971 | Kuris | |
| 4,027,659 A | 6/1977 | Slingluff | |
| 4,040,414 A | 8/1977 | Suroff | |
| 4,319,580 A | 3/1982 | Colley et al. | |
| 4,354,502 A | 10/1982 | Colley et al. | |
| 4,466,442 A | 8/1984 | Hilmann et al. | |
| 4,512,762 A | 4/1985 | Spears | |
| 4,531,943 A | 7/1985 | Van Tassel et al. | |
| 4,549,533 A | 10/1985 | Cain et al. | |
| 4,573,470 A | 3/1986 | Samson et al. | |
| 4,582,067 A | 4/1986 | Silverstein et al. | |
| 4,657,543 A | 4/1987 | Langer et al. | |
| 4,657,756 A | 4/1987 | Rasor et al. | |
| 4,692,139 A | 9/1987 | Stiles | |
| 4,697,595 A | 10/1987 | Breyer et al. | |
| 4,698,058 A | 10/1987 | Greenfeld et al. | |
| 4,699,150 A * | 10/1987 | Kawabuchi et al. | 600/446 |
| 4,710,192 A | 12/1987 | Liotta et al. | |
| 4,729,384 A | 3/1988 | Bazenet | |
| 4,750,902 A | 6/1988 | Wuchinich et al. | |
| 4,762,915 A | 8/1988 | Kung et al. | |
| 4,767,402 A | 8/1988 | Kost et al. | |
| 4,769,017 A | 9/1988 | Fath et al. | |
| 4,772,594 A | 9/1988 | Hashimoto et al. | |
| 4,774,958 A | 10/1988 | Feinstein | |
| 4,780,212 A | 10/1988 | Kost et al. | |
| 4,781,677 A | 11/1988 | Wilcox | |
| 4,795,439 A | 1/1989 | Guest | |
| 4,797,285 A | 1/1989 | Barenholz et al. | |
| 4,808,153 A | 2/1989 | Parisi | |
| 4,821,740 A | 4/1989 | Tachibana et al. | |
| 4,844,882 A | 7/1989 | Widder et al. | |
| 4,870,953 A | 10/1989 | Don Micheal et al. | |
| 4,877,031 A | 10/1989 | Conway et al. | |
| 4,900,540 A | 2/1990 | Ryan et al. | |
| 4,917,088 A | 4/1990 | Crittendon | |
| 4,917,102 A | 4/1990 | Miller et al. | |
| 4,920,954 A | 5/1990 | Alliger et al. | |
| 4,924,863 A | 5/1990 | Sterzer | |
| 4,936,281 A | 6/1990 | Stasz | |
| 4,947,852 A * | 8/1990 | Nassi et al. | 600/465 |
| 4,948,587 A | 8/1990 | Kost et al. | |
| 4,953,565 A | 9/1990 | Tachibana et al. | |
| 4,955,863 A | 9/1990 | Walker et al. | |
| 4,969,470 A | 11/1990 | Mohl et al. | |
| 4,971,991 A | 11/1990 | Umemura et al. | |
| 4,992,257 A | 2/1991 | Bonnett et al. | |
| 5,007,898 A | 4/1991 | Rosenbluth et al. | |
| 5,021,044 A | 6/1991 | Shakawy | |
| 5,040,537 A | 8/1991 | Katakura | |
| 5,053,044 A | 10/1991 | Mueller et al. | |
| 5,069,664 A | 12/1991 | Guess et al. | |
| 5,081,993 A | 1/1992 | Kitney | |
| 5,085,662 A | 2/1992 | Willard | |
| 5,117,831 A | 6/1992 | Jang et al. | |
| 5,121,749 A | 6/1992 | Nassi et al. | |
| 5,125,410 A | 6/1992 | Misono et al. | |
| 5,149,319 A | 9/1992 | Unger | |
| 5,156,050 A | 10/1992 | Schmid et al. | |
| 5,158,071 A | 10/1992 | Umemura et al. | |
| 5,163,421 A | 11/1992 | Bernstein et al. | |
| 5,181,920 A | 1/1993 | Mueller et al. | |
| 5,190,766 A | 3/1993 | Ishihara | |
| 5,197,946 A | 3/1993 | Tachibana | |
| 5,207,214 A | 5/1993 | Romano | |
| 5,209,720 A | 5/1993 | Unger | |
| 5,215,680 A | 6/1993 | D'Arrigo | |
| 5,216,130 A | 6/1993 | Line et al. | |
| 5,250,034 A | 10/1993 | Appling et al. | |
| 5,267,954 A | 12/1993 | Nita | |
| 5,267,985 A | 12/1993 | Shimada et al. | |
| 5,269,291 A | 12/1993 | Carter | |
| 5,269,297 A | 12/1993 | Weng et al. | |
| 5,277,913 A | 1/1994 | Thompson et al. | |
| 5,279,546 A | 1/1994 | Mische et al. | |
| 5,282,785 A | 2/1994 | Shapland et al. | |
| 5,286,254 A | 2/1994 | Shapland et al. | |
| 5,295,484 A | 3/1994 | Marcus et al. | |
| 5,295,958 A | 3/1994 | Shturman | |
| 5,304,115 A | 4/1994 | Pflueger et al. | |
| 5,307,816 A | 5/1994 | Hashimoto et al. | |
| 5,315,998 A | 5/1994 | Tachibana et al. | |
| 5,318,014 A | 6/1994 | Carter | |
| 5,323,769 A | 6/1994 | Bommannan et al. | |
| 5,324,255 A | 6/1994 | Passafaro et al. | |
| 5,327,891 A | 7/1994 | Rammler | |
| 5,328,470 A | 7/1994 | Nabel et al. | |
| 5,342,292 A | 8/1994 | Nita et al. | |
| 5,344,395 A | 9/1994 | Whalen et al. | |
| 5,344,435 A | 9/1994 | Turner et al. | |
| 5,345,940 A | 9/1994 | Seward et al. | |
| 5,353,798 A | 10/1994 | Sieben | |
| 5,354,279 A | 10/1994 | Hofling | |
| 5,362,309 A | 11/1994 | Carter | |
| 5,363,853 A | 11/1994 | Lieber | |
| 5,368,036 A | 11/1994 | Tanaka et al. | |
| 5,368,557 A | 11/1994 | Nita et al. | |
| 5,368,558 A | 11/1994 | Nita | |
| 5,380,273 A | 1/1995 | Dubrul et al. | |
| 5,385,148 A | 1/1995 | Lesh et al. | |
| 5,390,678 A | 2/1995 | Gesswein et al. | |
| 5,399,158 A | 3/1995 | Lauer et al. | |
| 5,409,458 A | 4/1995 | Khairkhahan et al. | |
| 5,415,636 A | 5/1995 | Forman | |
| 5,419,763 A | 5/1995 | Hildebrand | |
| 5,421,338 A | 6/1995 | Crowley et al. | |
| 5,423,797 A | 6/1995 | Adrian et al. | |
| 5,431,663 A | 7/1995 | Carter | |
| 5,445,155 A | 8/1995 | Sieben | |
| 5,447,509 A | 9/1995 | Mills et al. | |
| 5,447,510 A | 9/1995 | Jensen | |
| 5,456,259 A | 10/1995 | Barlow et al. | |
| 5,458,568 A | 10/1995 | Racchini et al. | |
| 5,462,523 A | 10/1995 | Samson et al. | |
| 5,465,726 A | 11/1995 | Dickinson et al. | |
| 5,474,530 A | 12/1995 | Passafaro et al. | |
| 5,474,531 A | 12/1995 | Carter | |
| 5,489,279 A | 2/1996 | Meserol | |
| 5,498,238 A | 3/1996 | Shapland et al. | |
| 5,509,896 A | 4/1996 | Carter | |
| 5,514,092 A | 5/1996 | Forman et al. | |
| 5,520,189 A | 5/1996 | Malinowski et al. | |
| 5,533,986 A | 7/1996 | Mottola et al. | |
| 5,542,935 A | 8/1996 | Unger et al. | |
| 5,558,092 A | 9/1996 | Unger et al. | |
| 5,558,642 A | 9/1996 | Schweich, Jr. et al. | |
| 5,567,687 A | 10/1996 | Magda et al. | |
| 5,569,197 A | 10/1996 | Helmus et al. | |
| 5,569,198 A | 10/1996 | Racchini | |
| 5,580,575 A | 12/1996 | Unger et al. | |
| 5,585,112 A | 12/1996 | Unger et al. | |
| 5,586,982 A | 12/1996 | Abela | |
| 5,588,432 A | 12/1996 | Crowley | |
| 5,588,962 A | 12/1996 | Nicholas et al. | |
| 5,594,136 A | 1/1997 | Sessler et al. | |
| 5,599,923 A | 2/1997 | Sessler et al. | |
| 5,603,327 A | 2/1997 | Eberle | |
| 5,603,694 A | 2/1997 | Brown et al. | |
| 5,606,974 A | 3/1997 | Castellano et al. | |
| 5,609,574 A | 3/1997 | Kaplan et al. | |
| 5,616,342 A | 4/1997 | Lyons | |
| 5,617,851 A | 4/1997 | Lipkovker | |
| 5,618,275 A | 4/1997 | Bock | |
| 5,620,479 A | 4/1997 | Diederich | |
| 5,628,728 A | 5/1997 | Tachibana et al. | |
| 5,628,730 A | 5/1997 | Shapland | |
| 5,630,837 A | 5/1997 | Crowley | |
| 5,632,970 A | 5/1997 | Sessler et al. | |
| 5,648,098 A | 7/1997 | Porter | |
| 5,656,016 A | 8/1997 | Ogden | |
| 5,660,180 A | 8/1997 | Malinowski et al. | |
| 5,663,327 A | 9/1997 | Tambo et al. | |
| 5,665,076 A | 9/1997 | Roth et al. | |
| 5,695,460 A | 12/1997 | Siegel et al. | |
| 5,697,897 A | 12/1997 | Buchholtz et al. | |
| 5,707,608 A | 1/1998 | Liu | |

| | | | | | | |
|---|---|---|---|---|---|---|
| 5,713,848 | A | 2/1998 | Dubrul et al. | 6,958,059 | B2 | 10/2005 | Zadno-Azizi |
| 5,715,825 | A * | 2/1998 | Crowley ............... 600/462 | 6,979,293 | B2 | 12/2005 | Hansmann et al. |
| 5,718,921 | A | 2/1998 | Mathiowitz et al. | 7,141,044 | B2 | 11/2006 | Gentsler |
| 5,725,494 | A | 3/1998 | Brisken | 2001/0000791 | A1 | 5/2001 | Suorsa et al. |
| 5,733,572 | A | 3/1998 | Unger et al. | 2001/0003790 | A1 | 6/2001 | Ben-Haim et al. |
| 5,735,811 | A | 4/1998 | Brisken | 2001/0007666 | A1 | 7/2001 | Hoffman et al. |
| 5,766,902 | A | 6/1998 | Craig et al. | 2001/0014775 | A1 | 8/2001 | Koger et al. |
| 5,770,222 | A | 6/1998 | Unger et al. | 2001/0041842 | A1 | 11/2001 | Eberle et al. |
| 5,772,632 | A | 6/1998 | Forman | 2001/0041880 | A1 | 11/2001 | Brisken et al. |
| 5,776,429 | A | 7/1998 | Unger et al. | 2001/0053384 | A1 | 12/2001 | Greenleaf et al. |
| 5,779,673 | A | 7/1998 | Roth et al. | 2002/0032394 | A1 | 3/2002 | Brisken et al. |
| 5,817,048 | A | 10/1998 | Lawandy | 2002/0068717 | A1 | 6/2002 | Borrelli |
| 5,836,896 | A | 11/1998 | Rosenschien | 2002/0151792 | A1 | 10/2002 | Conston et al. |
| 5,843,109 | A | 12/1998 | Mehta et al. | 2003/0040501 | A1 | 2/2003 | Newman et al. |
| 5,846,218 | A | 12/1998 | Brisken et al. | 2003/0069525 | A1 | 4/2003 | Brisken et al. |
| 5,849,727 | A | 12/1998 | Porter et al. | 2004/0024347 | A1 | 2/2004 | Wilson et al. |
| 5,876,345 | A | 3/1999 | Eaton et al. | 2004/0039329 | A1 | 2/2004 | Ueberle |
| 5,876,989 | A | 3/1999 | Berg et al. | 2004/0106847 | A1 | 6/2004 | Benderev et al. |
| 5,895,356 | A | 4/1999 | Andrus | 2005/0027247 | A1 | 2/2005 | Carrison et al. |
| 5,895,358 | A | 4/1999 | Becker et al. | | | | |
| 5,895,398 | A | 4/1999 | Wensel et al. | FOREIGN PATENT DOCUMENTS | | | |
| 5,897,503 | A * | 4/1999 | Lyon et al. ............... 600/459 | DE | 40 05 743 | | 8/1991 |
| 5,916,192 | A | 6/1999 | Nita et al. | EP | 0 189 329 | | 7/1986 |
| 5,922,687 | A | 7/1999 | Mann et al. | EP | 0 529 675 | | 8/1992 |
| 5,925,016 | A | 7/1999 | Chornenky et al. | EP | 0 629 382 | | 11/1993 |
| 5,938,595 | A | 8/1999 | Glass et al. | EP | 668052 | A2 | 2/1995 |
| 5,941,868 | A | 8/1999 | Kaplan et al. | EP | 0 744 189 | | 11/1996 |
| 5,997,497 | A | 12/1999 | Nita et al. | EP | 0 788 774 | | 8/1997 |
| 6,001,069 | A | 12/1999 | Tachibana et al. | EP | 0788774 | | 8/1997 |
| 6,024,718 | A | 2/2000 | Chen et al. | EP | 1 252 885 | | 10/2002 |
| 6,030,374 | A | 2/2000 | McDaniel | EP | 0 746 245 | | 11/2002 |
| 6,059,731 | A | 5/2000 | Seward et al. | JP | H 02-180275 | | 7/1990 |
| 6,063,069 | A | 5/2000 | Cragg et al. | WO | WO 89/04142 | | 5/1989 |
| 6,068,857 | A | 5/2000 | Weitschies et al. | WO | WO 89/05160 | | 6/1989 |
| 6,096,000 | A | 8/2000 | Tachibana et al. | WO | WO 91/09629 | | 7/1991 |
| 6,096,070 | A | 8/2000 | Ragheb et al. | WO | WO 92/00113 | | 1/1992 |
| 6,113,558 | A | 9/2000 | Rosenschein et al. | WO | WO 92/07622 | | 5/1992 |
| 6,117,101 | A | 9/2000 | Diederich et al. | WO | WO 93/08738 | | 5/1993 |
| 6,117,858 | A | 9/2000 | Porter et al. | WO | WO 94/05361 | | 3/1994 |
| 6,120,454 | A | 9/2000 | Suorsa et al. | WO | WO 95/01751 | | 1/1995 |
| 6,135,976 | A | 10/2000 | Tachibana et al. | WO | WO 95/05866 | | 3/1995 |
| 6,149,599 | A | 11/2000 | Schlesinger et al. | WO | WO 95/10233 | | 4/1995 |
| 6,176,842 | B1 | 1/2001 | Tachibana et al. | WO | WO 95/15118 | | 6/1995 |
| 6,206,831 | B1 | 3/2001 | Suorsa et al. | WO | WO 95/26777 | | 10/1995 |
| 6,210,356 | B1 | 4/2001 | Anderson et al. | WO | WO 96/04955 | | 2/1996 |
| 6,210,393 | B1 | 4/2001 | Brisken | WO | WO 96/07432 | | 3/1996 |
| 6,228,046 | B1 | 5/2001 | Brisken | WO | WO 96/15815 | | 5/1996 |
| 6,235,024 | B1 | 5/2001 | Tu | WO | WO 96/27341 | | 9/1996 |
| 6,245,747 | B1 | 6/2001 | Porter et al. | WO | WO 96/29935 | | 10/1996 |
| 6,277,077 | B1 | 8/2001 | Briskem et al. | WO | WO 96/35469 | | 11/1996 |
| 6,283,920 | B1 | 9/2001 | Eberie et al. | WO | WO 96/36286 | | 11/1996 |
| 6,287,271 | B1 | 9/2001 | Dubrul et al. | WO | WO 97/19645 | | 6/1997 |
| 6,295,990 | B1 | 10/2001 | Lewis et al. | WO | WO 97/21462 | | 6/1997 |
| 6,296,619 | B1 | 10/2001 | Brisken et al. | WO | WO 98/11826 | | 3/1998 |
| 6,309,370 | B1 | 10/2001 | Haim et al. | WO | WO 98/18391 | | 5/1998 |
| 6,312,402 | B1 | 11/2001 | Hansmann | WO | WO 98/48711 | | 11/1998 |
| 6,346,098 | B1 | 2/2002 | Yock et al. | WO | WO 98/58699 | | 12/1998 |
| 6,372,498 | B2 | 4/2002 | Newman et al. | WO | WO 99/25385 | | 5/1999 |
| 6,416,740 | B1 | 7/2002 | Unger | WO | WO 99/33500 | | 7/1999 |
| 6,425,853 | B1 | 7/2002 | Edwards | WO | WO 99/34858 | | 7/1999 |
| 6,433,464 | B2 | 8/2002 | Jones | WO | WO 99/39738 | | 8/1999 |
| 6,461,296 | B1 | 10/2002 | Desai | WO | WO 99/44512 | | 9/1999 |
| 6,461,383 | B1 | 10/2002 | Gesswein et al. | WO | WO 00/00095 | | 1/2000 |
| 6,464,680 | B1 | 10/2002 | Briskem et al. | WO | WO 00/38580 | | 7/2000 |
| 6,508,816 | B2 | 1/2003 | Shadduck | | | | |
| 6,524,251 | B2 | 2/2003 | Rabiner et al. | OTHER PUBLICATIONS | | | |

Lee et al.; "Arrays of Multielement Ultrasound Applicators for Interstitial Hyperthermia"; IEEE Transactions on Biomedical Engineering; vol. 46, No. 7; Jul. 1999.

Akhtar, Anti-HIV therapy with antisense oligonucleotides and ribozymes: realistic approaches or expensive myths? (J. Antimicrob Chemother. 38(2): 159-165, 1996).

Anderson, Human gene therapy. (Nature 392:25-30, 1998).

B.D. Butler, J. clin. Ultrasound 14(5): 408-12 (Jun. 1986) Production of Microbubbles for Use as Echo Contrast Agents*.

Bao, et al. "Transfection of a Reporter Plasmid into Cultured Cells by Sonoporation In Vitro," Ultrasound in Med. and Biol., vol. 23, No. 6, pp. 953-.

Bleeker et al., J. Ultrasound, Med. 9(8): 461-71 (Aug.1990) on the Application of Ultrsonic Contrast Agents for Blood Flowmetry and Assessment of Cardiac Perfusion*.

Branch, A Good Antisense Molecule is Hard to Find, (Trends in Biochem Sci 23: 45-50, 1998).

Cancer Letters, vol. 72, 1993, pp. 195-199, Tachibana.

Cancer Letters, vol. 78 (1-3), 1994, pp. 177-181, Tachibana.

Crooke, Basic Principles of Antisense Therapeutics (Springer-Verlag, Eds, New York, 1998, pp. 1 and 4).

Fechmeier, et al. "Transfection of Mammalian Cells with Plasid DNA by Scrape Loading and Sonication Loading," Proc. Natl. Acad. Sci. USA, vol. 84, pp. 8463-8467, Dec. 1987.

Feinstein et al., J. Am. Coll. Cardiol. 3(1): 14-20 (Jan. 1984) Two-dimensional Contrast Echocardiography I. In Vitrro Development and Quantitative Analysis of Echo Contrast Agents*.

Feldman, et al. "Optimal Techniques for Arterial Gene Transfer," Cardiovascular Research, 35 (1997) pp. 391-404.

Maywald G. et al., "Experience With Atraumatic Vascular Diagnosis With the Aid of the Ultrasonic Doppler Technique", Electromedica, vol. 2 pp. 43-48 (1976).

Greenleaf, William J. et al.; Artifical Cavitation Nuclei Significantly Enhance Accoustically Induced Cell Transfection. vol. 24, No. 4 pp. 587-595, 1998.

Ho and Parkinson, Antisense Oigonucleoties and Therapeutics for Malignant Diseases, (Seminars in Drug Discovery 24(2): 187-202, 1997).

Holland, C.K. and R.E. Apfel, J. Acoust. Soc. Am. 88(5): 2059-2069 (Nov. 1990) Thresholds for Transient Caviation Produced by Pulsed Ultrsound in a Controlled Nuclei Environment*.

Yumita N., Japanese Journal of Cancer Research, vol. 81, No. 3, Mar. 1990, pp. 304-308.

Jeffers, R.J. et al.; Evaluation of the Effect of Cavitation Activity on Drug-Ultrsound Synergisms, 1993.

Jeffers, Russel et al; Dimethylformamide as an Enhancer of Cavitation-Induced Cell Lysis In Vitro, vol. 97, No. 1, Jan. 1995.

Keller et al., J. Ultrasound Med. 5(9): 493-8 (Sep. 1986) Automated Production and Analysis of Echo Contrast Agents*.

Kim, et al. "Ultra-sound Mediated Transfection of Mammalian Cells," Human Gene Therapy, 7: 1339-1346 (Jul. 10, 1996).

Kim, T.F. Medical news & Perspectives, JAMA 261(11): 1542 (Mar. 17, 1989) Microbubbles Show Promise for Enhancing Ultrasound Signal, Image, Other Applications*.

Kotnis, et al. "Optimisation of Gene Transfer into Vascular Endothelial Cells Using Electroporation," Eur J. Vasc Surg, 9, 71-79 (1995).

Lang et al., Circulation 75(1): 229-234 (Jan. 1987) Contrast Ultrasonography of the Kidney: a New Method for Evaluation of Renal Perfusion in Vivo*.

Leong et al., Biomaterials, vol. 7: 364-371 (Sep. 1986) Polyanhydrides for Controlled Release of Bioactive Agents*.

Meltzer et al., J. Clin. Ultrasound 8(2): 121-7 (Apr. 1980) The Source of Ultrsound Contrast Effect*.

Miller, Douglas L. et al.; Sonoporation of Cultured Cells in the Rotation Tube Exposure System, vol. 25, No. 1, 1999.

Orkin and Motulsky, Report and Recommendations of the Panel to Assess the NIH Investment in Research on Gene Therapy, (p. 1-38, Dec. 7, 1995).

PCT Search Report, PCT Application PCT/US2006/13531; Apr. 12, 2006.

Porter, et al "Interaction of Diagnostic Ultrasound with Synthetic Olionucleotide-Labeled Perfluorcarbon-Exposed Sonicated Dextrose Albumin Microbubbles," J Ultrasound Med, 15:557-584, 1996.

Porter, T.R. et al., Thrombolytic Enhancement With Perfluorocarbom-Exposed Sonicated Dextrose Albumin Microbubbles, Nov. 1996.

Prat, F. et al.; In Vivo Effects of Cavitation Alone or in Combination Wity Chemotherapy in a Peritoneal Carinomatosis in the Rat. vol. 68, pp. 13-17.

Price, Richard et al.; Delivery of Colloidal Particles and Red Blood Cells to Tissue Through Microvessel Ruptures Created by Targeted Microbubble Destruction With Ultrasound, Sep. 29, 1998.

Romano et al., Latest Developments in Gene Transfer Technology: Achievements, Perspectives, and Controversies over Therapeutice Applications, (Stem Cells 18: 19-39, 2000).

Rosenschein, U. et al., Experimental Ultrasonic Angioplasty: Disruption of Atherosclerotic Plaques and Thrombi in Vitro and Arterial Recanalization in.

Somia and Verma, Gene Therapy: Trials and Tribulations, (Nature Reviews Genetics 1:91-99, 2000).

Tachibana K.; Albumin Microbubble Echo-Contrast Materials as an Enhancer for Ultrasound Accelerated Thrombolysis, Sep. 1, 1995.

Tachibana, K. "Enhancement of Fibrinolysis with Ultrasound Energy", JVIR, vol. 3, No. 2, May 1992, pp. 299-303.

Tsurumi, et al. "Direct Intramuscular Gene Transfer of Naked DNA Encoding Vascular Endothelial Growth Factor Augments Collateral Development and Tissue Perfusion," Circulation, 1996; 94: 3281-3290.

Unger, et al. "Ultrasound Enhances Gene Expression of Liposomal Transfection," Investigative Radiology, vol. 32, No. 12, pp. 723-727, 1997.

Unger, Evan C. et al.; Acoustically Active Liposheres Containing Paclitaxel, vol. 11, No. 12, 1992.

Vandenburg et al., Am. Heart J., 115(4), 733-9 (Apr. 1988) Myocardial Risk Area and Peak Gray Level Measurement by Contrast Echocardiography: Effecct of Microbubble Size and Concentration, Injection Rate, and Coronary Vasodilation*.

Verma et al., Gene Therapy—promises, problems and prospects, (Nature 389: 239-242, 1997).

Wheatly et al., Biomaterials 11(19): 713-7 (Nov. 1990) Contrast Agents for Diagnostic Ultrsound: Development and Evaluation of Polymer-Coated Microbubbles*.

Wu, Yunqiu et al., Binding as Lysing of Blood Clots Using MRX-408, May 1998.

Wyber, et al. "The Use of Sonication for the Efficient Delivery of Plasmid DNA into Cells," Pharmaceutical Research, vol. 14, No. 6, pp. 750-756.

Hynynen et al.; "Small Cylindrical Ultrasound Sources Fro Induction of Hyperthermia via Body Cavities or Interstitial Implants"; Arizona Cancer Center and Department of Radiation Oncology, University of Arizona Health Sciences Center; vol. 9, No. 2; pp. 263-274; 1993.

Lee et al.; "Arrays of Mulielement Ultrasound Applicators for Interstitial Hyperthermia"; IEEE Transactions on biomedical Engineering; vol. 46, No. 7; Jul. 1999.

* cited by examiner

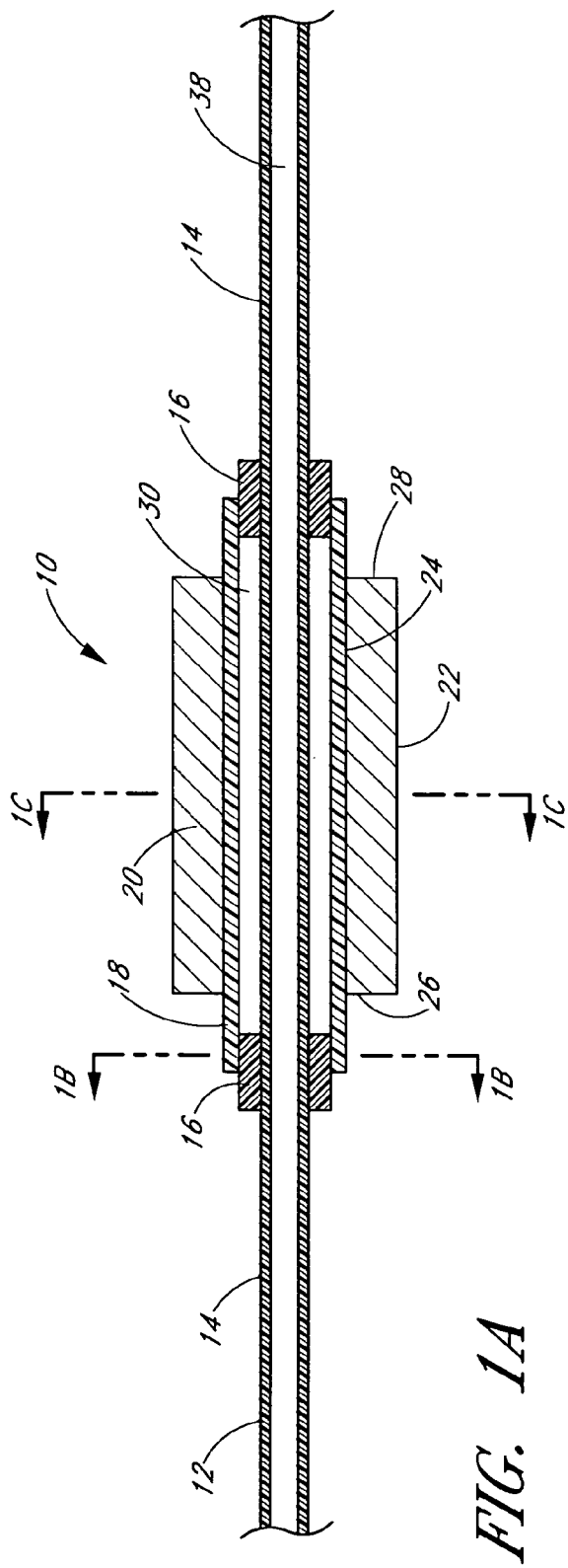
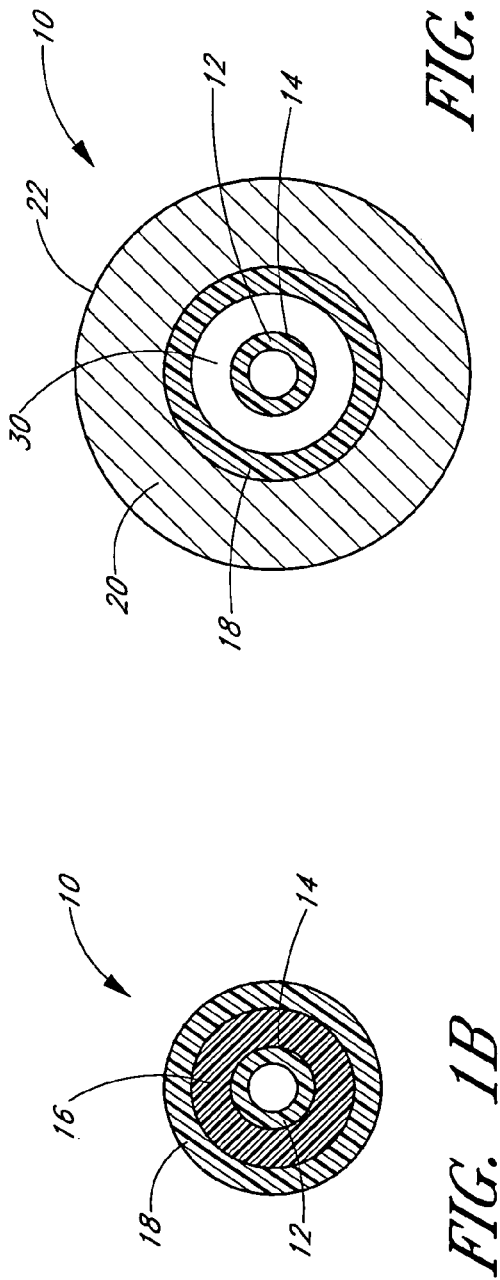
FIG. 1A
FIG. 1B
FIG. 1C

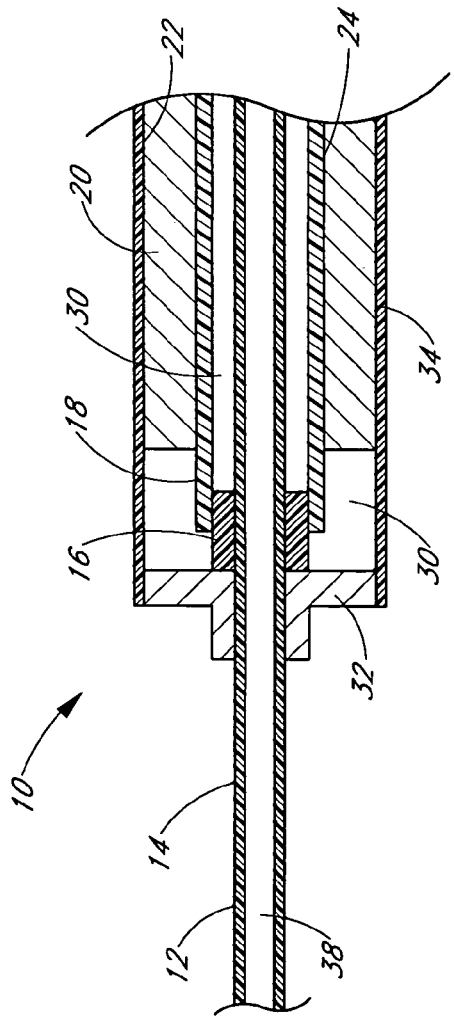
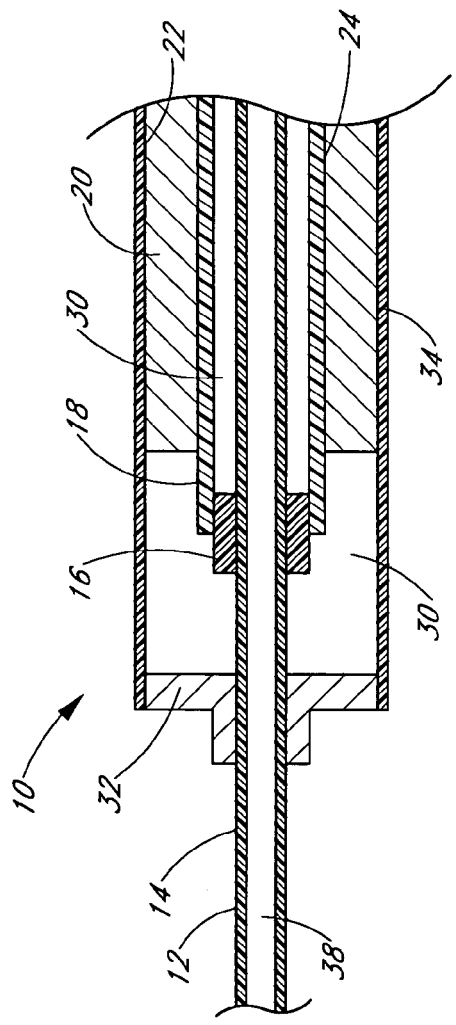
FIG. 4A
FIG. 4B

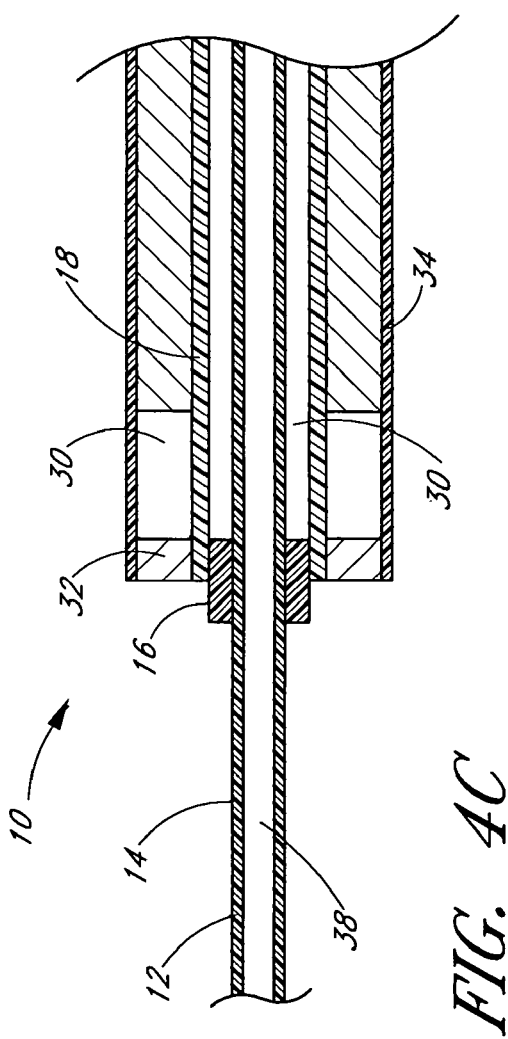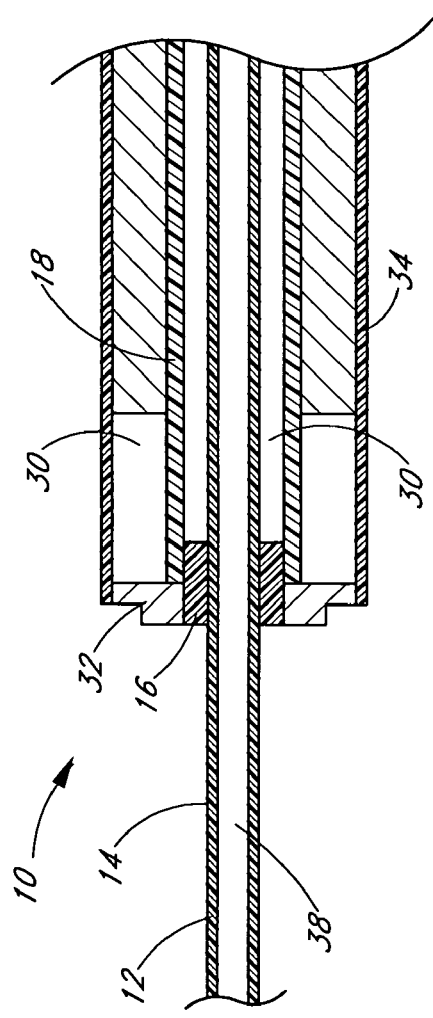
FIG. 4C
FIG. 4D

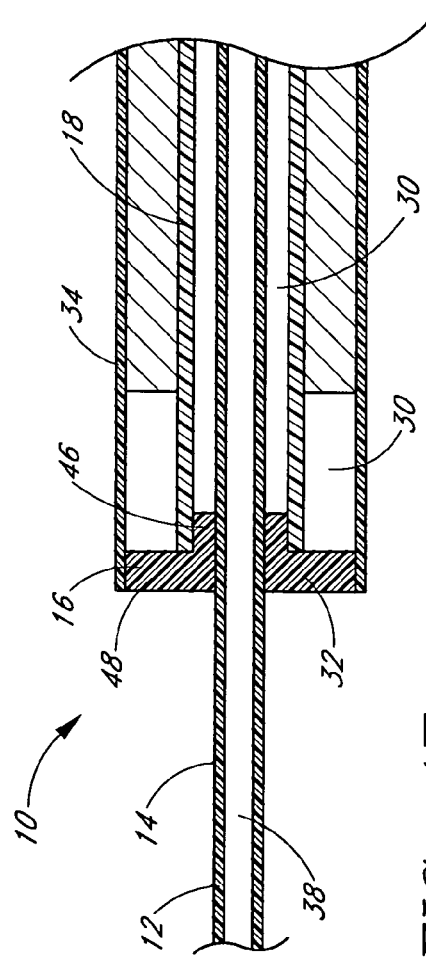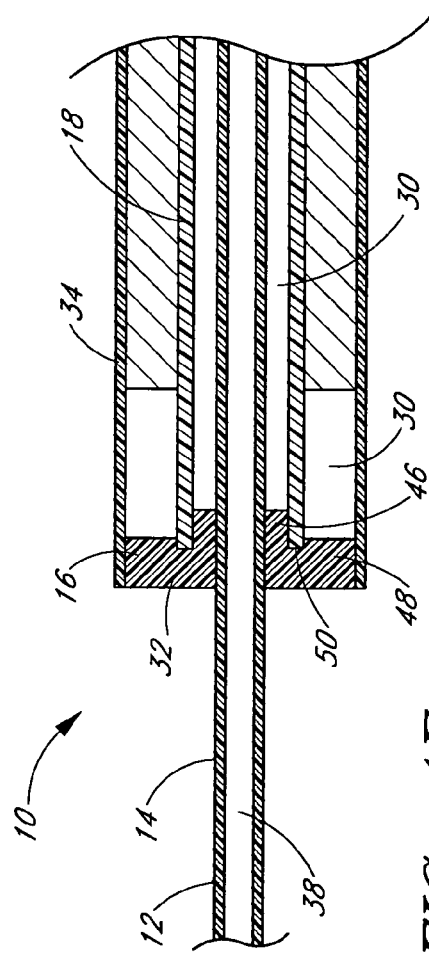

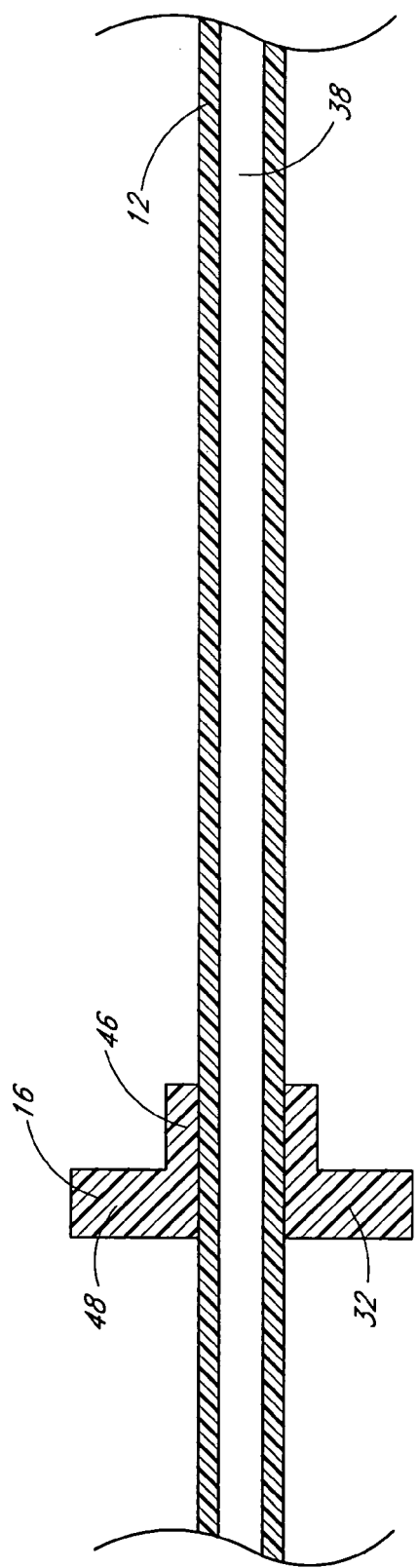
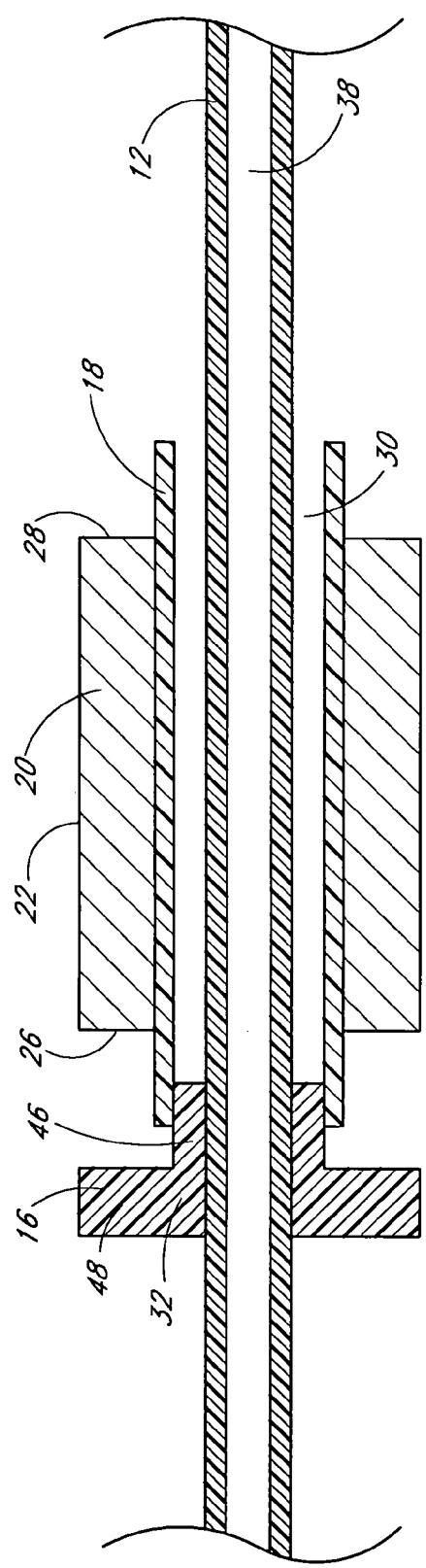
FIG. 8A
FIG. 8B

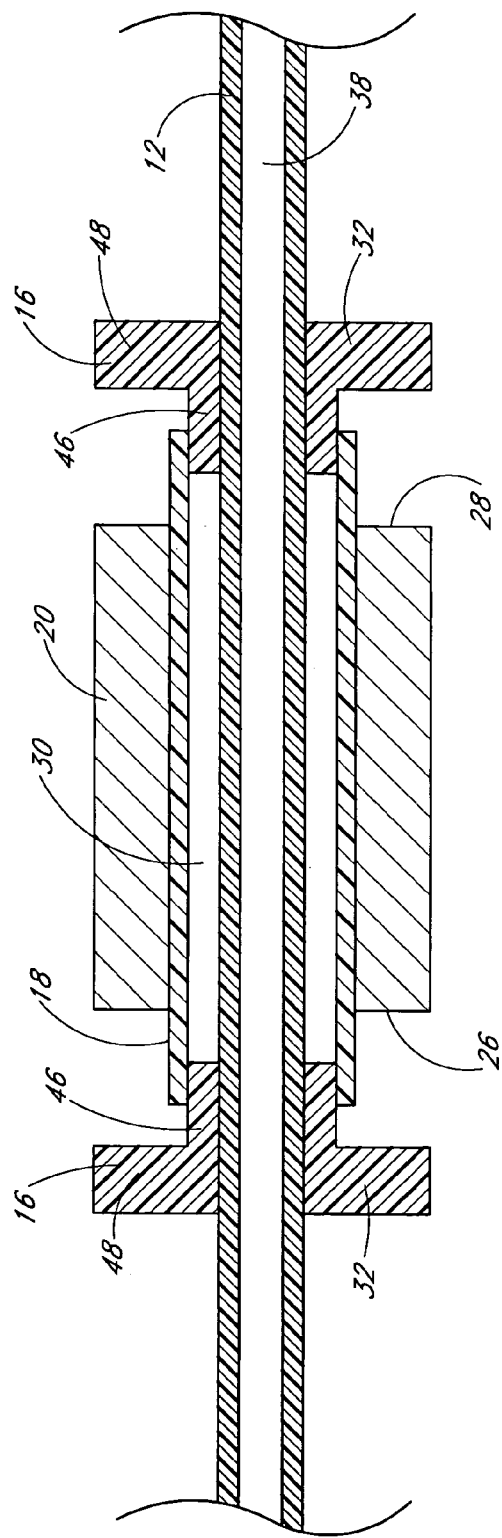
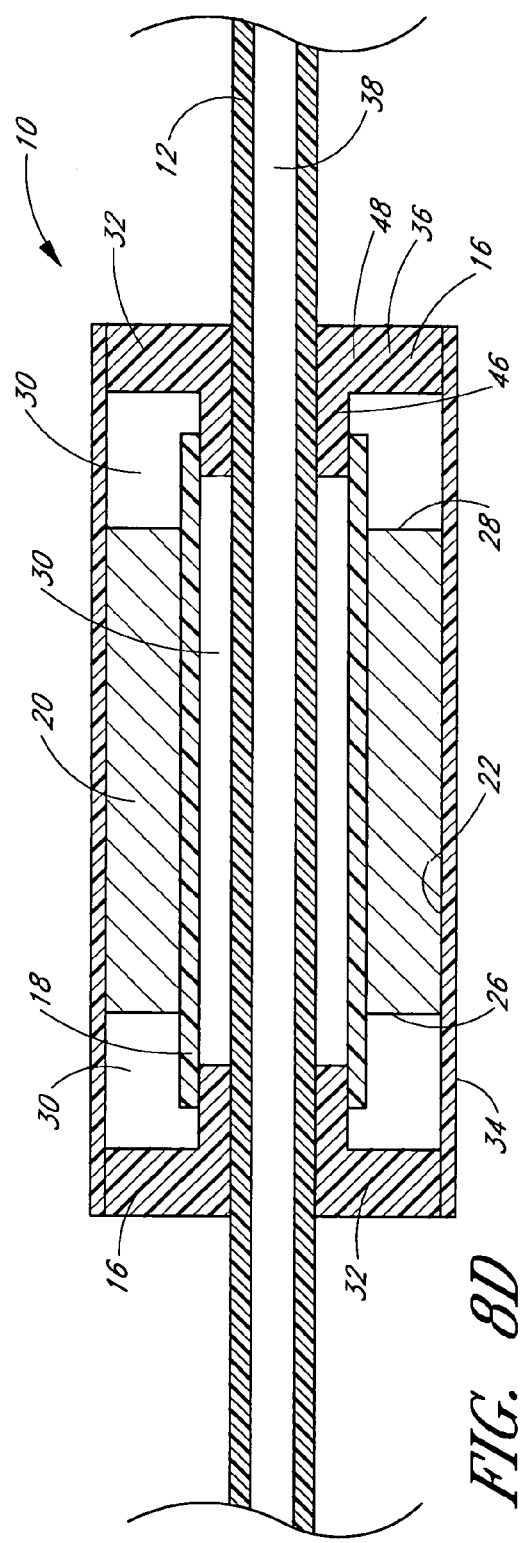
FIG. 8C
FIG. 8D

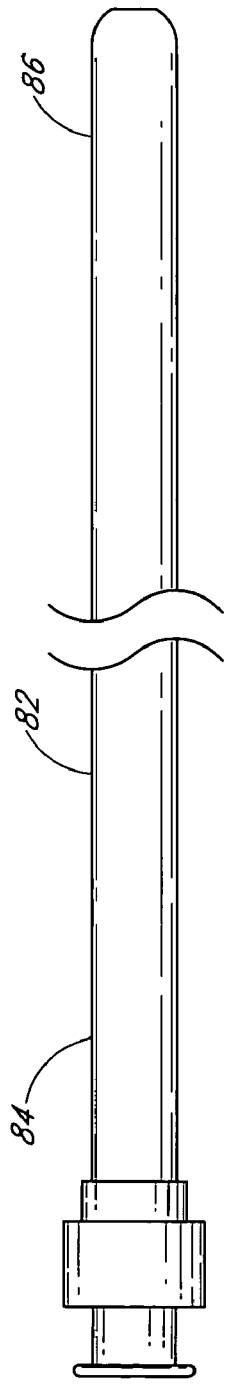
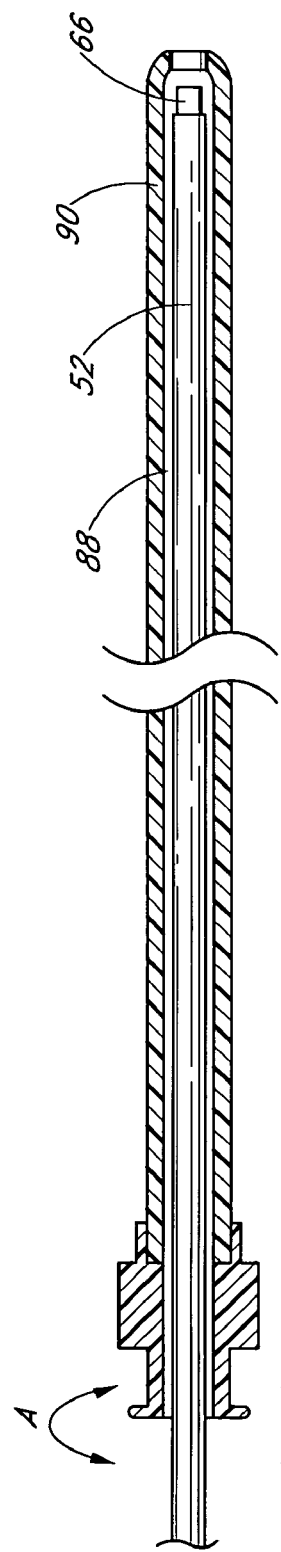
FIG. 12A
FIG. 12B

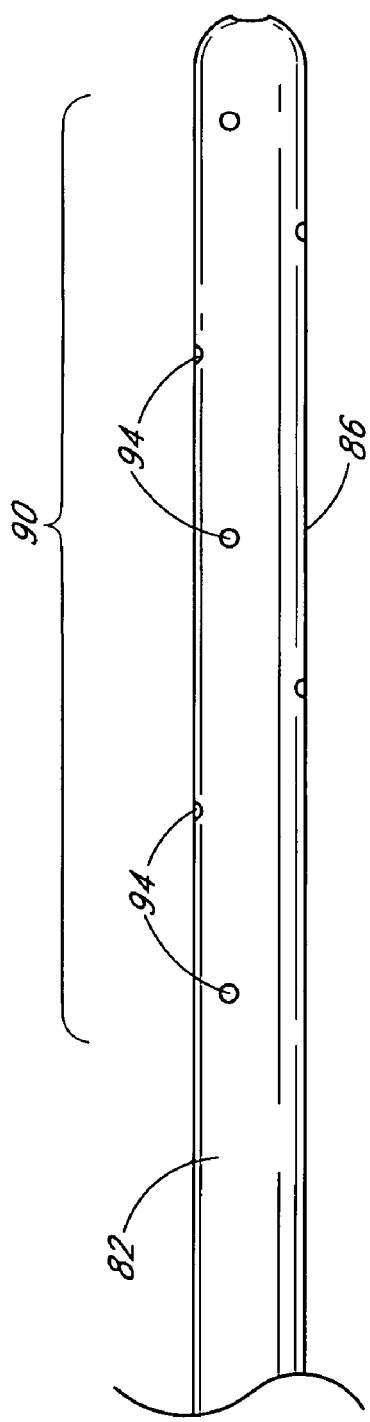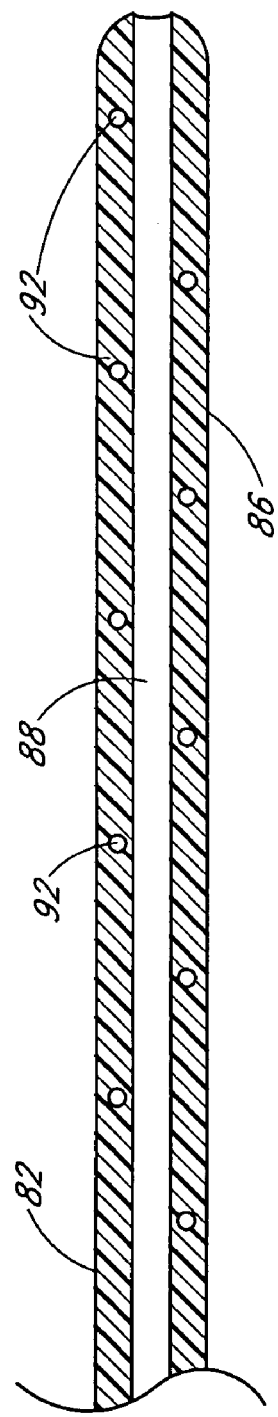
FIG. 12C
FIG. 12D

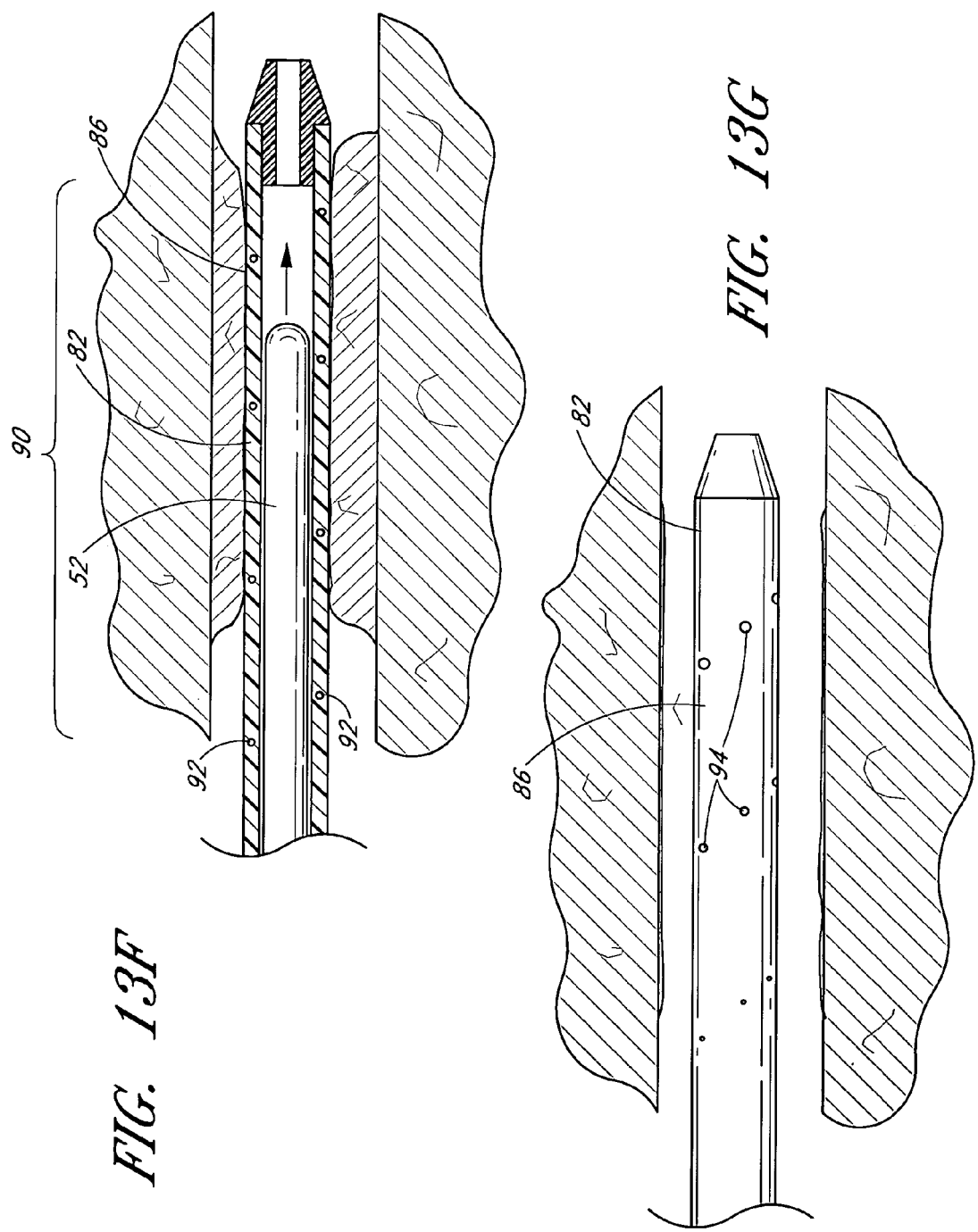

ULTRASOUND ASSEMBLY WITH INCREASED EFFICACY

RELATIONSHIP TO APPLICATIONS

This application is a continuation of U.S. patent application Ser. No. 09/374,642 (filed 16 Aug. 1999), now U.S. Pat. No. 6,676,626 which is a continuation-in-part of U.S. patent application Ser. No. 09/129,980 (filed 5 Aug. 1998), now U.S. Pat. No. 6,210,356 and is a CIP of U.S. patent application Ser. No. 09/375,162 (filed 16 Aug. 1999), now U.S. Pat. No. 6,582,392 and is a CIP of U.S. patent application Ser. No. 09/107,078 (filed 29 Jun. 1998) now U.S. Pat. No. 6,723,063 and is a CIP of U.S. patent application Ser. No. 09/071,285 (filed 1 May 1998) now U.S. Pat. No. 6,001,069. U.S. patent application Ser. No. 09/071,285 claims the benefit of U.S. Provisional Application 60/045,268 (filed 1 May 1997). The entire disclosure of all six of these priority applications is hereby incorporated by reference herein.

BACKGROUND OF THE INVENTION

1. Field of the Invention

The present invention relates to a catheter, and more particularly, to a catheter having an ultrasound assembly.

2. Description of Related Art

Many medical treatments can be performed using catheters with an ultrasound transducer. These ultrasound transducers deliver ultrasound energy to a target site within a patient. The ultrasound energy can provide a therapeutic effect by itself or can enhance the effects of other therapeutic media exposed to the ultrasound energy. Inefficient ultrasound transducer arrangements can generate excessive heat during a medical treatment.

SUMMARY OF THE INVENTION

The invention relates to a catheter system. The system comprises a catheter body having a chamber containing a low acoustic impedance medium. The catheter body includes an elongated body with an external surface and an ultrasound transducer having an external side between a first end and a second end. The ultrasound transducer is positioned over the external surface of the elongated body such that the first end of the ultrasound transducer is adjacent to the chamber.

Another embodiment of the system comprises a catheter body having an external surface. The catheter body includes an ultrasound transducer having a side between a first end and a second end. A first medium is positioned adjacent to the first end of the ultrasound transducer and a second medium is positioned adjacent to the external side of the ultrasound transducer. The second medium is harder than the first medium to encourage flexibility of the catheter body adjacent to the first end of the ultrasound transducer and efficient transmission of ultrasound energy from the external side of the ultrasound transducer.

The catheter system can also include a sheath for receiving the catheter.

The invention also relates to a method for forming a catheter. The method includes positioning an ultrasound transducer over an external surface of an elongated body and positioning a collar over the external surface of the elongated body such that at least a portion of the collar is spaced apart from the ultrasound transducer. The method also includes positioning a transducer sheath over at least a portion of the ultrasound transducer and over at least a portion of the collar to form a chamber between the ultrasound transducer and the collar.

Another embodiment of the method includes positioning a first spacer over an external surface of an elongated body and positioning a member over at least a portion of the first spacer so as to form a chamber between the member and the external surface of the elongated body. The method also includes positioning an ultrasound transducer over the member.

Yet another embodiment of the method includes providing an ultrasound transducer having a side between a first end and a second end. The ultrasound transducer is positioned over an external surface of an elongated body. The method includes forming a first medium adjacent to the first end of the ultrasound transducer and forming a second medium adjacent to the side of the ultrasound transducer. The second medium is harder than the first medium to encourage flexibility of the catheter body adjacent to the first end of the ultrasound transducer and efficient transmission of ultrasound energy from the external side of the ultrasound transducer.

BRIEF DESCRIPTION OF THE FIGURES

FIGS. 1A-1H illustrate a plurality of ultrasound assembles for use with catheters according to the present invention.

FIG. 1A is a cross section of an ultrasound assembly having a chamber between an ultrasound transducer and an external surface of an elongated body.

FIG. 1B illustrates the relationship between spacers and the elongated body for the embodiment of the ultrasound assembly illustrated in FIG. 1A.

FIG. 1C illustrates the relationship between the ultrasound transducer and the elongated body for the embodiment of the ultrasound assembly illustrated in FIG. 1A.

FIG. 1D illustrates an ultrasound assembly having a chamber adjacent to an end of the ultrasound transducer and a chamber between the ultrasound transducer and the external surface of the elongated body.

FIG. 1E illustrates an ultrasound assembly having chambers adjacent to both ends of the ultrasound transducer and a chamber between the ultrasound transducer and the external surface of the elongated body FIG. 1F illustrates an ultrasound assembly having a chamber adjacent to an end of the ultrasound transducer.

FIG. 1G illustrates an ultrasound assembly having chambers adjacent to both ends of the ultrasound transducer.

FIG. 1H illustrates an ultrasound assembly without chambers.

FIGS. 4A-4F illustrate ultrasound assemblies having a spacer for creating a chamber between a side of an ultrasound transducer and an external surface of an elongated body. The ultrasound assemblies also include a collar for creating a chamber adjacent to the ends of the ultrasound transducer.

FIG. 4A illustrates the collar abutting the spacer.

FIG. 4B illustrates the collar in a spaced apart relationship to the spacer.

FIGS. 4C and 4D illustrate the collar positioned over the spacer.

FIGS. 4E and 4F illustrate the collar integral with the spacer.

FIG. 6A illustrates a catheter having ultrasound assemblies spaced apart from a catheter sheath.

FIG. 6B illustrates a catheter having ultrasound assemblies in contact with a catheter sheath.

FIG. 6C illustrates a catheter having ultrasound assemblies which share a member.

FIGS. 8A-8D illustrate a method for forming an ultrasound assembly when a collar for forming a chamber adjacent to the ultrasound transducer is integral with a spacer for forming a chamber between the ultrasound transducer and an external surface of an elongated body.

FIG. 10A illustrates a catheter sheath positioned over an extension region, an assembly region and a terminal region of a catheter body.

FIG. 10B illustrates a binding medium delivered adjacent to an end of the ultrasound transducer.

FIG. 10C illustrates a binding medium delivered adjacent to an external side of the ultrasound transducer.

FIG. 10D illustrates a first binding medium delivered adjacent to an external side of the ultrasound transducer and a second binding medium delivered adjacent to an end of the ultrasound transducer.

FIGS. 12A-12D illustrate a sheath for use with a catheter according to the present invention.

FIG. 12A is a sideview of the sheath.

FIG. 12B illustrates a catheter according to the present invention positioned within the sheath.

FIG. 12C is a sideview of a sheath having a drug delivery lumen which spirals around a sheath distal end.

FIG. 12D is a cross section of a sheath having a drug delivery lumen which spirals around a sheath distal end.

FIGS. 13A-13G illustrate a method for using a catheter according to the present invention in conjunction with a sheath.

DETAILED DESCRIPTION

Figure 1D:
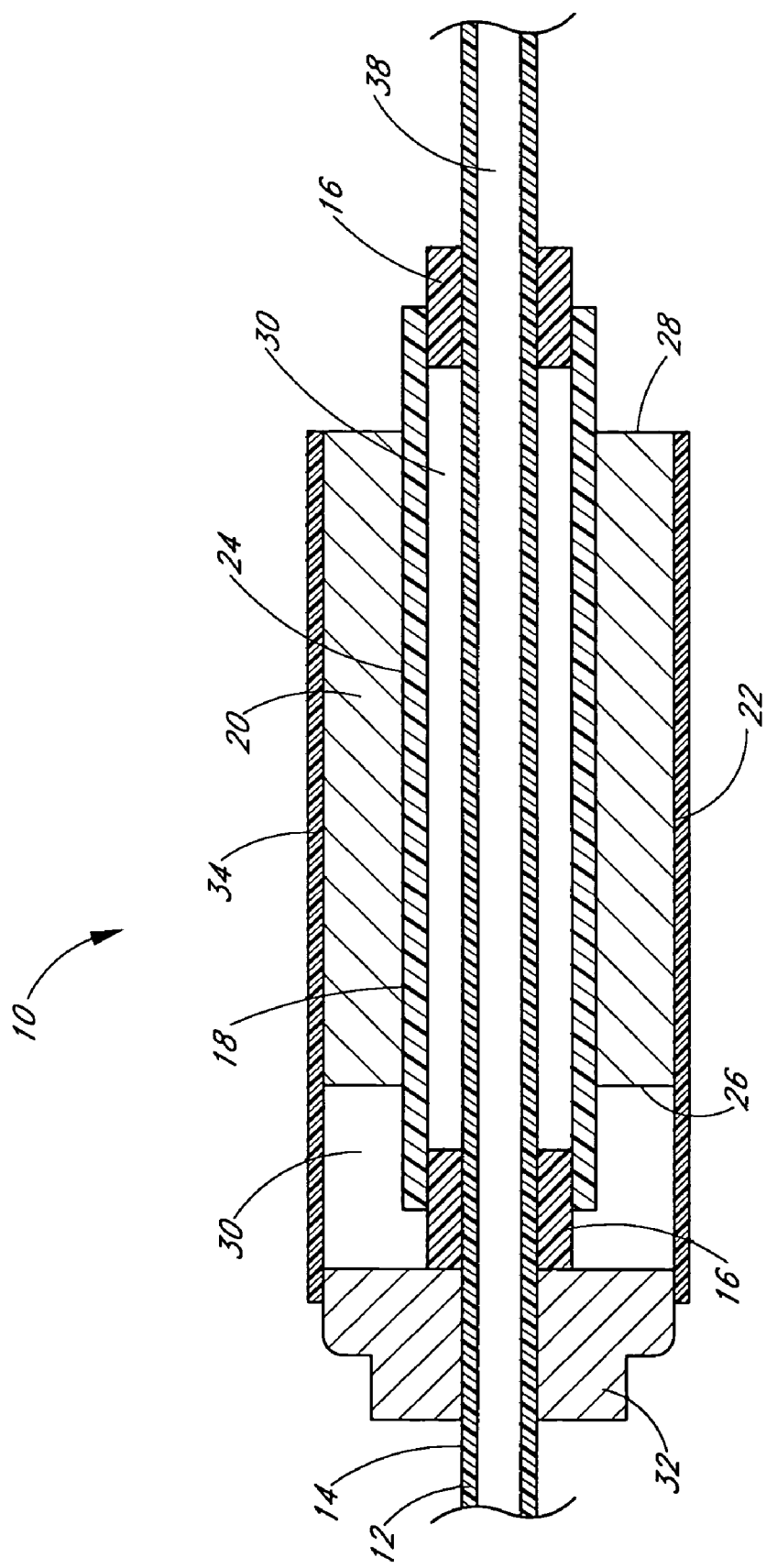

The invention relates to a catheter having a chamber containing a low acoustic impedance medium. The catheter can also include an elongated body with an external surface. An ultrasound transducer having an external side between a first end and a second end can be positioned over the external surface of the elongated body such that the first side of the ultrasound transducer is adjacent to the chamber.

The low acoustic impedance material within the chamber reduces the portion of ultrasound energy which is transmitted through the chamber. This reduction causes an increased portion of ultrasound energy to be delivered from the second end of the ultrasound transducer and/or from the external side of the ultrasound transducer. As a result, the ultrasound energy produced from these sections of the ultrasound transducer is delivered with a greater efficiency.

The ultrasound transducer can be positioned distally relative to the chamber in order to increase the efficiency of the ultrasound energy transmitted in the distal direction. Alternatively, the ultrasound transducer can be positioned proximally relative to the chamber in order to increase the efficiency of the ultrasound energy transmitted in the proximal direction.

Another embodiment of the catheter includes a chamber between the elongated body and an internal side of the ultrasound transducer. The chamber can include a low acoustic impedance medium to reduce the portion of ultrasound energy transmitted into the elongated body. As a result, the ultrasound energy produced from the ends and the external side of the ultrasound transducer is delivered with a greater efficiency than could be achieved without the chamber.

A catheter according to the present invention can include various combinations of the above chambers. Each of the chambers can be independent of one another or they can be in communication with one another. The chambers can contain a low acoustic impedance medium. For instance, a catheter can include a first chamber adjacent to the first end of the ultrasound transducer, a second chamber adjacent to the second end of the ultrasound transducer and a third chamber between the internal side of the ultrasound transducer and the elongated body. As a result, the ultrasound energy produced from the external surface of the catheter is delivered at an increased efficiency. Such a catheter efficiently delivers ultrasound energy from the side of the catheter.

As another example, a catheter can include the first chamber adjacent to the first end of the ultrasound transducer and the third chamber between the internal side of the ultrasound transducer and the elongated body. Further, the ultrasound transducer can be positioned distally relative to the first chamber. The chambers can contain a low acoustic impedance medium. As a result, the ultrasound energy produced from the second end and the external surface of the catheter is delivered at an increased efficiency. Such a catheter efficiently delivers ultrasound energy both distally and from the side of the catheter.

A catheter according to the present invention can also include a plurality of ultrasound transducers. Each ultrasound transducer can be associated with one or more chambers. As a result, each ultrasound transducer can have an increased efficiency.

An embodiment of a catheter having a plurality of ultrasound transducers includes ultrasound transducers with matched resonant frequencies. For instance, the catheter can include ultrasound transducers selected such that any one has a resonant frequency within about 1% of the resonant frequency of any other ultrasound transducer in the plurality of ultrasound transducers. The matching of the ultrasound transducers allows the ultrasound transducers to be concurrently driven at a single frequency while reducing the inefficiencies associated with driving ultrasound transducers at a frequency which is significantly different than their resonant frequency.

Another embodiment of the catheter includes a first binding medium adjacent to the first end of the ultrasound transducer and a second binding medium adjacent to the external side of the ultrasound transducer. The first and second media are selected to provide the catheter with flexibility and a high level of ultrasound transmission efficiency. Since a softer media is typically more flexible and harder media typically transit ultrasound energy more efficiently, the second medium is preferably harder than the first medium. The advantages of the first and second media are emphasized in multiple ultrasound transducer catheters which tend to lose flexibility with the increased number of ultrasound transducers.

Catheters according to the present invention can also include an autotransformer in the proximal portion of the catheter. The autotransformer can serve to adjust the characteristic impedance of the catheter to match the impedance of components used to drive the one or more ultrasound transducers included on the catheter. The matched impedance serves to increase the efficiency of the catheter system.

Catheters according to the present invention can also include a catheter identification electronics. The catheter identification electronics indicate to a catheter control system the frequency that ultrasound transducers should be driven.

FIGS. 1A-1C illustrate an embodiment of an ultrasound assembly 10 according to the present invention for use with a catheter according to the present invention. FIG. 1A is a longitudinal cross sectional view of the ultrasound assembly 10. FIG. 1B is a lateral cross section of the ultrasound assembly 10 taken at the point labeled A in FIG. 1A. FIG. 1C is a lateral cross section of the ultrasound assembly 10 taken at the point labeled B in FIG. 1A.

The ultrasound assembly 10 includes an elongated body 12 with an external surface 14. A plurality of spacers 16 are positioned over the external surface 14 of an elongated body 12 and a member 18 is positioned over at least a portion of the spacers 16. The ultrasound assembly 10 also includes an ultrasound transducer 20 with an external side 22 and an internal side 24 between a first end 26 and a second end 28. The ultrasound transducer 20 is positioned over the member 18 and can surround the member 18. Suitable materials for the member 18 include, but are not limited to, polyimide, polyester and nylon. A suitable ultrasound transducer 20 includes, but is not limited to, PZT-4D, PZT-4, PZT-8 and various piezoceramics.

The internal side 24 of the ultrasound transducer 20, the spacers 16 and the member 18 each define a portion of a chamber 30 between the internal side 24 of the ultrasound transducer 20 and the external surface 14 of the elongated body 12. The chamber 30 preferably has a height from 0.25-10 μm, more preferably from 0.50-5 μm and most preferably from 0.0-1.5 μm.

The member 18 can extend beyond the first end 26 and/or the second end 28 of the ultrasound transducer 20. Additionally, the spacers 16 can be positioned beyond the ends of the ultrasound transducer 20. As a result, the chamber 30 can extend along the longitudinal length of the ultrasound transducer 20 to increase the portion of the ultrasound transducer 20 which is adjacent to the chamber 30.

The chamber 30 can contain a low acoustic impedance medium. Suitable low acoustic impedance media include, but are not limited to, fluids such as helium, argon, air and nitrogen and/or solids such as silicone and rubber. The chamber 30 can also be evacuated. Suitable pressures for an evacuated chamber 30 include, but are not limited to, negative pressures to −760 mm Hg.

As illustrated in FIG. 1D, the internal side 24 of the ultrasound transducer 20 can also be positioned adjacent to a chamber 30. The ultrasound assembly 10 includes a collar 32 over external surface 14 of the elongated body 12. The collar 32 can surround the elongated body 12. The collar 32 has a spaced apart relationship to the ultrasound transducer 20.

A transducer sheath 34 is positioned over at least a portion of the ultrasound transducer 20 and the collar 32 to form a chamber 30 adjacent to a side of the ultrasound transducer 20. An inner side of the collar 32, the ultrasound transducer 20 and the transducer sheath 34 each partially define the chamber 30. The chamber 30 preferably has a width, W, from 12-2500 μm, more preferably from 25-250 μm and most preferably from 25-125 μm. The chamber 30 can contain a low acoustic impedance medium. Suitable materials for the transducer sheath 34 include, but are not limited to air, $N^2$, $O^2$, and vacuum. The transducer sheath 34 preferably has a thickness from 10-100 μm and more preferably from 25-50 μm.

Figure 1E:
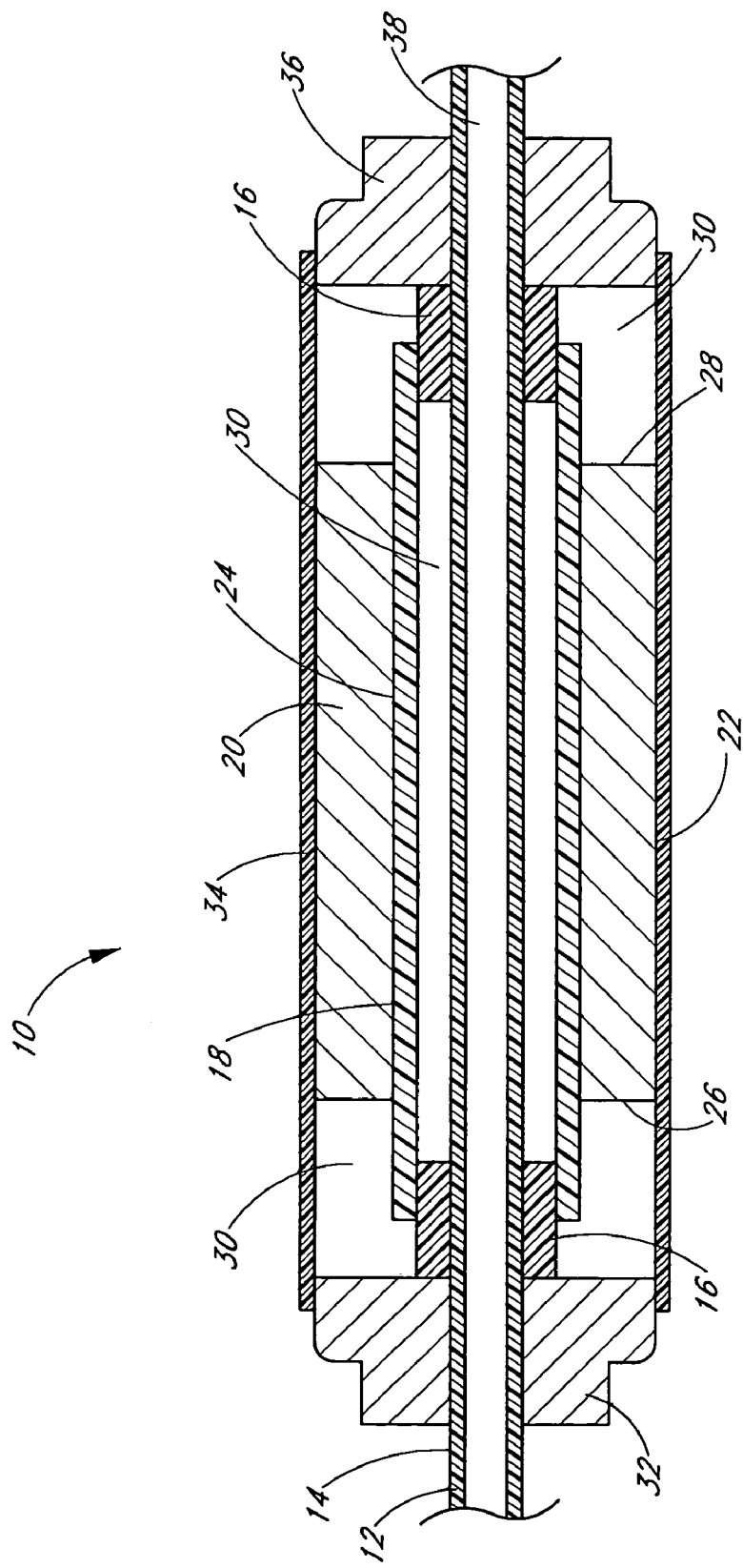

The ultrasound assembly 10 can also include a chamber 30 adjacent to the second end 28 of the ultrasound transducer 20 as illustrated in FIG. 1E. A second collar 36 is positioned over the elongated body 12 and can surround the external surface 14 of the elongated body 12. The second collar 36 has a spaced apart relationship from the ultrasound transducer 20 so as to provide a second chamber 30 adjacent to the ultrasound transducer 20. An inner side of the second collar 36, the ultrasound transducer 20 and the transducer sheath 34 each partially define the chamber 30. The chamber 30 preferably has a width, W, from 12-2500 μm, more preferably from 25-250 μm and most preferably from 25-125 μm. The chamber 30 adjacent to the second end 28 of the ultrasound transducer 20 can also contain a low acoustic impedance medium.

Each of the chambers can be isolated from one another. However, when the ultrasound assembly 10 includes a chamber 30 between the ultrasound transducer 20 and the elongated body 12, one or more of the spacers 16 can be formed of a porous material to provide communication between the chambers 30. This communication can permit the pressures in each of the chambers 30 to reach an equilibrium. Alternatively, one or more of the spacers 16 can include channels, lumens 38 and/or a ridged external surface to permit the communication between chambers 30.

Figure 1F:
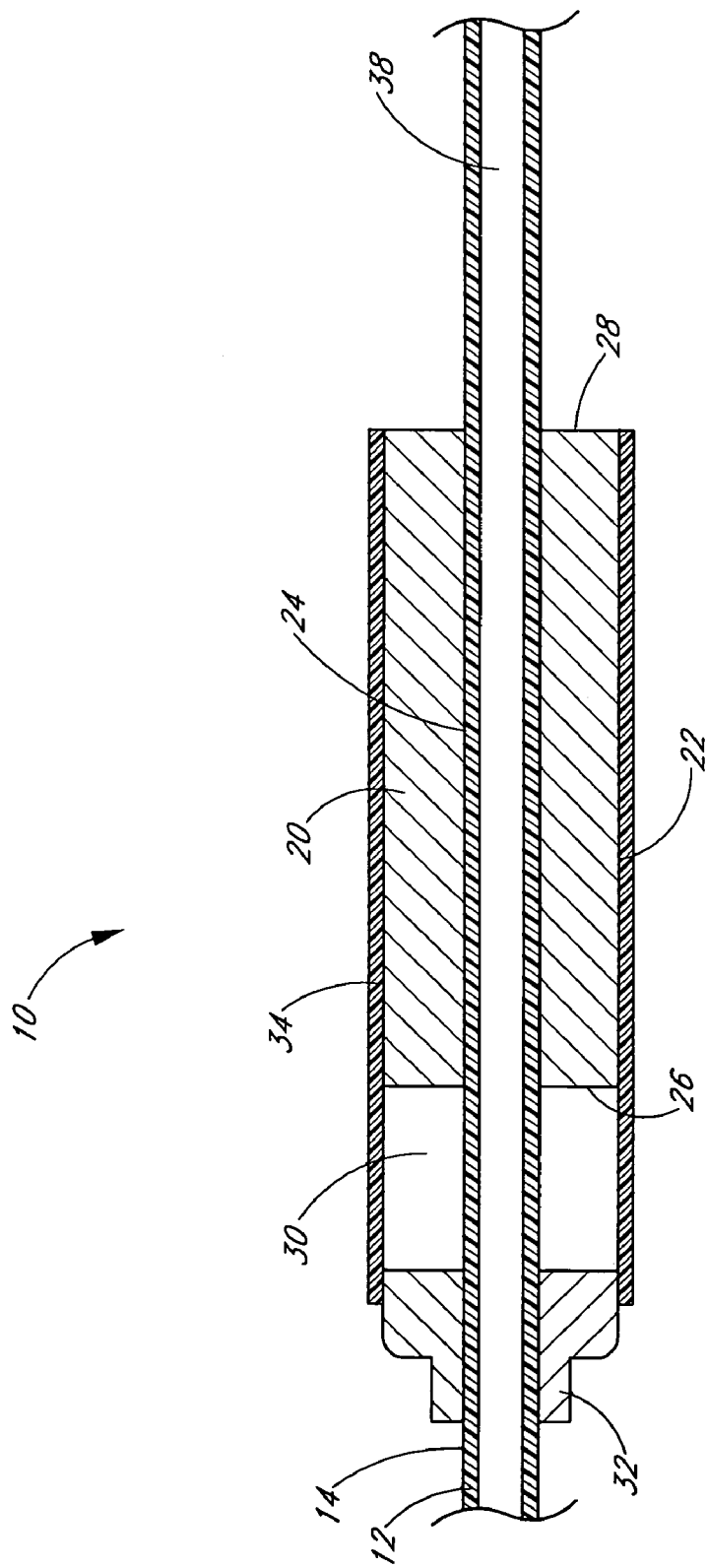

An embodiment of the ultrasound assembly 10 does not include a chamber 30 between the elongated body 12 and the internal side 24 of the ultrasound transducer 20 as illustrated in FIG. 1F. The ultrasound transducer 20 is positioned adjacent to the external surface 14 of the elongated body 12 such that a chamber 30 is not formed between the elongated body 12 and the ultrasound transducer 20. The ultrasound assembly 10 includes a collar 32 around the elongated body 12 in a spaced apart relationship from the ultrasound transducer 20 so as to form a chamber 30 adjacent to the first side of the ultrasound transducer 20.

Figure 1G:
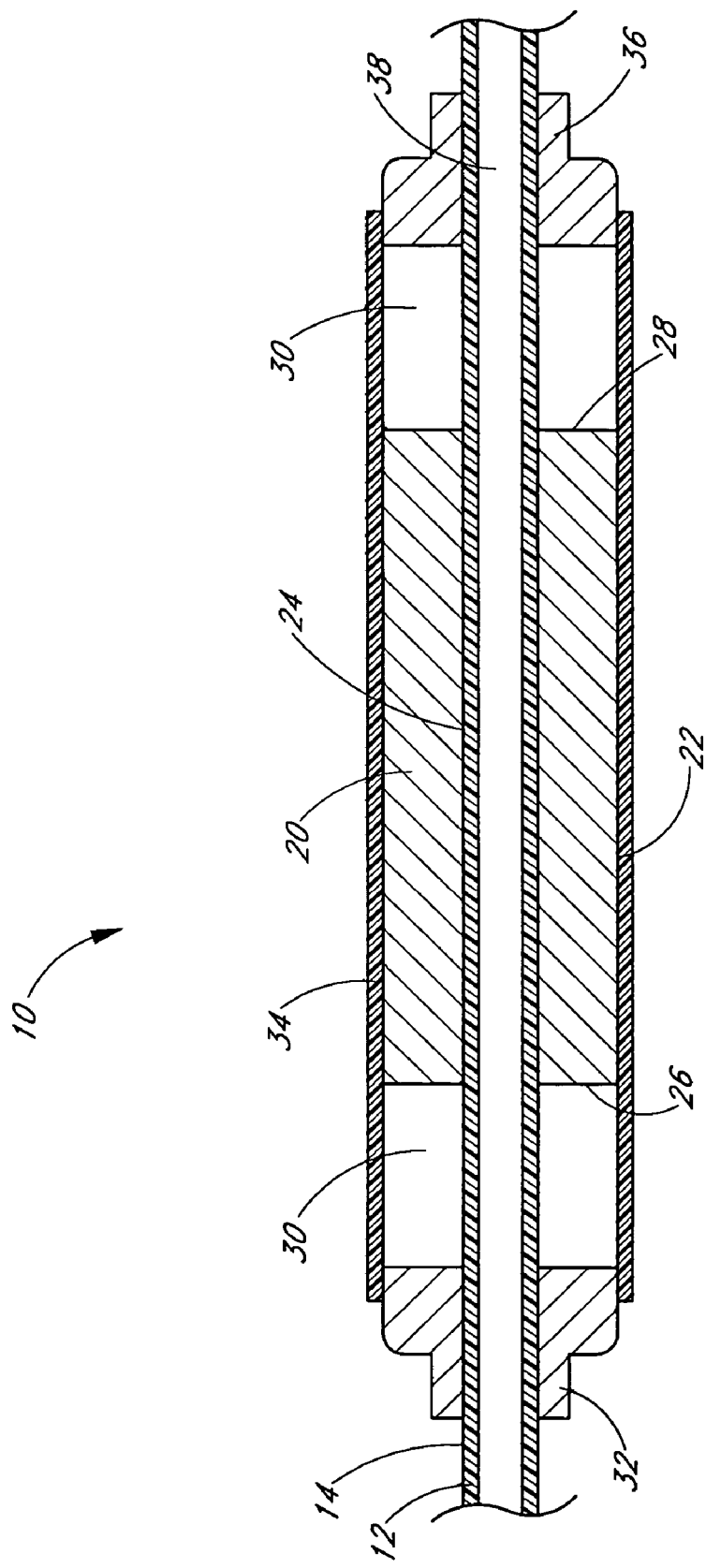
Figure 1H:
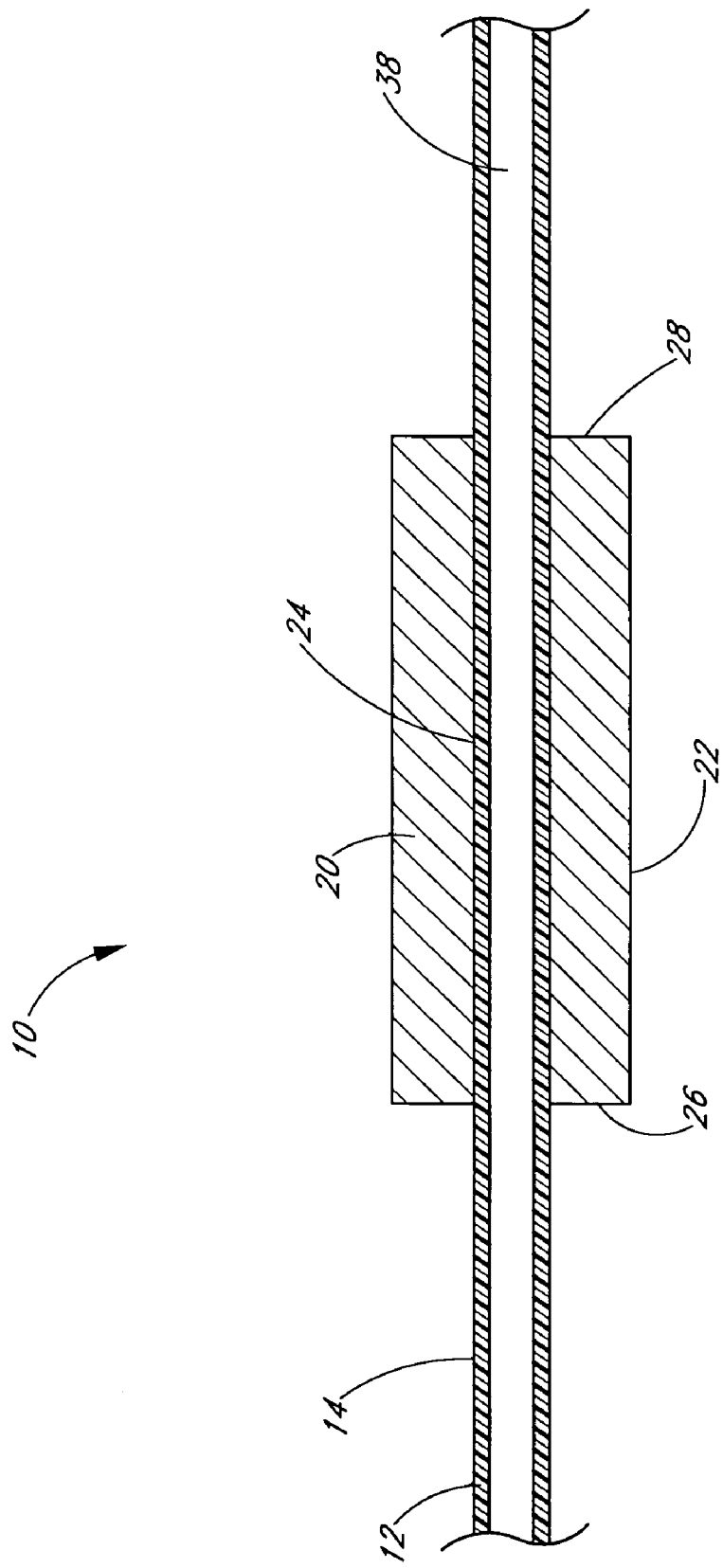
Figure 2A:
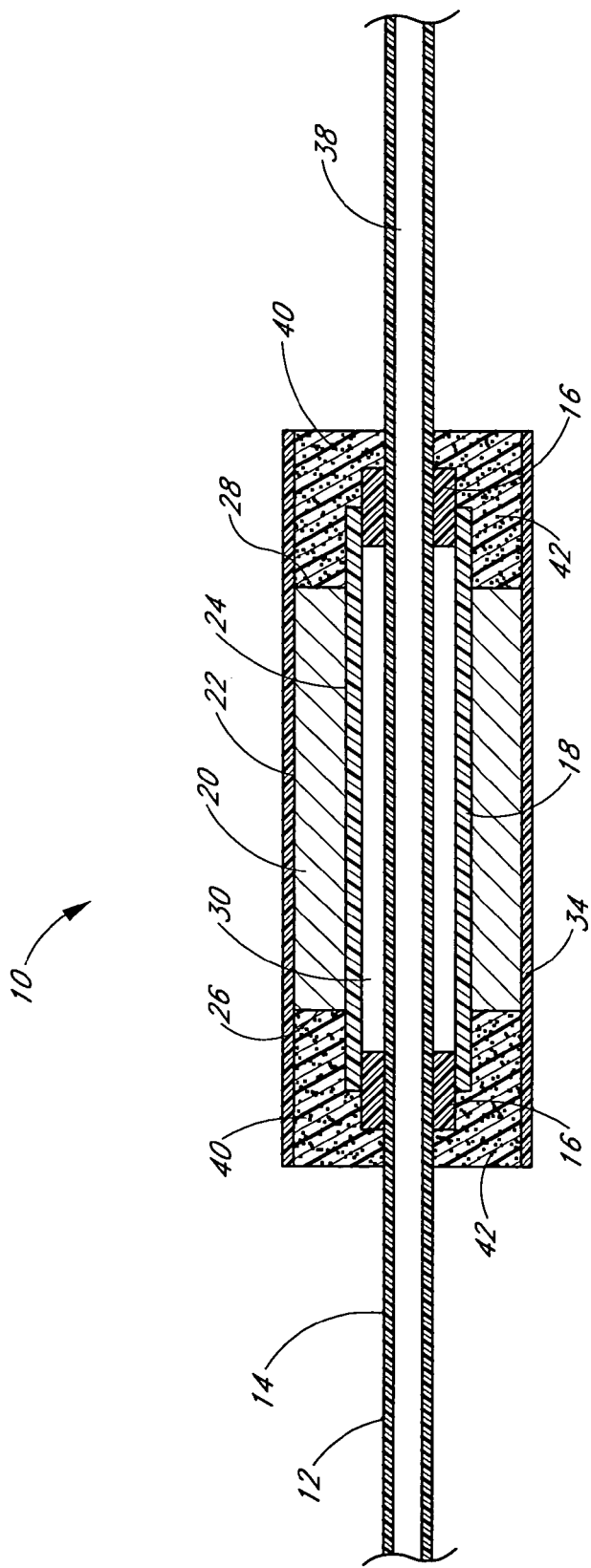
FIG. 2A-2D illustrate embodiments of ultrasound assemblies for use with a catheter according to the present invention. The ultrasound assemblies include a transducer sheath defining a reservoir at the end of the ultrasound assembly. The reservoir contains a binding medium.
Figure 2B:
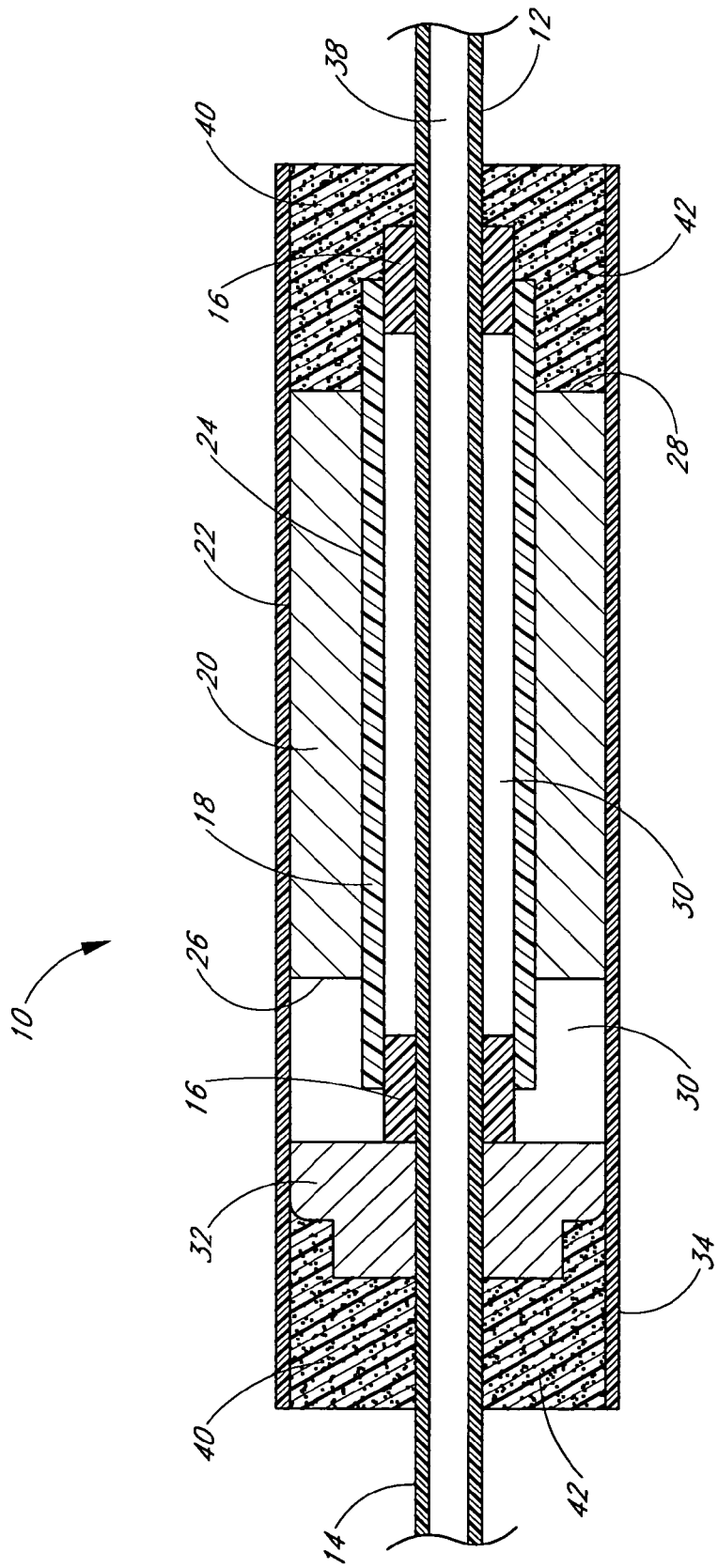
Figure 2C:
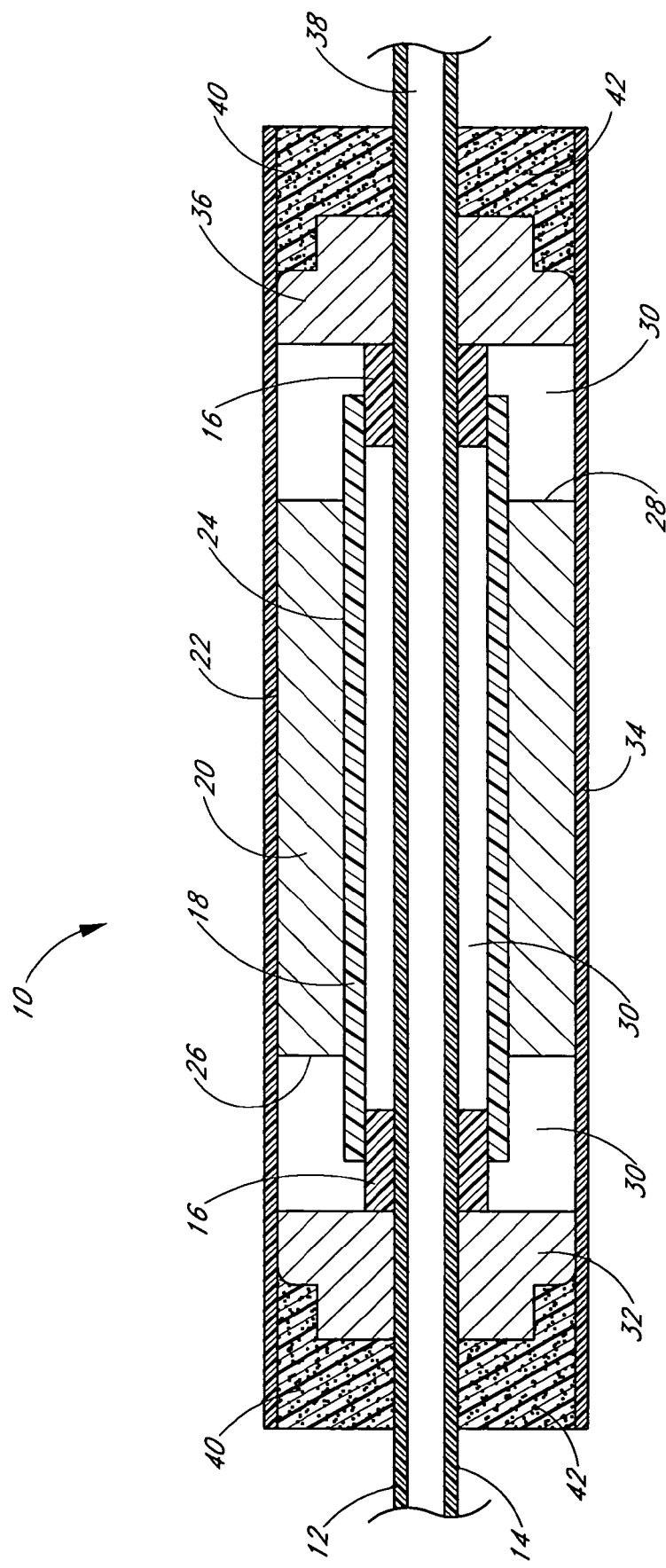
Figure 2D:
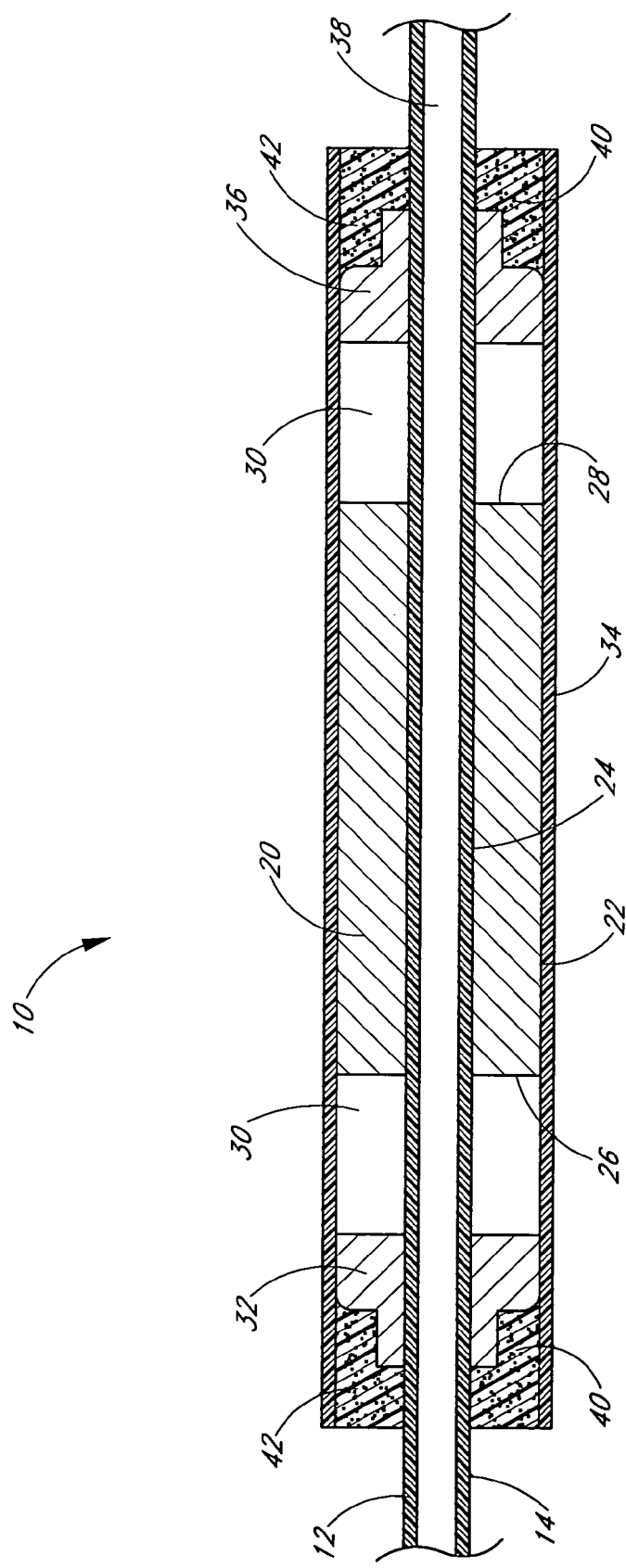

The ultrasound assembly 10 of FIG. 1F can also include a second chamber 30 adjacent to the second end 28 of the ultrasound transducer 20 as illustrated in FIG. 1G. The ultrasound assembly 10 includes a second collar 36 over the elongated body 12 in a spaced apart relationship from the ultrasound transducer 20. Accordingly a second chamber 30 is formed adjacent to the second side of the ultrasound transducer 20. As illustrated in FIG. 1H, an embodiment of the ultrasound assembly 10 does not include any chambers 30.

A utility lumen 38 extends through the elongated body 12. The utility lumen 38 can be sized to receive a guidewire, to deliver therapeutic media including drugs, medication, microbubbles and other compounds which provide a therapeutic effect. Although, the elongated body 12 is illustrated as having a single utility lumen 38, the elongated body 12 can include a plurality of lumens 38 or can be solid.

Each of the ultrasound assemblies 10 illustrated in FIGS. 1A-1H can have a transducer sheath 34 which extends past the first collar 32, the second collar 36 and/or past the ultrasound transducer 20. FIGS. 2A-2D illustrate such a transducer sheath 34 with a selection of the ultrasound assemblies 10 illustrated in FIGS. 1A-1H. The extension of the transducer sheath 34 past the collar 32 and/or past the ultrasound transducer 20 provides a reservoir 40 at the ends of the ultrasound assembly 10. The reservoir 40 can optionally contain a binding medium 42 such as an epoxy or adhesive. The binding medium 42 can serve to keep the ultrasound transducer 20 intact during the handling of the ultrasound assembly 10. Although FIGS. 2A-2D illustrate the transducer sheath 34 extending past the first collar 32, the second collar 36 and/or the ultrasound transducer 20 at both ends of the ultrasound assembly 10, the transducer sheath 34 can extending past a collar 32 and/or ultrasound transducer 20 at only one end of the ultrasound assembly 10.

Each ultrasound assembly 10 discussed and/or suggested above can include an assembly 10 sheath. FIG. 3A-3D illustrate a selection of the above ultrasound assemblies 10 including an assembly sheath 44 positioned over the ultrasound transducer 20. Suitable materials for the assembly sheath 44 include, but are not limited to polyimide, PTFE, and polyurethane. The assembly sheath 44 preferably has a thickness from 12-75 μm and more preferably from 25-50 μm.

Figure 3A:
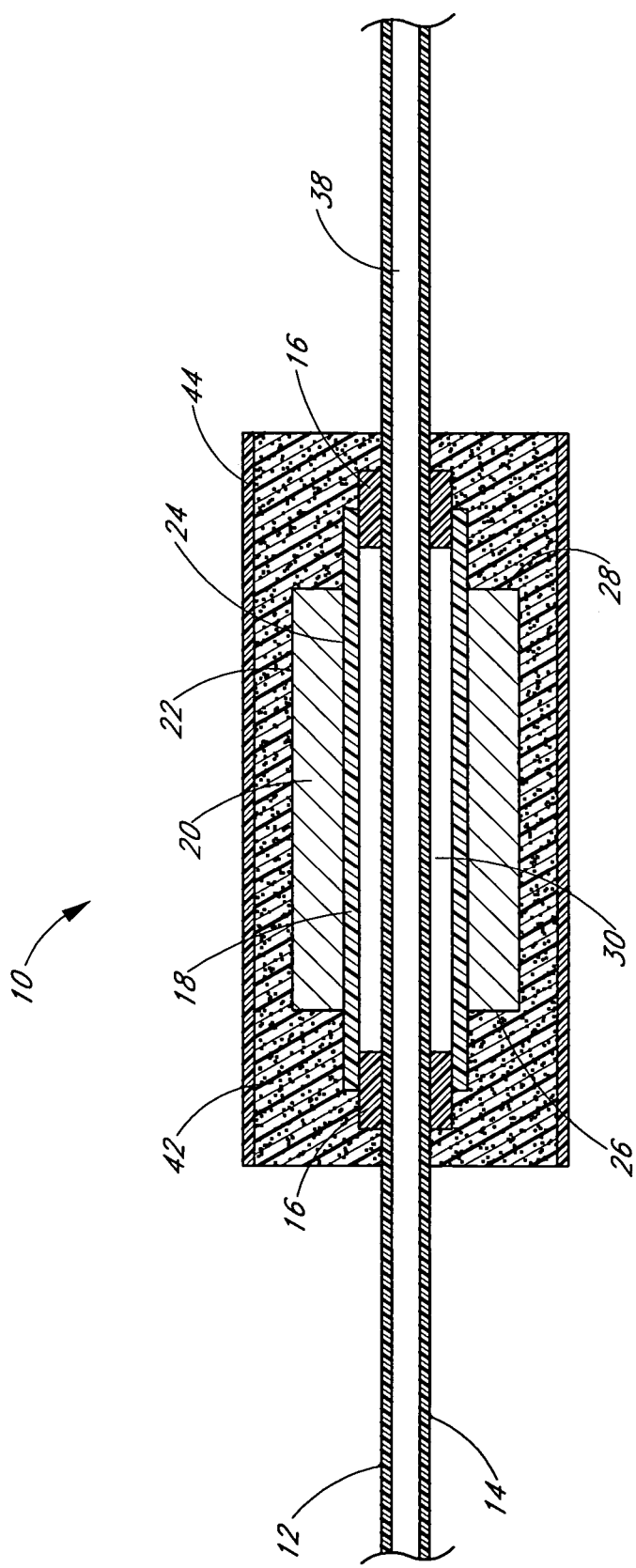
FIGS. 3A-3D illustrate embodiments of ultrasound assemblies for use with a catheter according to the present invention. The ultrasound assemblies include an assembly sheath positioned over an ultrasound transducer. A volume between the ultrasound transducer and the assembly sheath contains a binding medium.
Figure 3B:
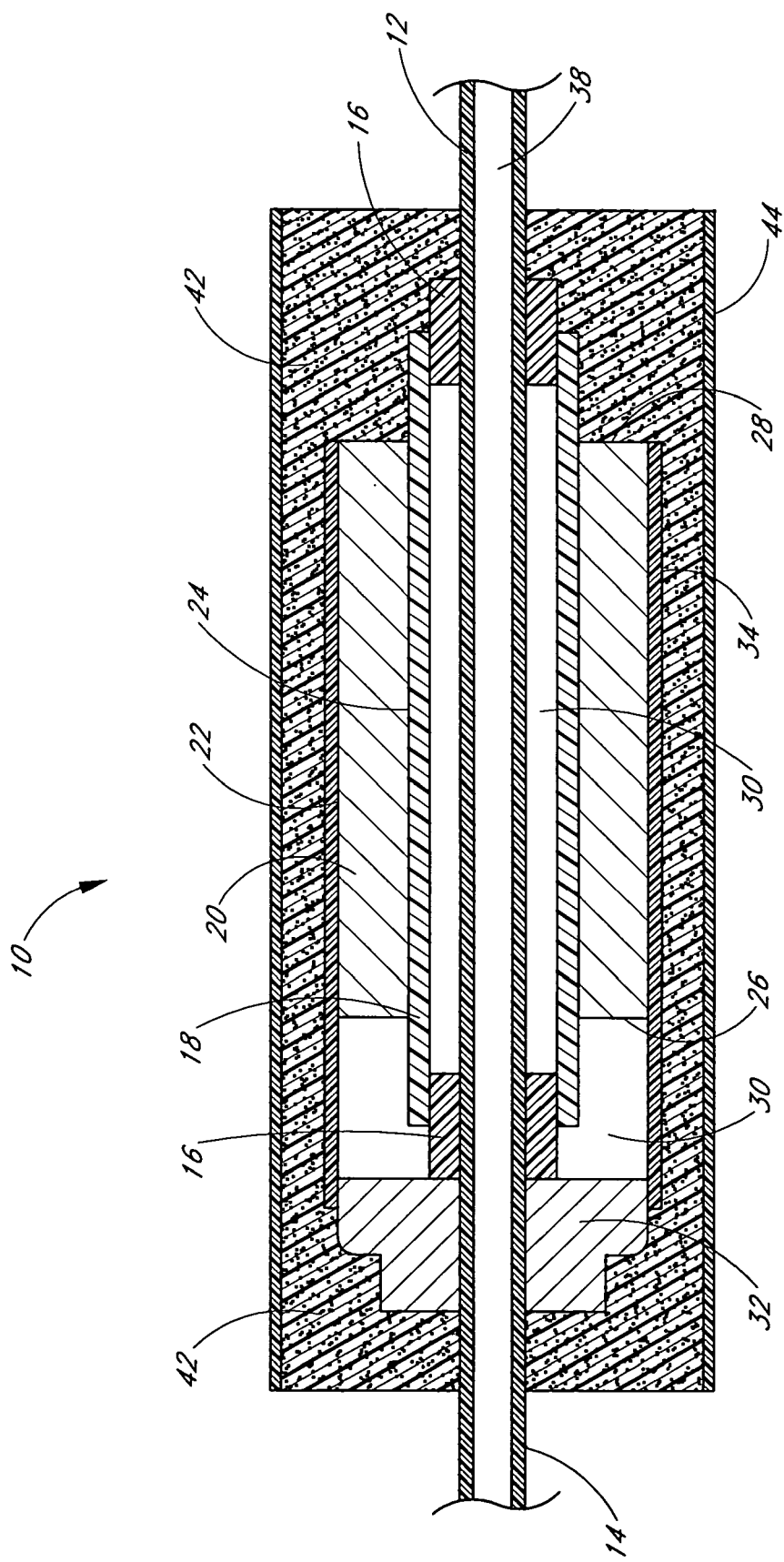
Figure 3C:
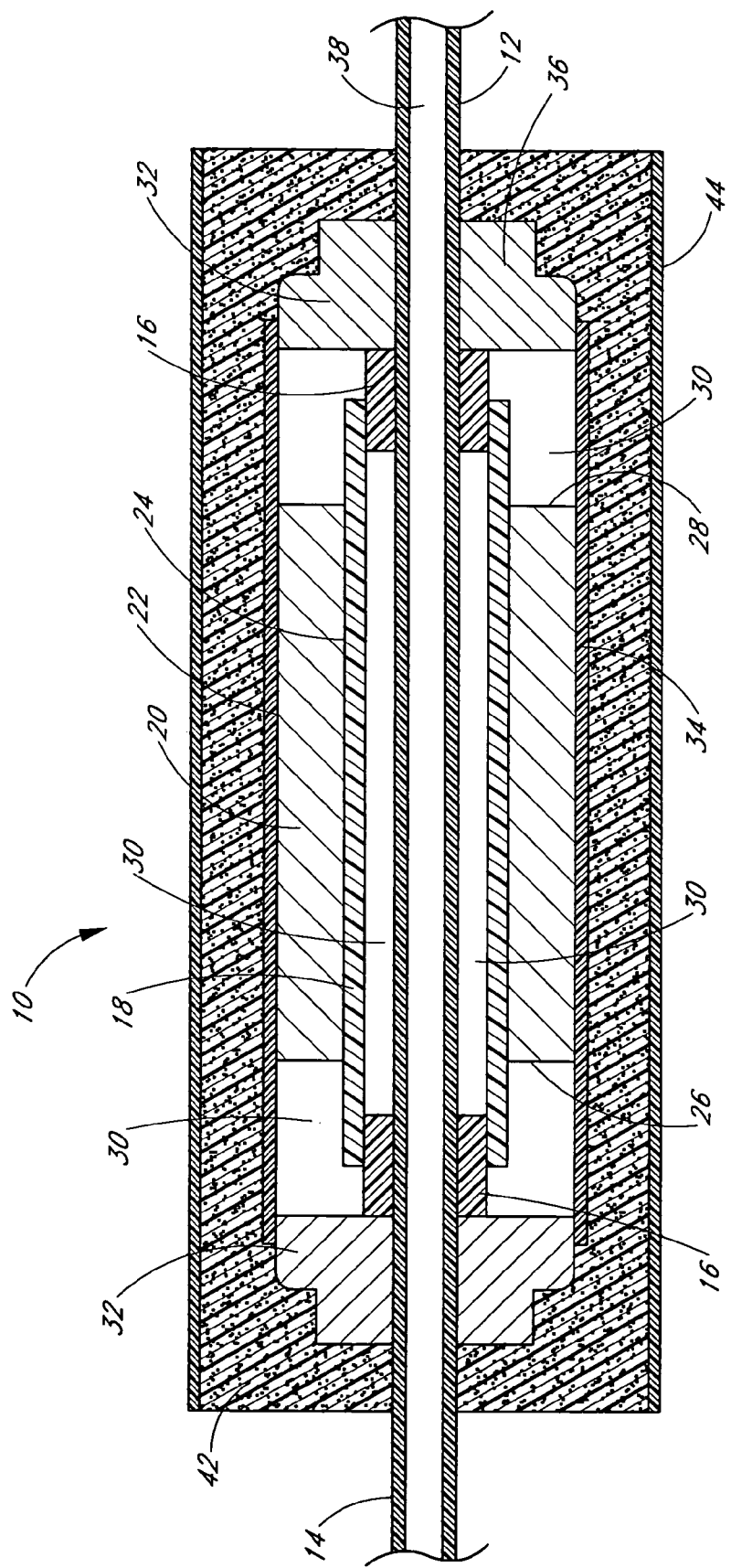
Figure 3D:
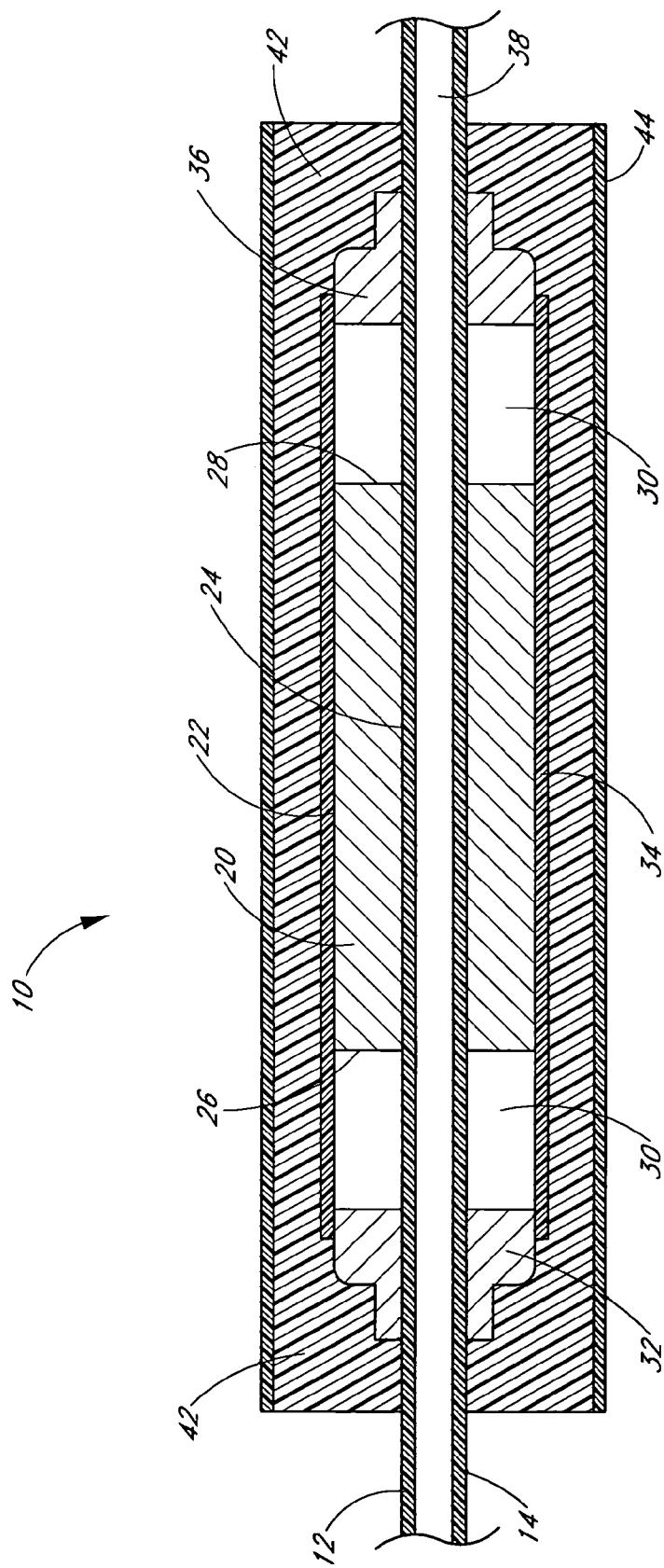

A volume between the assembly sheath 44 and the ultrasound transducer 20 can contain a binding medium 42 as illustrated in FIG. 3A. Further, when the ultrasound assembly 10 includes a transducer sheath 34, the volume between the ultrasound assembly 10 sheath and the transducer sheath 34 can contain the binding medium 42 as illustrated in FIGS. 3B-3D. The binding medium 42 can be a binding medium 42 which serves to keep the ultrasound transducer 20 intact during the handling of the ultrasound assembly 10.

Each of the ultrasound assemblies 10 illustrated above show the elongated body 12 extending outward from the ultrasound assembly 10. However, the elongated body 12 can be trimmed to provide an elongated body 12 which is flush with one or more sides of the elongated body 12. Additionally, a sensor such as a temperature sensor can be positioned in the binding medium 42 associated with any of the above ultrasound assemblies 10.

FIGS. 4A-4F illustrate various arrangements between the collars 32 and spacers 16 for use with the ultrasound assemblies 10 discussed above. FIG. 4A illustrates the collar 32 abutting the spacers 16. The collar 32 can be spaced apart from the spacers 16 as illustrated in FIG. 4B. In another embodiment, the collar 32 is sized to be positioned around the spacer 16 as illustrated in FIG. 4C. In yet another embodiment, the collar 32 is sized to be positioned around the member 18 as illustrated in FIG. 4D.

The collar 32 can be integral with the spacers 16 as illustrated in FIG. 4E. The spacer 16 has an L-shaped profile with a spacer region 46 positioned adjacent to the member 18 and a collar region 48 positioned adjacent to the transducer sheath 34. Accordingly, the raised edge serves to define a side of the chamber 30. When the collar 32 is integral with the spacer, the spacer 16 can include a seat 50 sized to receive an edge of the member 18 as illustrated in FIG. 4F.

Figure 5A:
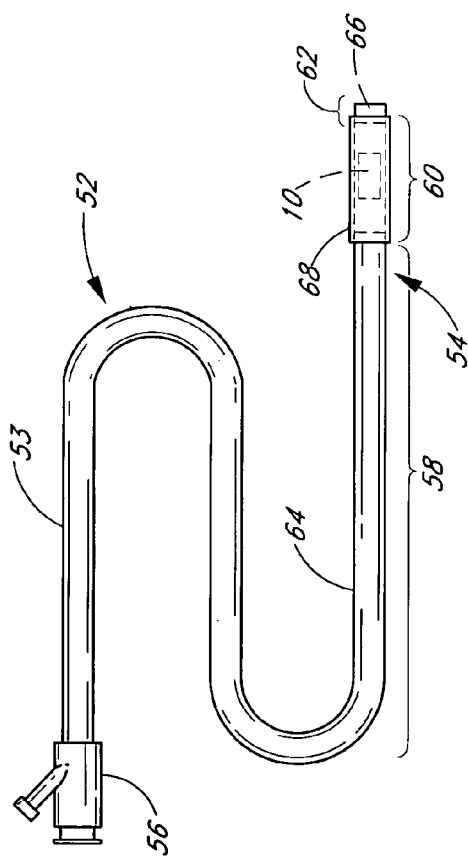
FIG. 5A illustrates a catheter incorporating an ultrasound assembly.
Figure 5B:
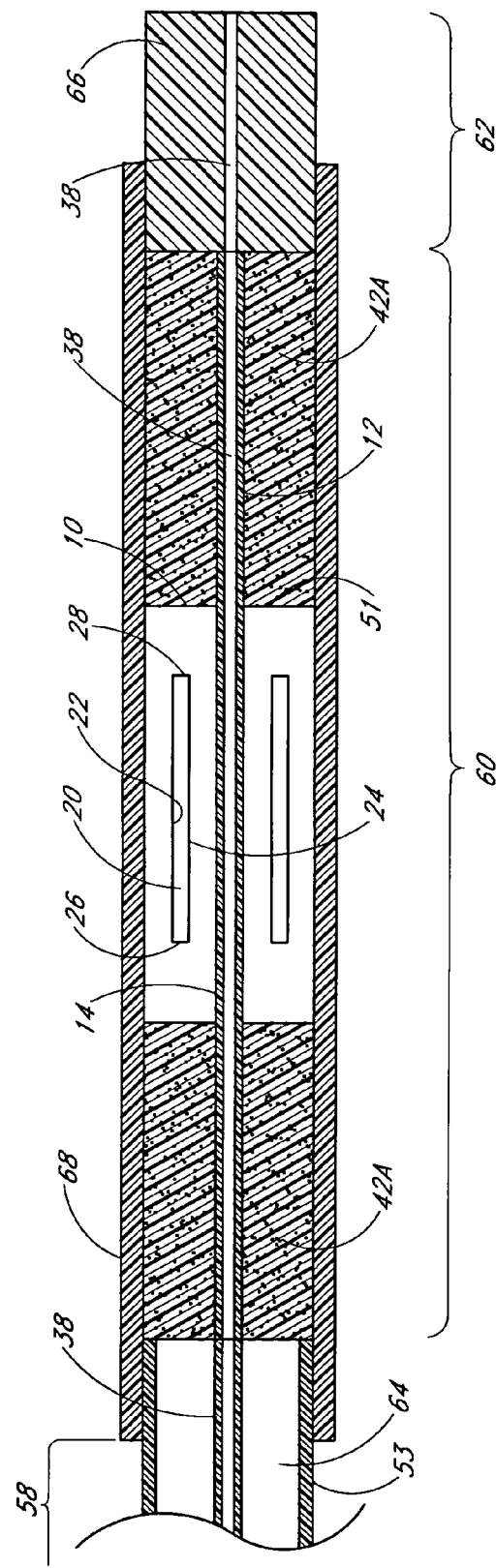
FIG. 5B illustrates catheter having a binding medium adjacent to the ends of the ultrasound transducer.

FIGS. 5A and 5B illustrate a catheter according to the present invention. The catheter can include any of the ultrasound assemblies 10 discussed or suggested above. As a result, the catheter is illustrated with a generalized representation of an ultrasound assembly 10. Specifically, an ultrasound assembly 10 is illustrated as an ultrasound transducer 20 over an elongated body 12. A box 51 over the ultrasound transducer 20 represents the remaining portions of each ultrasound assembly 10. For instance, the box 51 can represent the collars 32, spacers, members, chambers, binding media, etc. associated with an ultrasound assembly 10.

The catheter includes a catheter body 52 having an external surface 53, a distal portion 54 and a proximal portion 56. The catheter body 52 can include an extension region 58, an assembly region 60 and a terminal region 62. Lumens 38 within the extension region 58, assembly region 60 and terminal region 62 are aligned with one another to provide one or more lumens 38 extending through the entire catheter. These lumens 38 can be sized to receive a guidewire or for the delivery of a therapeutic agent such as a drug.

The extension region 58 includes an extension body 64 having one or more lumens 38. The one or more lumens 38 included in the extension body 64 have cross sectional dimensions approximating the cross section dimensions of the one or more utility lumens 38 of the elongated body 12. The extension body 64 can be used to add length to the catheter. Specifically, the extension body 64 can provide additional length beyond the length provided by the assembly region 60. Accordingly, the extension body 64 can be short or can be eliminated from the catheter body 52. Suitable materials for the extension body 64 include, but are not limited to, polyimide, silicone, and polyurethane.

The terminal region 62 is positioned at the distal tip of the catheter. The terminal region 62 includes a terminal body 66. The terminal body 66 can be solid or include one or more lumens 38 with cross sectional dimensions approximating the cross section dimensions of the one or more utility lumens 38 of the elongated body 12. Suitable materials for the terminal region 62 include, but are not limited to, polyimide, silicone, and polyurethane. The assembly region 60 is the region of the catheter body 52 including any of the ultrasound assemblies 10 discussed and/or suggested above.

A catheter sheath 68 is positioned over the extension region 58, the assembly region 60 and the terminal region 62 so as to define a portion of the external surface 53 of the catheter body 52. The catheter sheath 68 can serve to immobilize the extension region 58, the assembly region 60 and the terminal region 62 relative to one another. The catheter sheath 68 is optional and can be removed from the catheter body 52.

The volume between the ultrasound assembly 10 and the extension body 64 can contain a binding medium 42. Such binding media can serve to couple the extension region 58, the assembly region 60 and the terminal region 62 together. Suitable materials for the catheter sheath 68 include, but are not limited to polyethylene, polyurethane, and polyimide. The thickness of the catheter sheath 68 material is preferably 0.001" to 0.020", more preferably 0.004" to 0.010" and most preferably 0.006" to 0.008".

As illustrated in FIG. 5B, a first binding medium 42A can be positioned adjacent to the ends of the ultrasound transducer 20. Specifically, a volume between the extension body 64 and the ultrasound transducer 20 can contain the first binding medium 42A. Further, the volume between the terminal body 66 and the ultrasound transducer 20 can contain the first binding medium 42A.

Figure 5C:
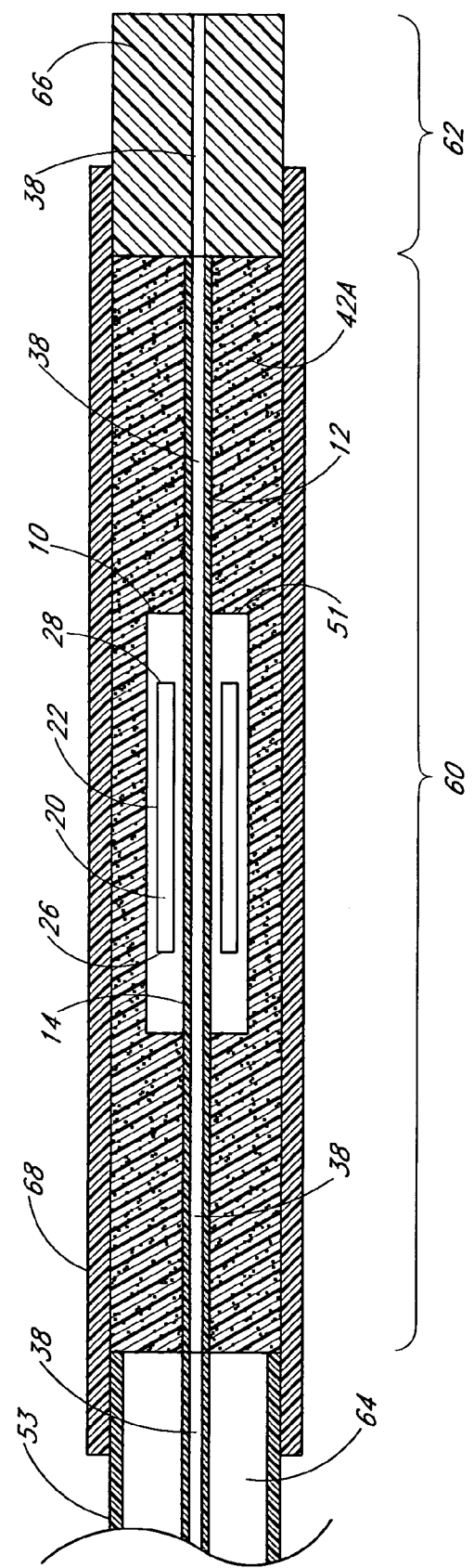
FIG. 5C illustrates a catheter having a binding medium adjacent to the external side of the ultrasound transducer.

The first binding medium 42A can also be positioned adjacent to the external side 22 of the ultrasound transducer 20 as illustrated in FIG. 5C. Specifically, the first binding medium 42A can be contained in a volume between the external side 22 of the ultrasound transducer 20 and the externals surface of the catheter body 52.

Figure 5D:
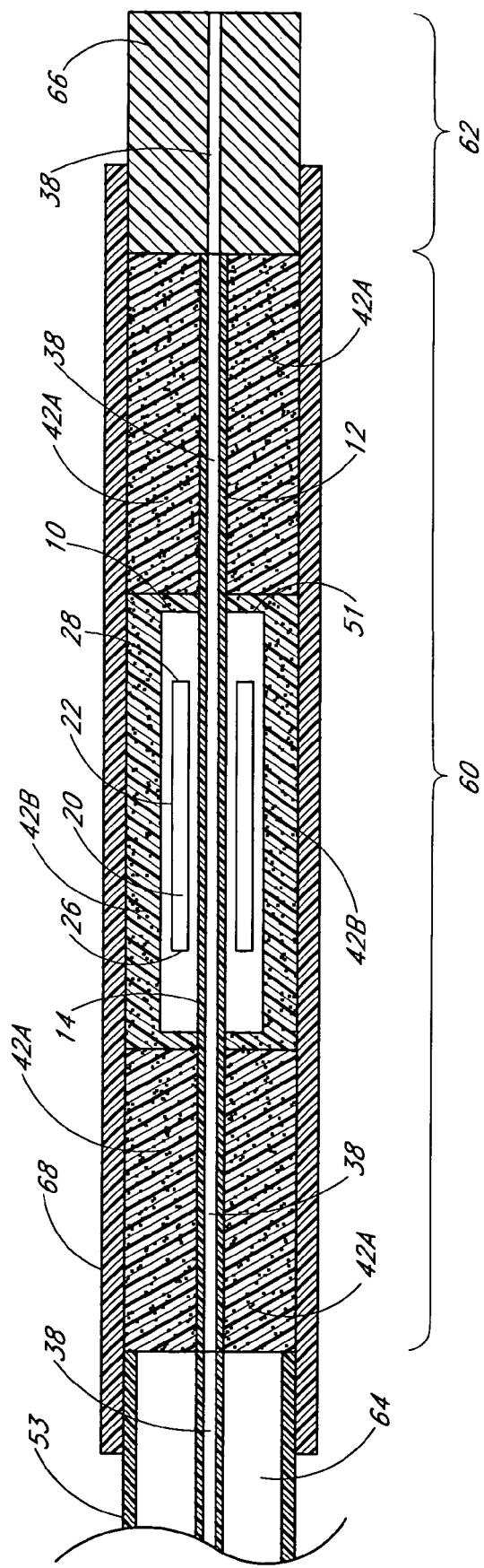
FIG. 5D illustrates a catheter having a binding medium adjacent to the ends of the ultrasound transducer and another binding medium adjacent to the external side of the ultrasound transducer.

As illustrated in FIG. 5D, a catheter can include a first binding medium 42A and a second binding medium 42B. The first binding medium 42A is adjacent to the ends of the ultrasound transducer 20 and the second binding medium 42B is adjacent to the external side 22 of the ultrasound transducer 20. Specifically, the second binding medium 42B can be contained in a volume between the external side 22 of the ultrasound transducer 20 and the external surface 53 of the catheter body 52. A portion of the second binding medium 42B is also illustrated as being adjacent to the ends of the ultrasound assembly 10 although the second binding medium 42B can be restricted to the volume adjacent to the external side 22 of the ultrasound transducer 20.

The first binding medium 42A and the second binding medium 42B can be the same or different. When the second binding medium 42B is different than the first binding medium 42A, the second binding medium 42B is preferably harder than the first binding medium 42A. A harder binding medium 42 typically transmits ultrasound energy more efficiently than a softer binding medium 42. As a result, the hardness of the second binding medium 42B can preserve the ultrasound transmitting efficiency of the catheter. Additionally, the softness of the first binding medium 42A provides the catheter with additional flexibility. As a result, the choices of the first and second binding media effect both the flexibility and the ultrasound transmission efficiency of the catheter.

The second binding medium 42B is preferably at least 2 times harder than the first binding medium 42A and more preferably from about 3 to about 5 times harder than the first binding medium 42A. The first binding medium 42A preferably has a hardness of at least about 10 Shore D, more preferably from about 15 to about 80 Shore D and most preferably from about 20 to about 40 Shore D. The second binding medium 42B preferably has a hardness of at least about 60 Shore D, more preferably from about 65 to about 120 Shore D and most preferably from about 80 to about 100 Shore D.

Figure 5E:
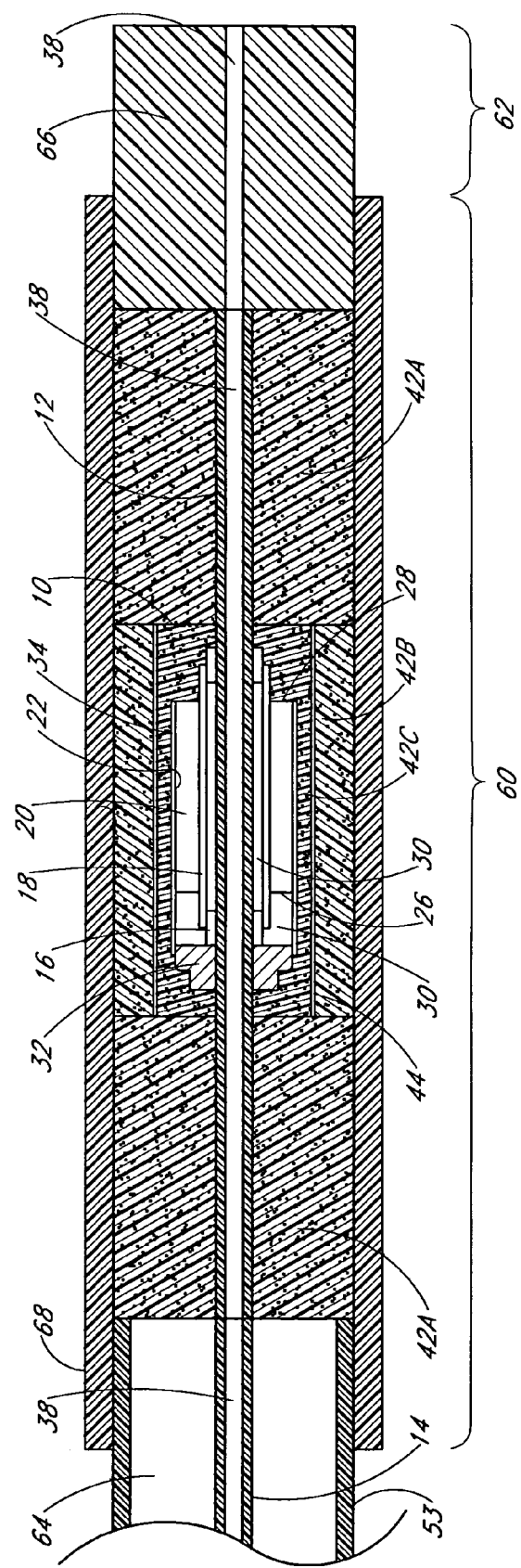
FIG. 5E illustrates a catheter having a binding medium adjacent to the ends of the ultrasound transducer and a second binding medium adjacent to the external surface of the catheter ultrasound transducer and a third binding medium adjacent to the ultrasound transducer.

As described above, any of the ultrasound assemblies 10 described and/or suggested above can be included in a catheter according to the present invention. FIG. 5E illustrates a particular example of a catheter including an assembly sheath 44 over the ultrasound transducer 20. Specifically, FIG. 5B illustrates the catheter including the ultrasound assembly 10 of FIG. 2B. The ultrasound assembly 10 includes a chamber 30 adjacent to a first end 26 of the ultrasound transducer 20. The chamber 30 is positioned proximally relative to the ultrasound transducer 20. The ultrasound assembly 10 includes another chamber 30 between the ultrasound transducer 20 and the external surface 14 of the elongated body 12. Each chamber 30 contains a low acoustic impedance medium. As a result, this embodiment of the catheter efficiently transmits ultrasound energy in the distal direction.

The catheter of FIG. 5E includes a first binding medium 42A, a second binding medium 42B and a third binding medium 42C. The first binding medium 42A is adjacent to the ends of the ultrasound transducer 20 and the second binding medium 42B is contained in a volume between the assembly sheath 44 and the external surface 53 of the catheter body 52. The third binding medium 42C is adjacent to the external side 22 of the ultrasound transducer 20. Specifically, a volume between the ultrasound transducer 20 and the assembly sheath 44 includes the third binding medium 42C.

Two or more of the first, second and third binding media can be the same or they can all be different. In a preferred embodiment, the first and second binding media are the same while the third binding medium 42C transmits is harder than the first and second binding media. Accordingly, when the first and second binding media are the same, the third binding media is preferably harder than the first binding medium 42A. Preferably, the first binding medium 42A is also more flexible than the third binding medium 42C. Further, the third binding medium 42C is preferably at least 2 times harder than the first binding medium 42A and more preferably from about 3 to about 5 times harder than the first binding medium 42A. Additionally, the first binding medium 42C preferably has a hardness of at least about 10 Shore D, more preferably from about 15 to about 80 Shore D and most preferably from about 20 to about 40 Shore D. The third binding medium 42B preferably has a hardness of at least about 60 Shore D, more preferably from about 65 to about 120 Shore D and most preferably from about 80 to about 100 Shore D. In another preferred embodiment, the second and third binding media are each harder than the first binding medium 42A. In another preferred embodiment, the second and third binding media are the same and are harder than the first binding medium 42A.

Figure 5F:
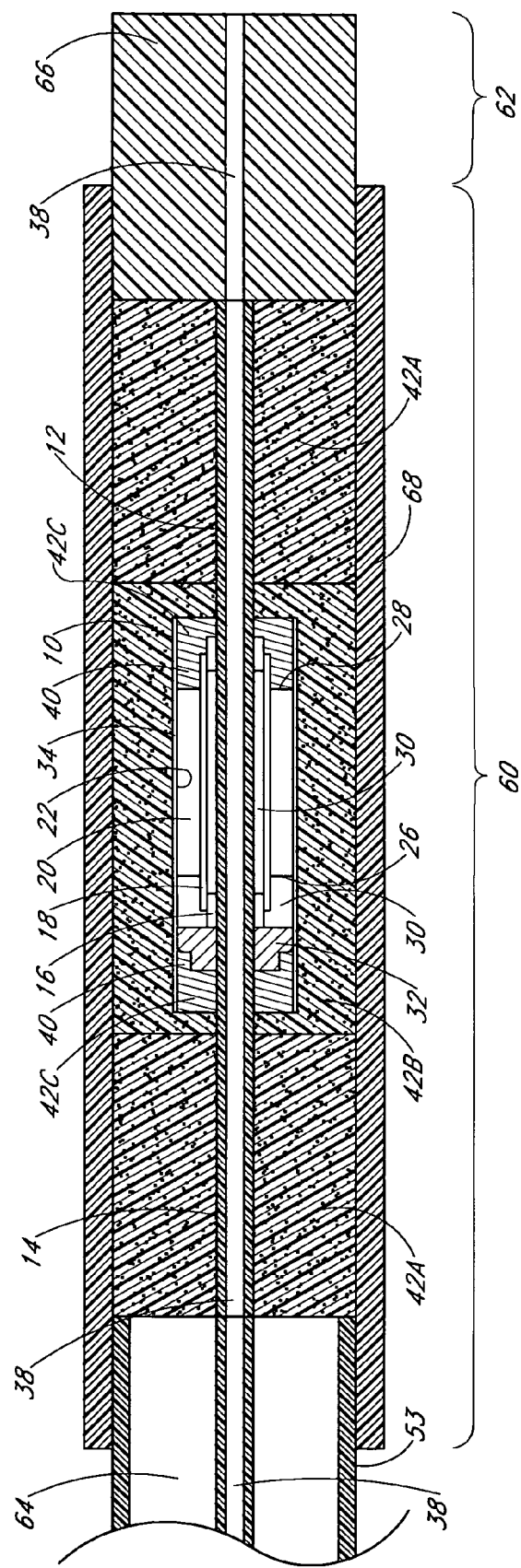
FIG. 5F illustrates a catheter having a binding medium adjacent to the ends of the ultrasound transducer, a second binding medium adjacent to the external side of the ultrasound transducer and a third binding medium positioned in reservoirs at the ends of the ultrasound assembly.

FIG. 5F illustrates a particular example of a catheter having a transducer sheath 34 extending beyond the collar 32 and the ultrasound transducer 20 to form reservoirs 40 at the end of the ultrasound assembly 10. The catheter includes a first binding medium 42A, a second binding medium 42B and a third binding medium 42C. The first binding medium 42A is adjacent to the ends of the ultrasound transducer 20 and the second binding medium 42B is adjacent to the external side 22 of the ultrasound transducer 20. Reservoirs 40 formed adjacent to the ends of the ultrasound transducer 20 contain the third binding medium 42C.

Two or more of the first, second and third binding media can be the same or they can all be different. The second binding medium 42B preferably transmits ultrasound energy more efficiently than the first binding medium 42A. Further, the first binding medium 42A is preferably more flexible than the second binding medium 42B. The first and second binding media preferably have the hardness relationships and levels described with respect to the first and second binding media of FIG. 5D. In a preferred embodiment, the first and third binding media are the same.

Figure 6A:
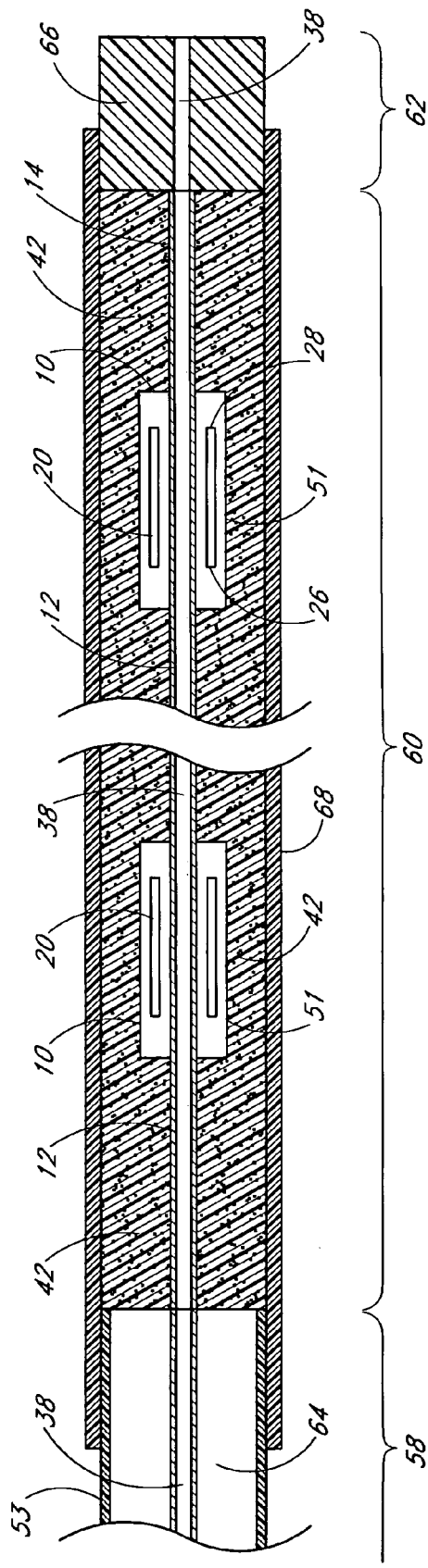
FIGS. 6A-6C illustrate embodiments of a catheter having a plurality of ultrasound assemblies according to the present invention.
Figure 6B:
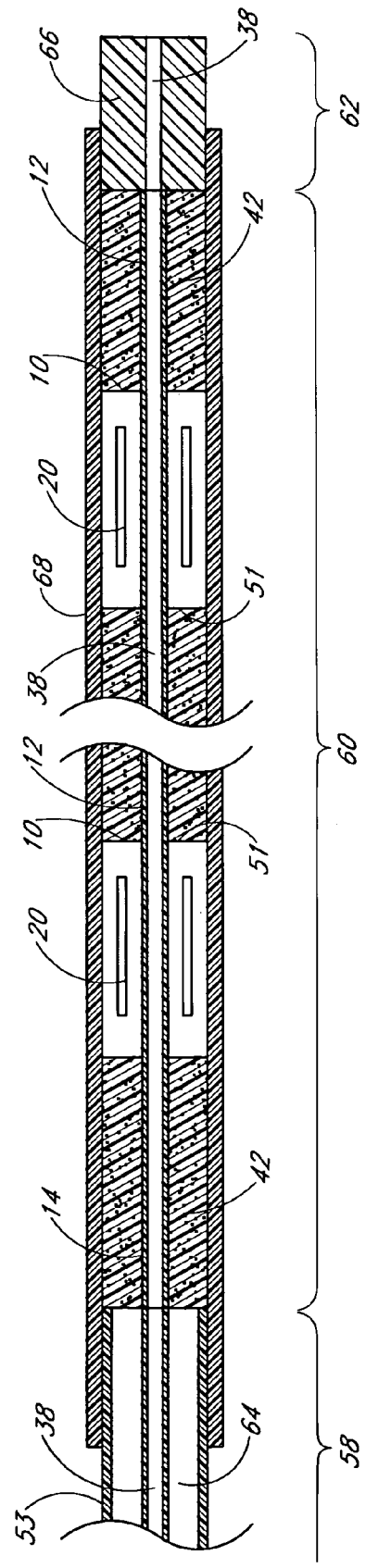

The catheter can include two or more ultrasound assemblies 10 as illustrated in FIGS. 6A and 6B. FIG. 6A illustrates the ultrasound assembly 10 in contact with the catheter sheath 68 while FIG. 6B illustrates the ultrasound assemblies 10 spaced apart from the catheter sheath 68. The ultrasound assemblies 10 can share the same elongated body 12 and/or different ultrasound assemblies 10 can include different elongated bodies 12. When the ultrasound assemblies 10 are formed with different elongated bodies 12, the different elongated bodies 12 can be aligned with one another during assembly of the catheter.

Figure 6C:
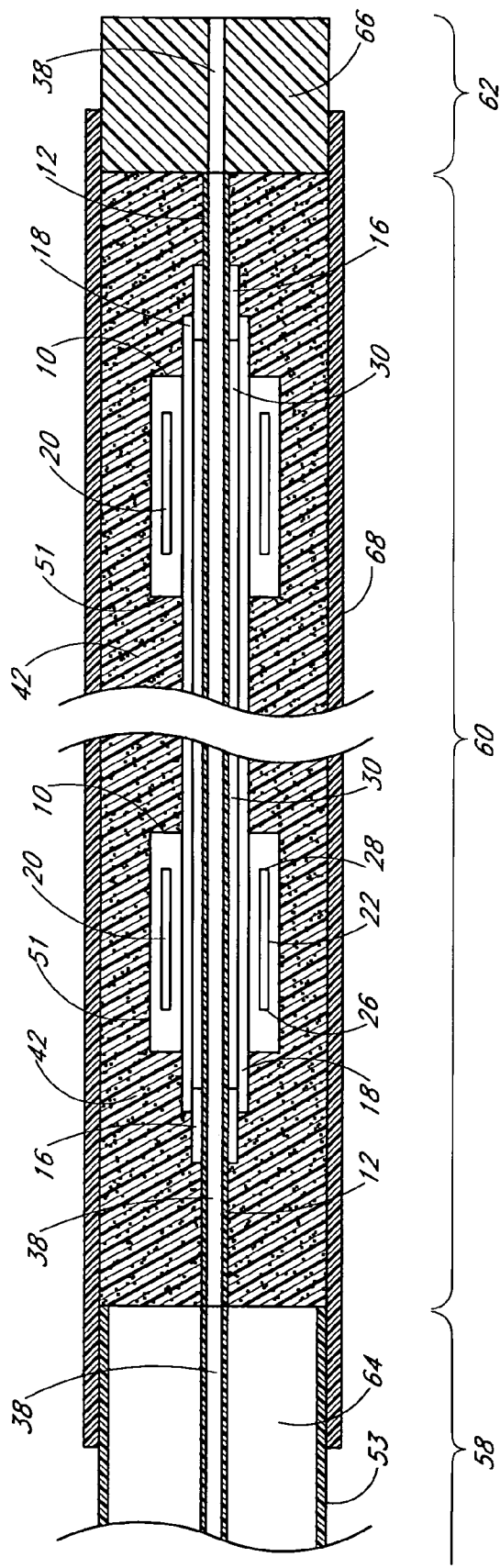

Two or more ultrasound assemblies 10 can share a member 18 as illustrated in FIG. 6C. Each of the ultrasound assemblies 10 is positioned over the same member 18. As a result, the member 18 partially defines a chamber 30 between each of the ultrasound transducers 20 and the elongated body 12. When different ultrasound transducers 20 share a member 18, spacers 16 can be optionally positioned between the ultrasound assemblies 10. As a result, a single member 18 can be positioned over at least a portion of three or more spacers 16.

As illustrated in FIGS. 6A and 6B, when the catheter includes a plurality of ultrasound transducers 20, a first binding medium 42A can be positioned adjacent to the ends of the ultrasound transducers 20. Specifically, the first binding medium 42A can be contained in a volume between an ultrasound transducer 20 and an extension body 64, a volume between adjacent ultrasound transducer 20, and/or a volume between an ultrasound transducer 20 and a terminal body 66.

As illustrated in FIG. 6C, a catheter including a plurality of ultrasound assemblies 10 can also include a second binding medium 42B adjacent to the external side 22 of the ultrasound transducers 20. Specifically, the second binding medium 42B can be contained in a volume between the external side 22 of the ultrasound transducer 20 and the external surface 53 of the catheter body 52. As described with respect to FIG. 5D, the first and second binding media can be the same or different and the second binding medium 42B is preferably harder than the first binding medium 42A. As described with respect to FIG. 5E-5F, the inclusion of specific ultrasound assembly 10 embodiments can result in the catheter including additional binding media. When the catheter includes an additional binding media adjacent to the external side 22 of the ultrasound transducers 20 (i.e. FIG. 5E), that binding media is preferably at least as hard as the first and second binding media.

Figure 7A:
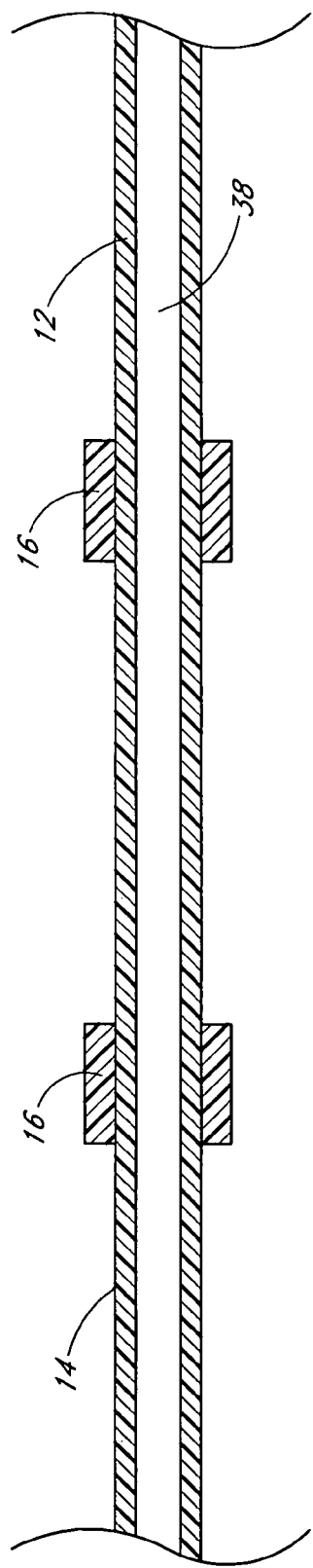
FIGS. 7A-7E illustrate a method for forming ultrasound assemblies according to the present invention.
Figure 7B:
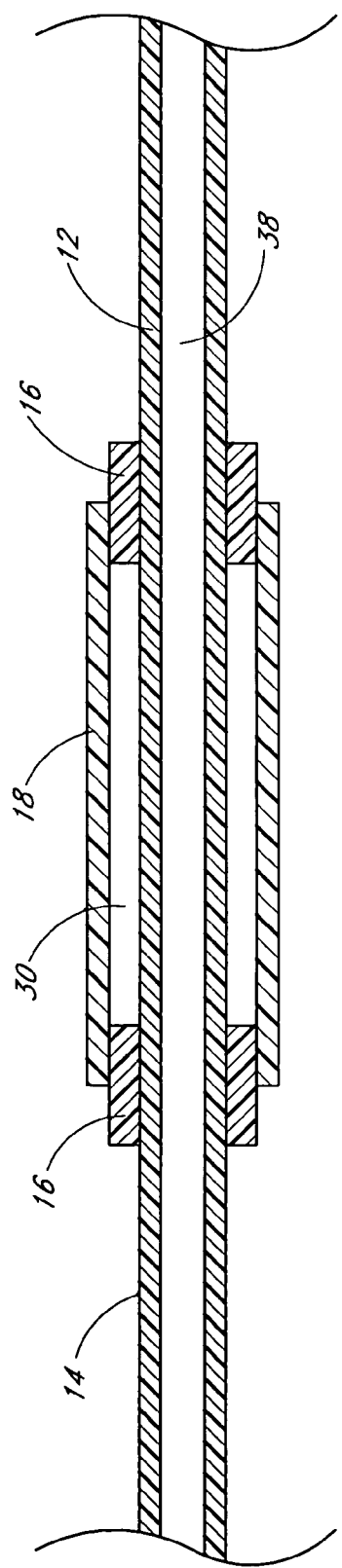

FIGS. 7A-7E illustrate a method for fabricating ultrasound assemblies 10 according to the present invention. In FIG. 7A, spacers 16 are positioned over an elongated body 12. The spacers 16 can optionally be adhesively attached to the elongated body 12 with compounds such as epoxy. FIG. 7B illustrates a member 18 positioned over the spacers 16. The positioning of the member 18 forms a chamber 30 between the member 18 and the elongated body 12. The member 18 can optionally be adhesively attached to the spacers 16 with compounds such as epoxy.

Figure 7C:
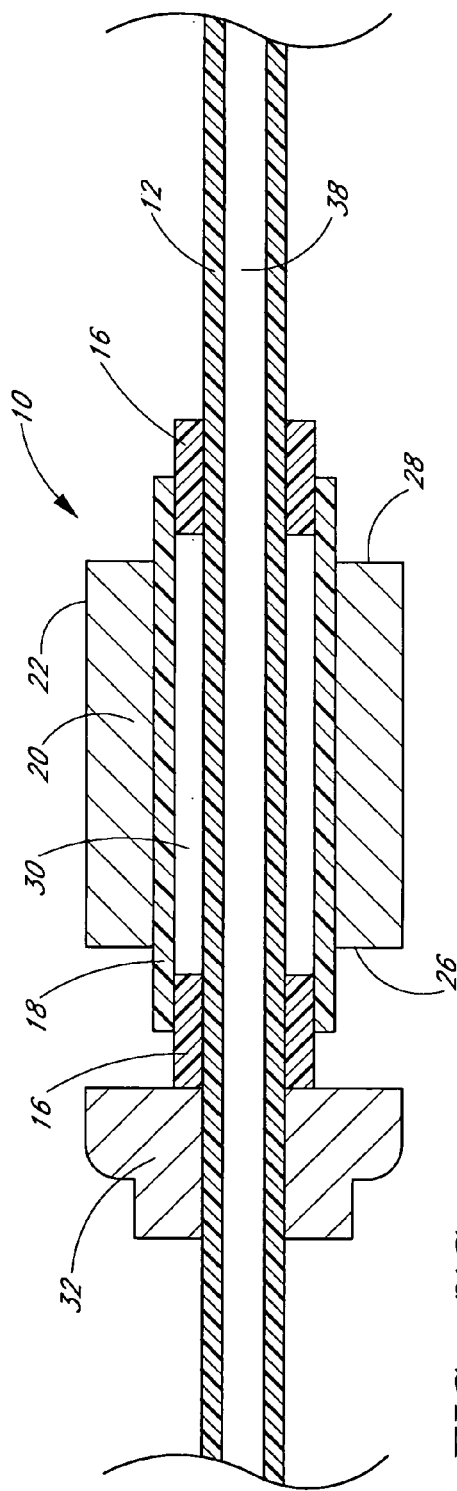
Figure 7D:
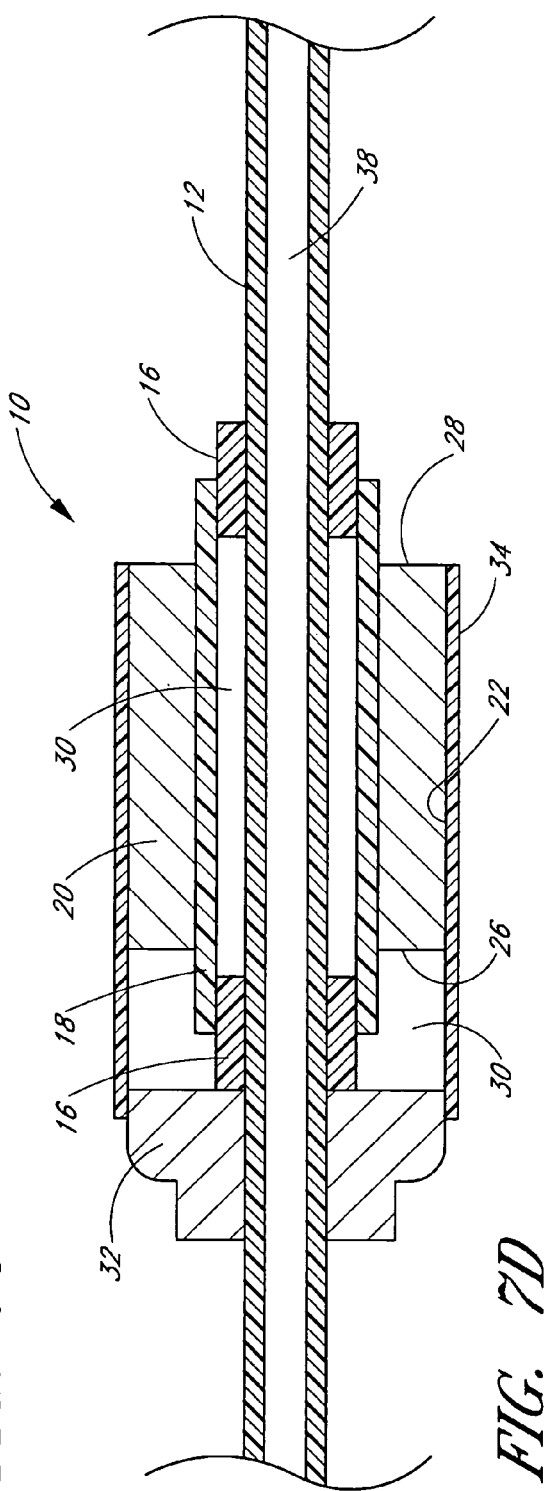

In FIG. 7C an ultrasound transducer 20 is positioned over the member 18 to form the ultrasound assembly 10 of FIG. 1A. The ultrasound transducer 20 can optionally be adhesively attached to the member 18 with compounds such as epoxy. A collar 32 is also positioned over the elongated body 12 and can be attached to the elongated body 12 with compounds such as epoxy. FIG. 7D illustrates a transducer sheath 34 positioned over the collar 32 to form the ultrasound assembly 10 of FIG. 2B. The transducer sheath 34 forms a chamber 30 adjacent to the ultrasound transducer 20.

Figure 7E:
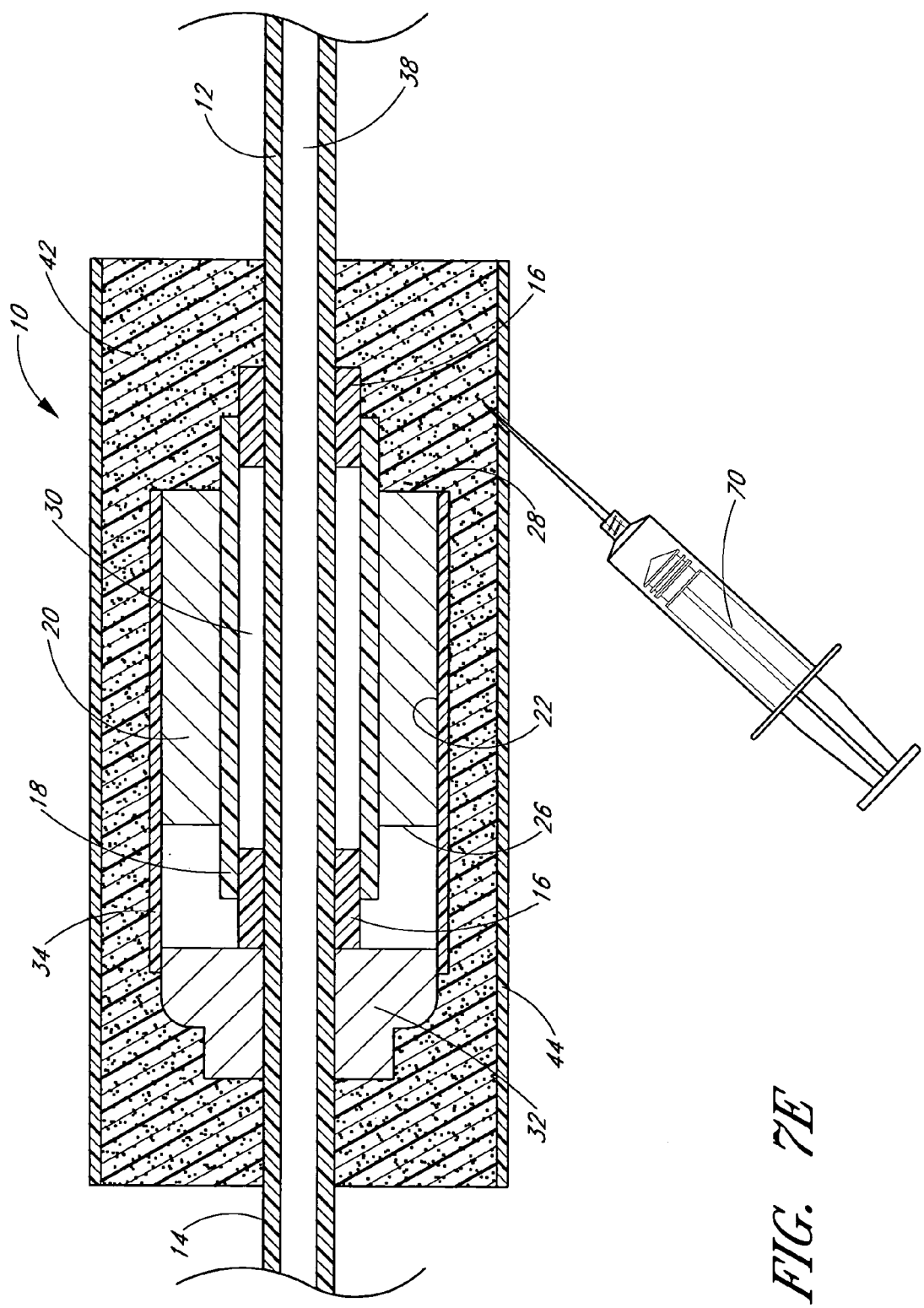

In FIG. 7E an assembly sheath 44 is positioned over the transducer sheath 34 of the ultrasound assembly 10 illustrated in FIG. 7D. A binding medium 42 precursor is delivered adjacent to the external side 22 of the ultrasound transducer 20. Specifically, the binding medium 42 precursor is delivered into a volume between the transducer sheath 34 and the assembly sheath 44. The binding medium 42 can be delivered into the volume using an injection device such as a hypodermic needle 70. The binding medium 42 can solidify to provide the ultrasound assembly 10 of FIG. 3B. Suitable mechanisms for solidification include, but are not limited to, setting, cooling and curing.

FIGS. 8A-8D illustrate method for forming ultrasound assemblies 10 when the collar 32 is integral with the spacers 16. FIG. 8A illustrates a spacer 16 positioned over an elongated body 12. In FIG. 8B a member 18 is positioned over the spacer 16 and an ultrasound transducer 20 is positioned over the member 18. In FIG. 8C a second spacer 16 is positioned over the elongated body 12 and moved toward the original spacer 16 until a portion of the spacer 16 is positioned between the member 18 and the elongated body 12. As a result, a chamber 30 is formed between the member 18 and the elongated body 12. In FIG. 8D a transducer sheath 34 is positioned over the spacers 16 and the ultrasound transducer 20 to form the ultrasound assembly 10 of FIG. 3C having collars 32 which are integral with the spacers 16.

Figure 9A:
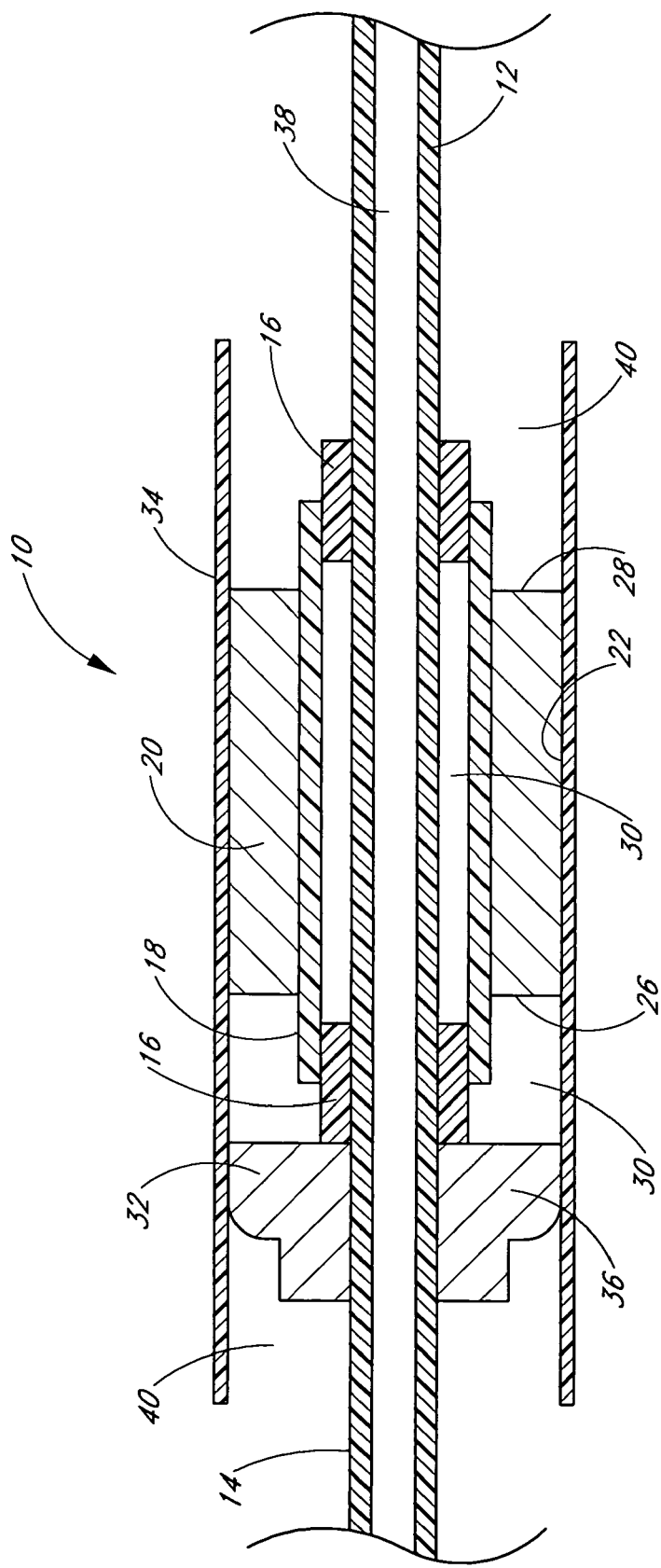
FIG. 9A illustrates a method for forming an ultrasound assembly having a transducer sheath extending beyond the ultrasound transducer and beyond a collar so as to form reservoirs adjacent to the ends of the ultrasound transducer.
Figure 9B:
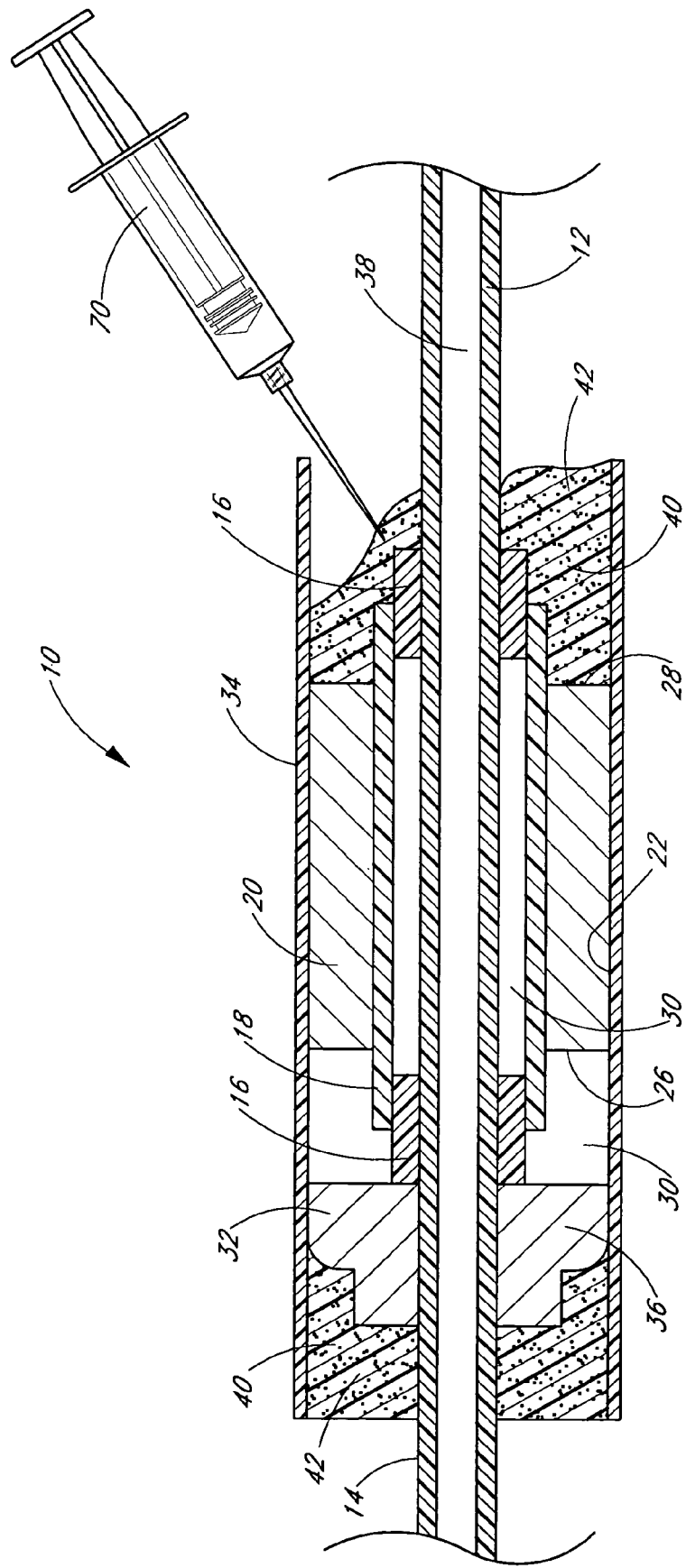
FIG. 9B illustrates delivery of a binding medium into a reservoir at an end of the ultrasound assembly.

FIGS. 9A-9B illustrate an adaptation of the method illustrated in FIGS. 7A-7E to form an ultrasound assembly 10 having a transducer sheath 34 which extends past a first collar 32, a second collar 36 and/or past the ultrasound transducer 20 as discussed with respect to FIGS. 2A-2D. FIG. 9A illustrates a transducer sheath 34 positioned over the collar 32 and ultrasound transducer 20 of FIG. 7C. The ultrasound transducer 20 extends past the collar 32 and the ultrasound transducer 20 to form reservoirs 40 adjacent to the ends of the ultrasound transducer 20. FIG. 9B illustrates a binding medium 42 precursor being delivered into the reservoirs 40 to provide the ultrasound assembly 10 illustrated in FIG. 2B.

The methods described in FIGS. 7A-9B can be used to provide an elongated body 12 having a plurality of ultrasound assemblies 10. Each ultrasound assembly 10 can be concurrently formed on the elongated body 12 or they can be sequentially formed on the elongated body 12. Alternatively, a portion of each ultrasound assembly 10 can be formed concurrently while the remaining portions of the ultrasound assemblies 10 are formed sequentially. For instance, in FIG. 6C, the chamber 30 between each ultrasound transducer 20 and the external surface 14 of the elongated body 12 can be formed concurrently while the remaining portions of the ultrasound assemblies 10 are formed sequentially.

Figure 10A:
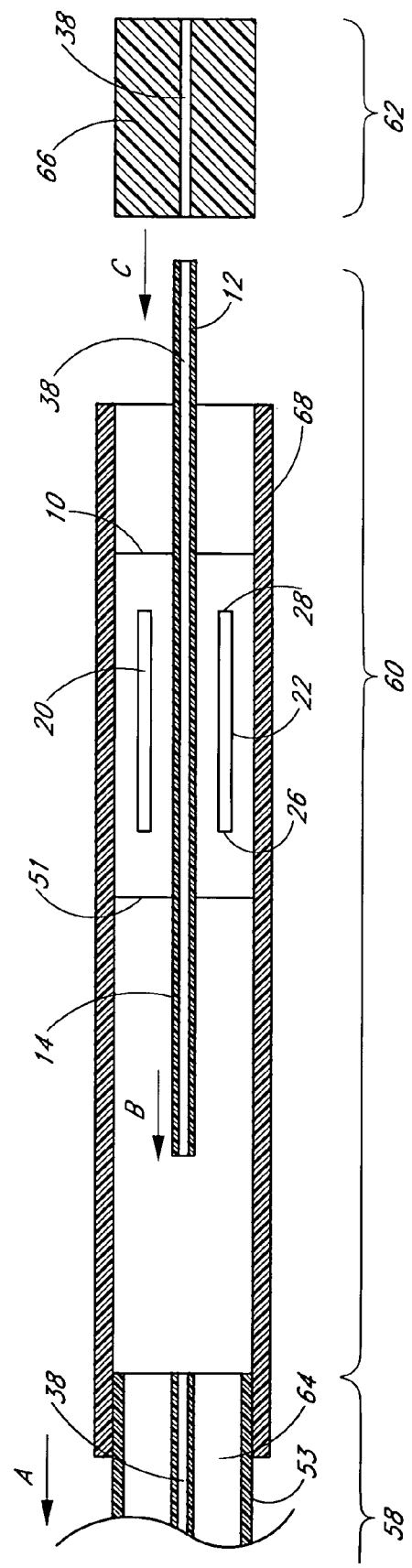
FIGS. 10A-10D illustrate a method for forming a catheter according to the present invention.

FIG. 10A-10D illustrate methods for forming a catheter according to the present invention. FIG. 10A illustrates a catheter sheath 68 positioned over an extension body 64 as illustrated by the arrow labeled A. The ultrasound assembly 10 is then positioned within the catheter sheath 68 as illustrated by the arrow labeled B. A terminal body 66 is then positioned within the catheter sheath 68 as indicated by the arrow labeled C.

Figure 10B:
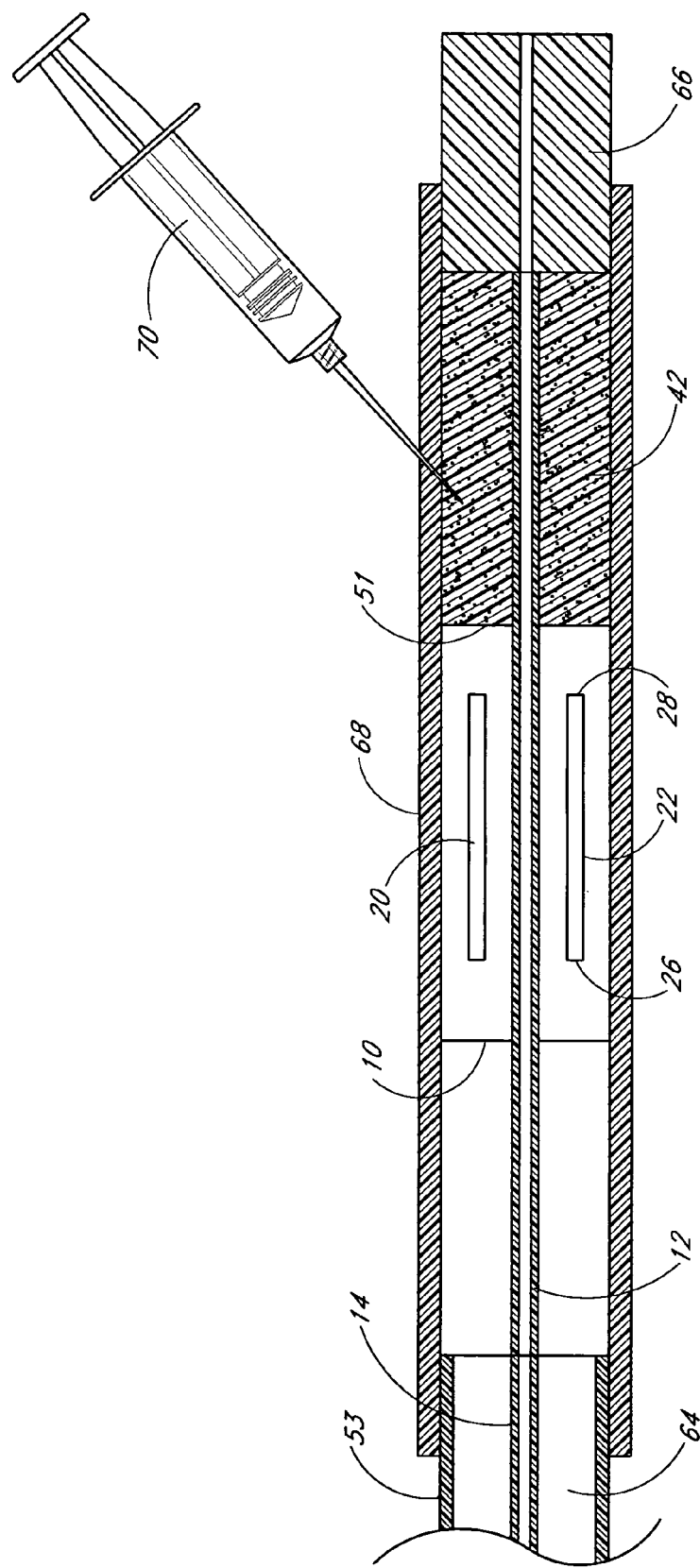

As illustrated in FIG. 10B, a binding medium 42 precursor is delivered adjacent to an end of the ultrasound transducer 20. Specifically, the binding medium 42 precursor is delivered into a volume between the ultrasound assembly 10 and the terminal body 66. FIG. 10B illustrates the binding medium 42 precursor delivered adjacent to an end of the ultrasound assembly 10 using an injection instrument such as a hypodermic needle 70. The binding medium 42 precursor can be sequentially delivered adjacent to one end of the ultrasound transducer 20 and then adjacent to the opposing end of the ultrasound transducer 20. The binding medium 42 precursor preferably solidifies to form a binding media adjacent to the ends of the ultrasound transducer 20.

Figure 10C:
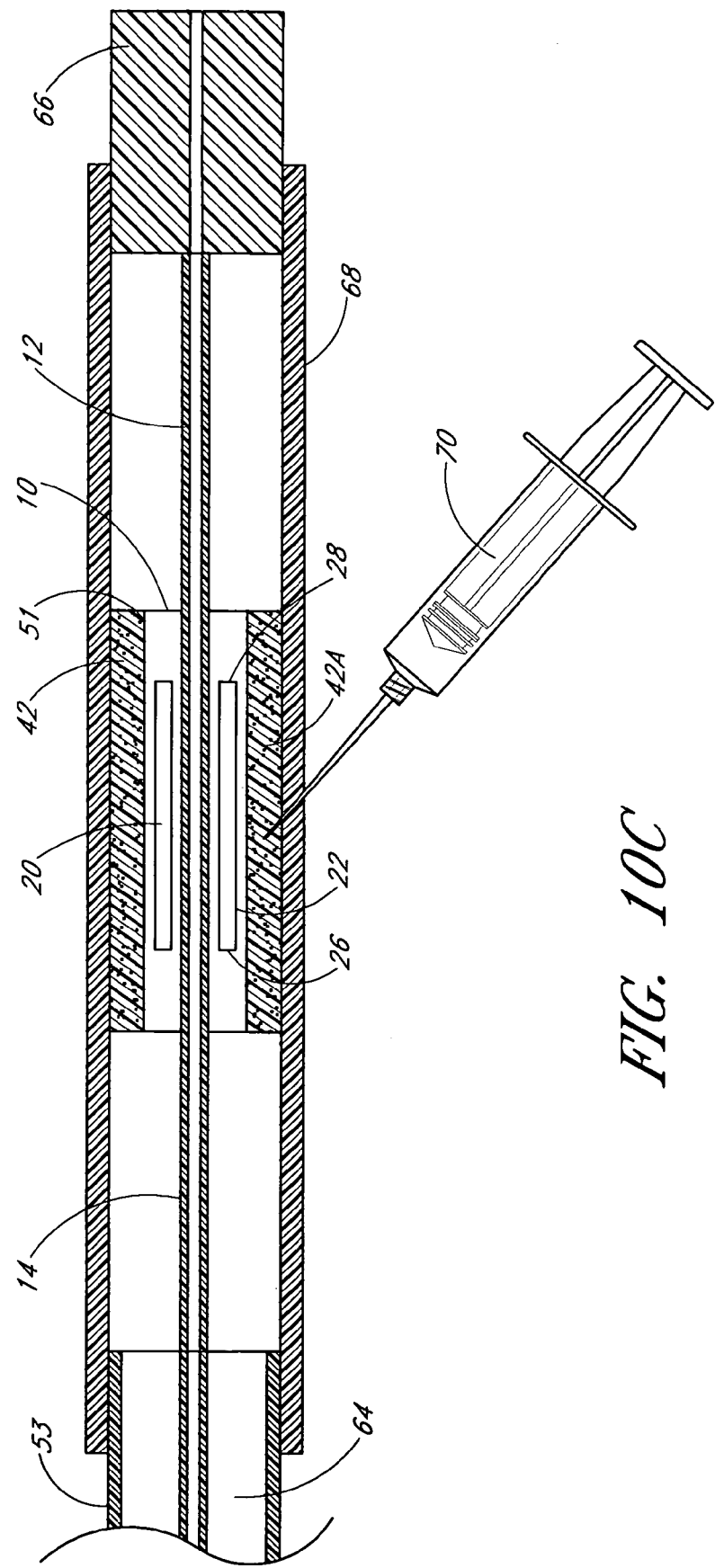

As illustrated in FIG. 10C, a binding medium 42 precursor can also be delivered into a volume between the external side 22 of the ultrasound transducer 20 and the external surface 53 of the catheter body 52. As illustrated, the quantity of binding medium 42 precursor delivered can be enough to fill the volume adjacent to the external side 22 of the ultrasound transducer 20. The binding medium 42 precursor preferably solidifies to form a binding medium 42 adjacent to the external side 22 of the ultrasound transducer 20. Alternatively, sufficient binding medium 42 precursor can be delivered to fill the volume adjacent to the ends of the ultrasound transducer 20.

Figure 10D:
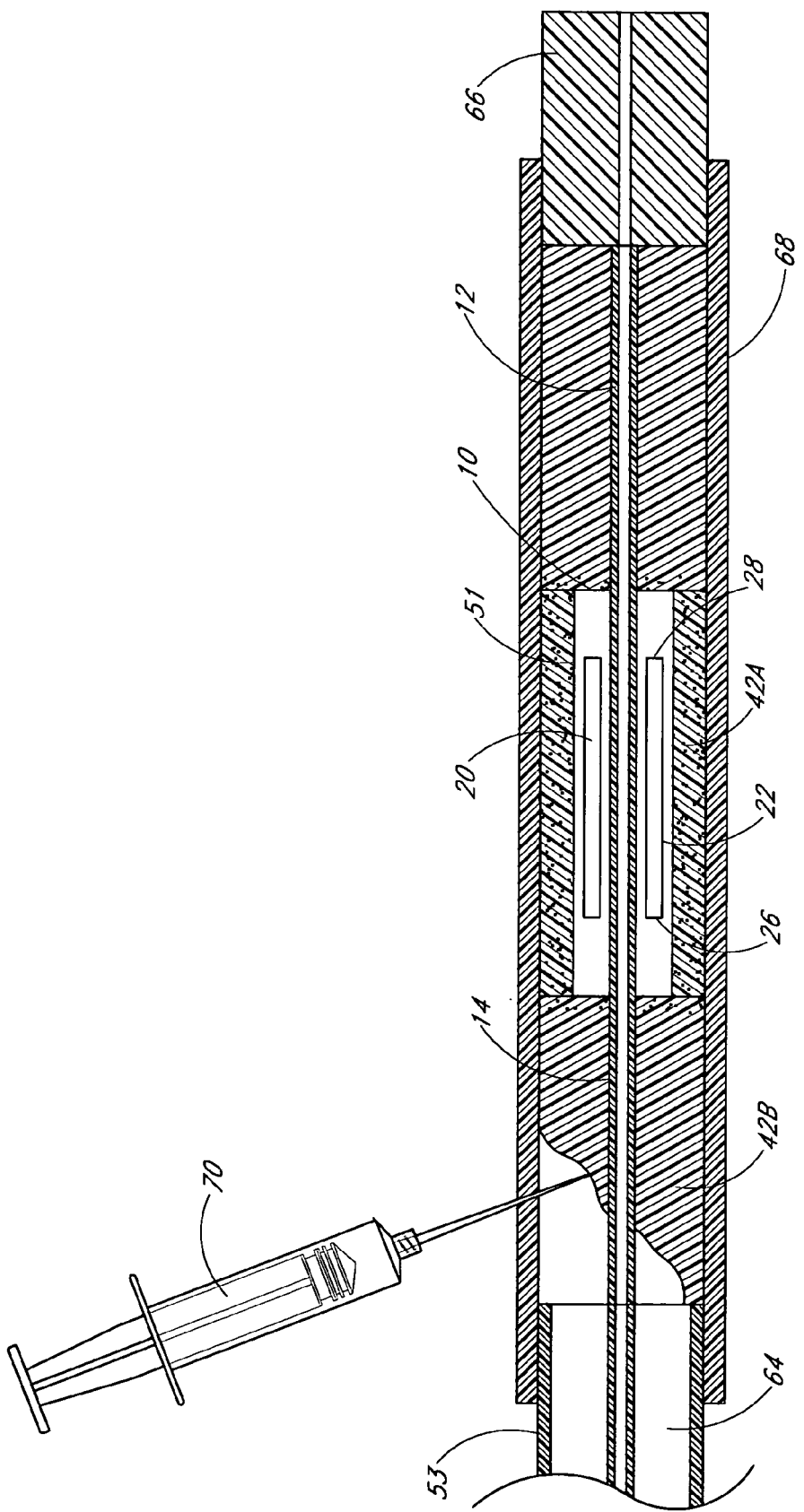

When the quantity of binding medium 42 precursor delivered fills the volume adjacent to the external side 22 of the ultrasound transducer 20, a second binding medium 42B precursor can be delivered into the volumes adjacent to the ends of the ultrasound transducer 20 as illustrated in FIG. 10D. The second binding medium 42B precursor preferably solidifies to form a second binding medium 42B adjacent to the ends of the ultrasound transducer 20.

Once the binding media delivered above have solidified, the catheter sheath 68 can be removed from the catheter body 52. Additionally, once a chamber 30 is formed, a fluid low acoustic impedance medium can be delivered into the chamber 30. A low acoustic impedance medium preferably has an acoustic impedance less than about 1.7 Megarayls, more preferably of about 0-0.7 Megarayls and most preferably from 0-0.4 Megarayls. As described above, suitable low acoustic impedance media include, but are not limited to, helium, argon, air and nitrogen. These media can be delivered into the chamber 30 during or after the media solidification process using an injection device such as a hypodermic needle 70. Similar techniques can be used to draw a vacuum within the chamber 30. Solid low acoustic impedance media such as silicones and rubbers can be positioned within the chamber 30 during the formation of the ultrasound assembly 10.

The methods for forming a catheter described with respect to FIG. 10A-10D can be used to form a catheter having multiple ultrasound assemblies 10. For instance, the elongated body 12 illustrated in FIG. 10A can be replaced with an elongated body 12 having a plurality of ultrasound assemblies 10. Alternatively, several independent elongated bodies 12 having ultrasound assemblies 10 can be sequentially positioned within the catheter sheath 68. The one or more lumens 38 in adjacent elongated bodies 12 are aligned before binding medium 42 precursor is delivered into the volume defined by the catheter sheath 68. Additional catheters having a plurality of ultrasound transducers are described in U.S. patent application Ser. No. 09/071,285, filed May 1, 1998 and entitled Ultrasound Catheter for Providing a Therapeutic Effect to a Vessel of a Body which is incorporated herein in its entirety.

When the ultrasound assembly 10 or catheter includes multiple ultrasound transducers 20, the methods for forming the ultrasound assembly 10 or catheter can include matching the resonant frequencies of the ultrasound transducers 20. For instance, the ultrasound transducers 20 can be selected such that any member of the plurality of ultrasound transducers 20 has a resonant frequency within about 10% of the resonant frequency of any other ultrasound transducer 20. More preferably, the ultrasound transducers 20 are selected such that any one has a resonant frequency within about 3%, even more preferably within about 1% and most preferably within about 0.5% of any other ultrasound transducer 20 in the plurality of ultrasound transducers 20. The selected ultrasound transducers 20 are then used to form an ultrasound assembly 10 or catheter.

The matching of the ultrasound transducers 20 allows the ultrasound transducers to be concurrently driven at a single frequency while reducing the inefficiencies associated with driving ultrasound transducers 20 at a frequency which is significantly different than their resonant frequency. Since the ultrasound transducers 20 can be driven at a single frequency, the matching the resonant frequencies of the ultrasound transducers 20 is preferred when the plurality of ultrasound transducers 20 are connected in parallel or in series.

The electrical connections for driving the one or more ultrasound transducers 20 can be done at various stages during the assembly of the catheter and/or ultrasound assembly 10. For instance, electrical wires can be coupled with the ultrasound transducers 20 before the ultrasound transducers 20 are positioned over the elongated body. Additionally, the electrical wires can be coupled with the ultrasound transducers 20 after the ultrasound transducers 20 are in position over the elongated body. Further, electrical connections can be made alternating with positioning the ultrasound transducers 20 over the elongated body.

Alternatively, one or more electrical wires can be positioned along the elongated body before the ultrasound transducers 20 are positioned over the elongated body. One or more ultrasound transducers 20 can then be slid over the elongated body such that the one or more electrical wires contact the inner side of the ultrasound transducers 20. The contact between the ultrasound transducers 20 and the electrical wire can serve as the electrical connection to the one or more ultrasound transducers 20. When a catheter or ultrasound assembly 10 includes more than one ultrasound transducer 20, the ultrasound transducers 20 can be connected in parallel, in series or independently connected. Wires extending from the one or more ultrasound transducers 20 can be threaded up through one or more lumens 38 in the extension body 64.

During the formation of the catheter and/or formation of the ultrasound assemblies 10, one or more sensors can be included in any of the media described above. The sensor can be positioned within a volume before a medium is delivered into the volume. Alternatively, the sensor can be delivered into a binding medium 42 precursor while the binding medium 42 precursor is in a flowable state. Wires extending from the one or more sensors can be threaded up through one or more lumens 38 in the extension body 64. Suitable sensors for use with the catheter include, but are not limited to, a temperature sensor. When a catheter includes one or more temperature sensors, the temperature sensor is preferably positioned adjacent to the external side 22 of an ultrasound transducer 20. Specifically, the one or more temperature sensors are preferably positioned in a volume between the external side 22 of the ultrasound transducer 20 and the external surface 53 of the catheter body 52.

The solidification of the binding medium 42 precursors can occur concurrently or independently of one another. As discussed with respect to FIGS. 5A-5F, the binding medium 42 precursor and the second binding medium 42B precursor preferably solidify to different degrees of hardness.

Binding medium 42 precursors for use with the catheters and ultrasound assemblies 10 discussed above are preferably flowable to optimize delivery into a desired volume. These precursors preferably solidify to a binding medium 42 having a reduced flowability. These precursors more preferably solidify to a binding medium 42 having a reduced flowability and an increased degree of adhesiveness. This solidification can occur through mechanisms including, but not limited to, cooling, setting and curing. Suitable binding media precursors and/or binding media include, but are not limited to, adhesives, epoxies, polymers, plastics, rubbers. Examples of suitable binding media with different degrees of hardness are EPOTEK 310 having a hardness of about 22 Shore D and HYSOL 3561 and 2939 having a hardness of about 85 Shore D. The binding media to be used can be selected for its particular hardness. Alternatively, binding media, such as epoxies, cure to a different hardness based on the component ratio in the binding media. The component ratio can be adjusted to achieve the desired hardness.

The binding media adjacent to the external side 22 of the ultrasound transducer 20 and/or adjacent to the ends of the ultrasound transducer 20 preferably has an acoustic impedance of about 1-20 Megarayls, more preferably about 1.3-10 Megarayls and most preferably about 4-8 Megarayls. As described above, the low acoustic impedance medium contained within the chambers preferably has an acoustic impedance less than about 1.7 Megarayls, more preferably of about 0-0.7 Megarayls and most preferably from 0-0.4 Megarayls. Further, the ratio of the acoustic impedances for the binding medium adjacent to the external side and/or adjacent ends the of the ultrasound transducer 20 measured relative to the acoustic impedance of the low acoustic impedance medium contained within the chambers is preferably at least 1.5:1, more preferably at least 2:1 and most preferably at least 4:1. Additionally the ratio is preferably 1.5:1 to 10,000:1, more preferably about 1.5:1 to 100:1 and most preferably 1.5:1 to 4:1.

Figure 11:
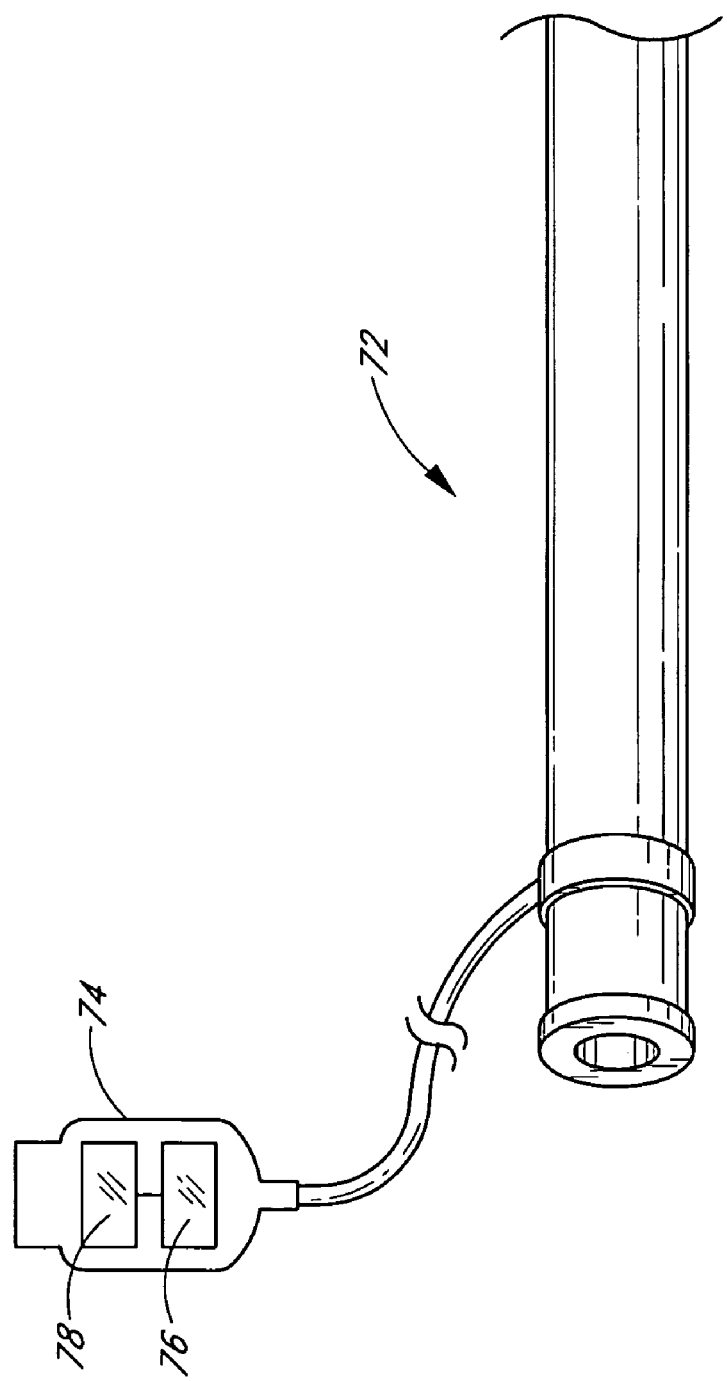
FIG. 11 illustrates the proximal portion of a catheter according to the present invention.

FIG. 11 illustrates the proximal portion 72 of a catheter according to the present invention. An electrical coupling 74 extends from the proximal portion 72 of the catheter. The electrical coupling 74 can be coupled with a catheter control system (not shown) for adjusting the frequency and power of ultrasound energy delivered from the catheter. These adjustments can be made in response to signals from one or more sensors included with the catheter. For instance, these adjustments can be made in response to signals form a temperature sensor in order to maintain the temperature at a treatment site within a particular range.

The electrical coupling 74 includes an autotransformer 76 for adjusting the characteristic impedance of the catheter to match the impedance of an amplifier included in the catheter control system. For instance, if the amplifier has an input impedance of 50 ohms and the catheter has a characteristic impedance of 40 ohms, the addition of the autotransformer can provide the catheter with a characteristic impedance of about 50 ohms. The matched impedance serves to increase the efficiency of the catheter system.

Because each catheter can have a different characteristic impedance, the windings on the autotransformer can be adjusted to match the particular catheter of interest. As a result, a method of assembling a catheter can include the step of providing an autotransformer which matches the characteristic impedance of the catheter to the characteristic impedance of a component in a catheter control system.

The electrical coupling also includes catheter identification electronics 78. The catheter identification electronics 78 indicate to the catheter control system what frequency the catheter should be driven. For instance, the catheter identification electronics 78 can be one or more resistors. The catheter control system can include logic for identifying the resistance. This resistance can be associated with a catheter of a particular frequency. The logic can identify the particular frequency of the catheter and can then cause the catheter to be driven at the indicated frequency. A computer chip is another example of suitable catheter identification electronics 78. The computer chip can produce signals indicating the frequency of the catheter to the catheter control system. In response, the catheter control system can drive the catheter at the appropriate frequency.

A catheter according to the present invention can be used by itself or can be used in conjunction with a sheath 82 as illustrated in FIGS. 12A-12D. Additional sheath and catheter embodiments are provided in U.S. patent application Ser. No. 09/107,078, filed Jun. 29, 1998 and entitled Sheath for Use with an Ultrasound Element which is incorporated herein in its entirety. FIG. 12A illustrates a sheath 82 configured to receive the catheter. The sheath 82 includes a sheath proximal end 84 and a sheath distal end 86. A catheter receiving lumen 88 extends through the sheath 82 and is sized to receive the catheter as illustrated in FIG. 12B. The sheath distal end 86 preferably includes an energy delivery portion which is constructed from a material which efficiently transmits ultrasound energy. Suitable materials for both the sheath 82 and the energy delivery section 90 include, but are not limited to, polyethylene.

The catheter can be rotated or moved within the sheath 82 as illustrated by the arrow labeled A. The movement of the catheter within the sheath 82 can be caused by manipulating the proximal portion of the catheter body 52 while holding the sheath proximal end 84 stationary. Although not illustrated, the sheath distal end 86 can include on or more temperature sensors.

As illustrated in FIGS. 12C-12D, the sheath 82 can also optionally include a drug delivery lumen 92. The drug delivery lumen 92 can include one or more drug delivery ports 94 through which a drug can be delivered. The drug delivery lumen 92 can be straight but is preferably curved and more preferably spirals around the catheter receiving lumen 88 as illustrated in FIGS. 12C and 12D. The drug delivery lumen 92 preferably has a diameter/width of about 0.0005"-0.005" and more preferably about 0.001"-0.003".

The drug delivery ports 94 are positioned close enough to achieve a substantially even flow of drug solution around the circumference of the sheath 82. The proximity of adjacent drug delivery ports 94 can be changed by changing the density of drug delivery ports 94 along the drug delivery lumen 92 or by changing the number of windings of the drug delivery lumen 92 around the energy delivery section 90. Suitable displacement between adjacent drug delivery ports 94 includes, but is not limited to, from 0.1" to 1.0", preferable 0.2" to 0.6".

The size of the drug delivery ports 94 can be the same or change along the length of the drug delivery lumen 92. For instance, the size of the drug delivery ports 94 distally positioned on the drug delivery section can be larger than the size of the drug delivery ports 94 which are proximally positioned on the drug delivery section. The increase in sizes of the drug delivery ports 94 can be designed to produce similar flowrates of drug solution through each drug delivery port 94. This similar flowrate increases the uniformity of drug solution flowrate along the length of the sheath 82. When the drug delivery ports 94 have similar sizes along the length of the drug delivery lumen 92, a suitable size for a drug delivery port includes, but is not limited to 0.0005" to 0.0050". When the size of the drug delivery ports 94 changes along the length of the drug delivery lumen 92, suitable sizes for proximally positioned drug delivery ports 94 includes, but is not limited to from 0.0001" to 0.005" and suitable sizes for distally positioned drug delivery ports 94 includes, but is not limited to, 0.0005" to 0.0020". The increase in size between adjacent drug delivery ports 94 can be substantially uniform between or along the drug delivery lumen 92. The dimensional increase of the drug delivery ports 94 is dependent upon material and diameter of the drug delivery lumen 92. The drug delivery ports 94 can be formed by burnt into the sheath 82 with a laser.

Uniformity of the drug solution flow along the length of the sheath 82 can also be increased by increasing the density of the drug delivery ports 94 toward the distal end of the drug delivery lumen 92.

The drug delivery ports 94 can optionally be closed slits in the sheath 82. The slits can have a straight or arcuate shape. When the dug delivery lumen 92 contains drug solution, the slits remain closed until the pressure within the drug delivery lumen 92 exceeds a threshold pressure. As the pressure within the drug delivery lumen 92 builds, the pressure on each of the slits will be approximately uniform. Once, the threshold pressure is reached, the uniform pressure will result in the slits opening almost simultaneously and cause a nearly uniform flow of drug solution out of all the slits. When the pressure within the drug delivery lumen 92 falls below the threshold pressure, the slits close and prevent delivery of additional drug solution. The stiffer the material used to construct the drug deliver lumen 38, the higher the threshold pressure required to open the slit shaped drug delivery ports 94. The slit shape can also prevent the drug delivery ports 94 from opening when exposed to low pressures from outside the sheath 82. As a result, slit shaped drug delivery ports 94 can maximize control of drug delivery.

Figure 13A:
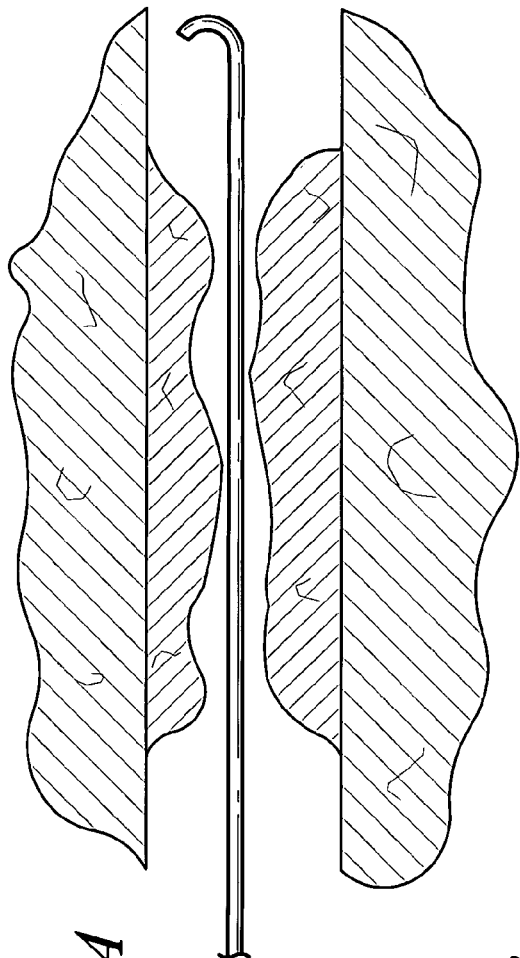

FIGS. 13A-13G illustrate a method for using the catheter with a sheath 82. In FIG. 13A, a guidewire is directed through vessels toward a treatment site which includes a clot. The guidewire is directed through the clot. Suitable vessels include, but are not limited to, cardiovascular vessels, the pancreas, sinuses, esophagus, rectum, gastrointestinal vessels and urological vessels.

Figure 13B:
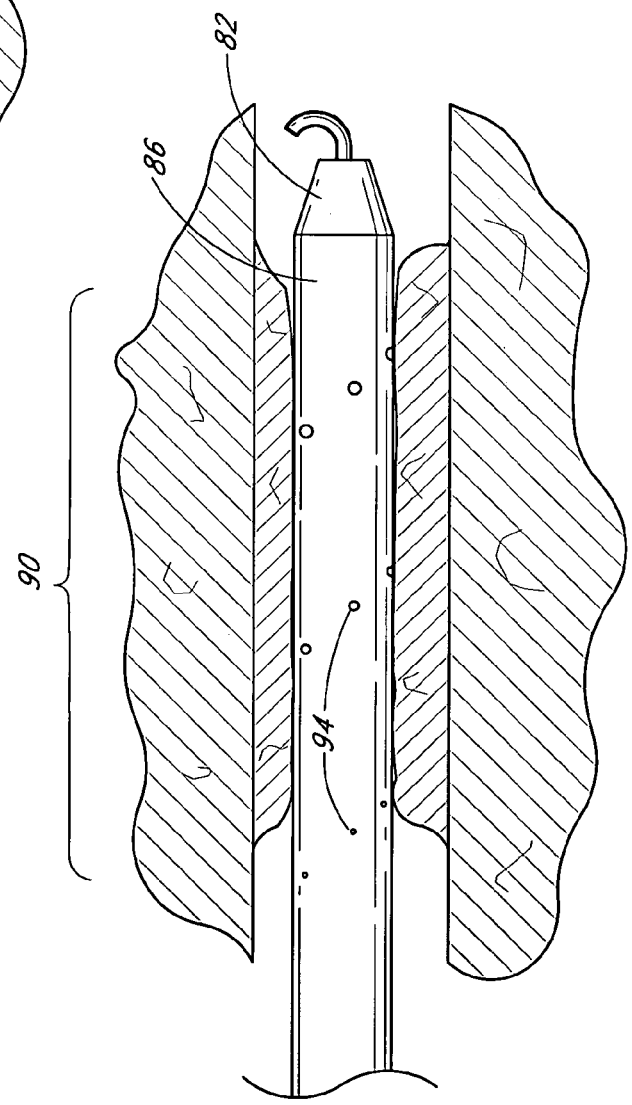

In FIG. 13B, the catheter receiving lumen 88 of the sheath 82 is slid over the guidewire and the sheath 82 is advanced along the guidewire using traditional over-the-guidewire techniques. The sheath 82 is advanced until the sheath distal end 86 is positioned at the clot. Radio opaque markers may be positioned at the sheath distal end 86 to aid in the positioning of the sheath 82 within the treatment site.

Figure 13C:
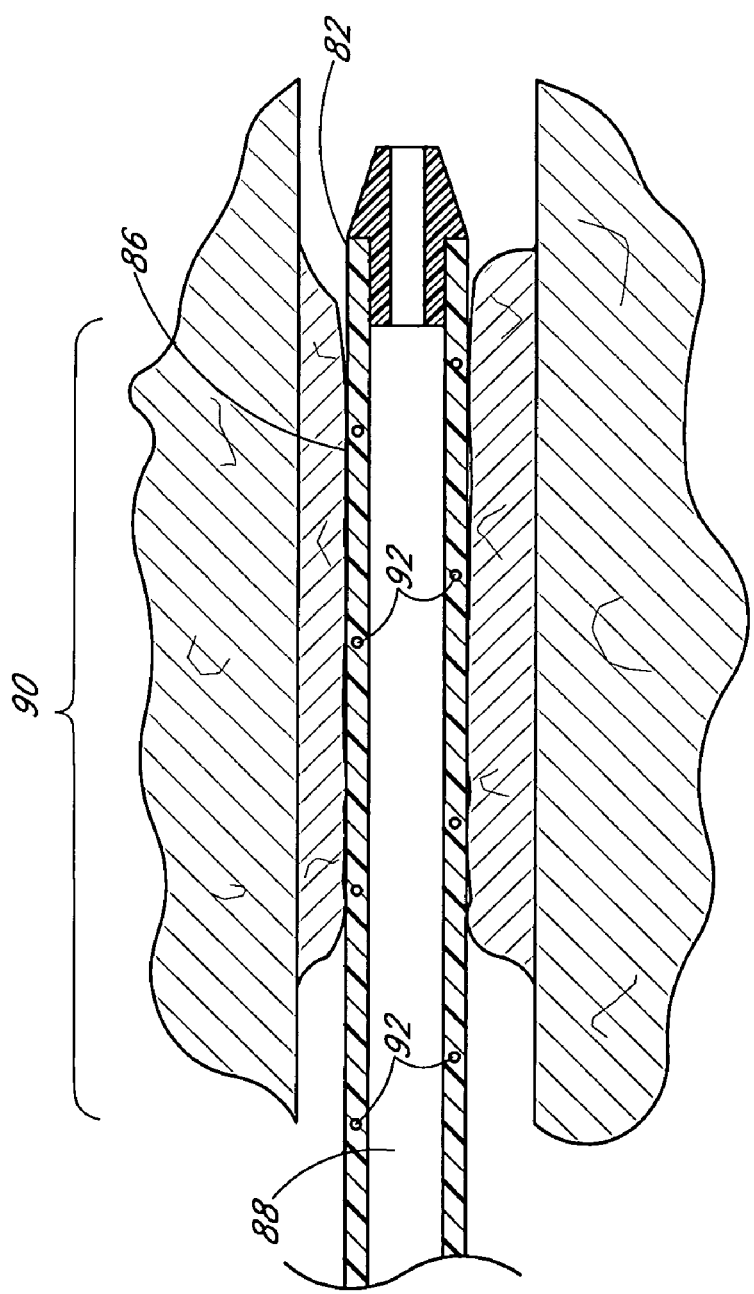
Figure 13D:
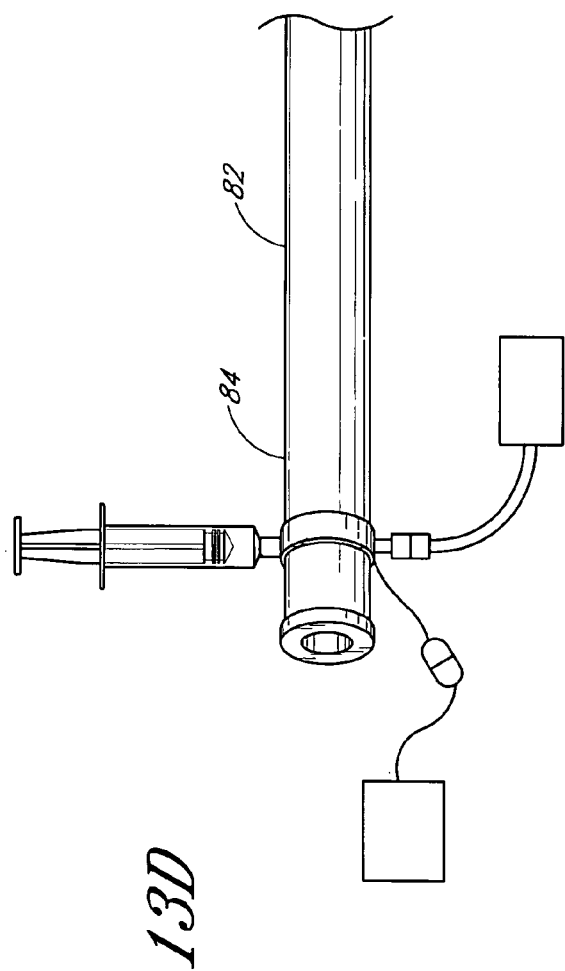
Figure 13E:
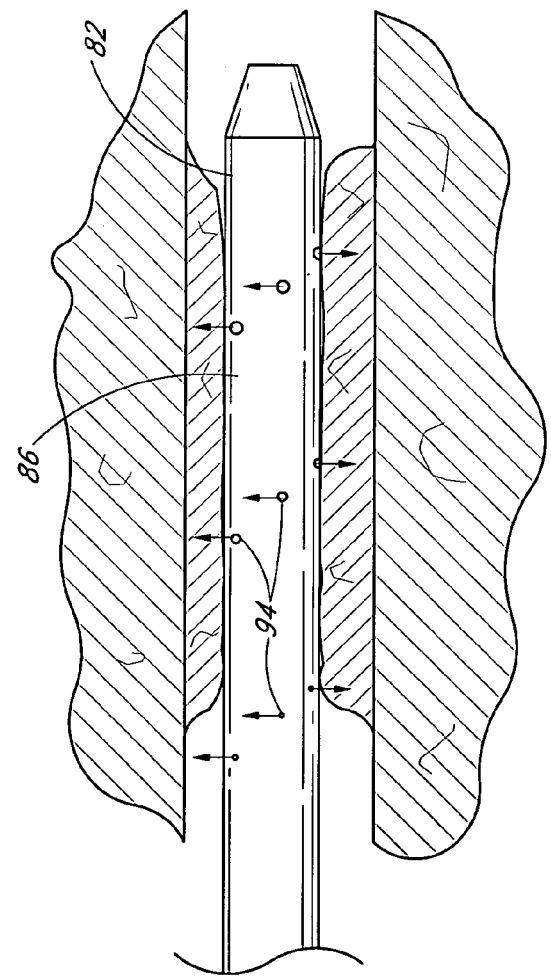

In FIG. 13C, the guidewire is withdrawn from the utility lumen 38 by pulling the guidewire proximally while holding the sheath 82 stationary. In FIG. 13D, a drug solution source is coupled with the drug inlet port. The drug solution source can be a syringe with a Luer fitting which is complementary with the drug inlet port. Pressure can be applied to a plunger on the drug solution source to drive the drug solution through the drug delivery lumen 92. The drug solution is delivered from the drug delivery lumen 92 through the drug delivery ports 94 as illustrated by the arrows in FIG. 13E. Suitable drug solutions include, but are not limited to, an aqueous solution containing Heparin, Uronkinase, Streptokinase, or tissue Plasminogen Activator (TPA).

In FIG. 13F, the catheter is inserted into the catheter receiving lumen 88 until the ultrasound assembly 10 is positioned at the sheath distal end 86. To aid in placement of the catheter within the sheath 82, radiopaque markers may be positioned on the catheter adjacent to each of the ultrasound transducers 20. Alternatively, the ultrasound transducers 20 themselves can be radiopaque. Once the catheter is properly positioned, the ultrasound transducer 20 is activated to deliver ultrasound energy through the sheath 82 to the treatment site. Suitable ultrasound energy is delivered with a frequency from 5 KHz to 100 MHz, more preferably from 10 KHz to 25 MHz and most preferably from 20 KHz to 5 MHz. While the ultrasound energy is being delivered, the ultrasound transducer 20 can be moved within the energy delivery section 90 as illustrated by the arrows labeled A. The movement of the ultrasound transducer 20 within the energy delivery section 90 can be caused by manipulating the body proximal section while holding the sheath proximal end 84 stationary.

While the present invention is disclosed by reference to the preferred embodiments and examples detailed above, it is to be understood that these examples are intended in an illustrative rather than limiting sense, as it is contemplated that modifications and combinations will readily occur to those skilled in the art, which modifications and combinations will be within the spirit of the invention and the scope of the appended claims.

What is claimed is:

1. A catheter system comprising:
a catheter body having an exterior surface and including
an ultrasound transducer having an external side between a first end and a second end,
a first binding medium adjacent to the first end of the ultrasound transducer, and
a second binding medium adjacent to the external side of the ultrasound transducer, the second medium being harder that the first medium.

2. The system of claim 1, wherein the first binding medium is more flexible than the second medium.

3. The system of claim 1 wherein a transducer sheath is positioned over the ultrasound transducer and the second binding medium occupies a volume between the transducer sheath and the external surface of the catheter body.

4. The catheter of claim 1 wherein an assembly sheath is positioned over the ultrasound transducer and the second binding medium occupies a volume between the ultrasound transducer and the assembly sheath.

5. The system of claim 1, wherein a catheter sheath defines at least a portion of the external surface of the catheter body and the second binding medium occupies a volume between the catheter sheath and the ultrasound transducer.

6. The system of claim 1, wherein:
the first binding medium is positioned between the second binding medium and the external surface of the catheter body.

7. The system of claim 1, wherein the catheter body includes a second ultrasound transducer having a side between a first end and a second end.

8. The system of claim 1, wherein the second binding medium is at least 3 times harder than the first binding medium.

9. The system of claim 1, wherein the second binding medium is about 4 to 5 times harder than the first binding medium.

10. The system of claim 1, wherein the first binding medium has a hardness of at least about 10 Shore D.

11. The system of claim 1, wherein the catheter body includes a second ultrasound transducer having a side between a first end and a second end.

12. The system of claim 11, wherein the first binding medium occupies a volume between the ultrasound transducer and the second ultrasound transducer.

13. The system of claim 12, wherein the second binding medium is positioned between the side of the second ultrasound transducer and the external surface of the catheter body.

14. The system of claim 1, wherein the ultrasound transducer is positioned over an elongated body.

15. The system of claim 14, wherein the catheter body includes a second elongated body coupled with the elongated body and the first binding medium occupies a volume between the ultrasound transducer and the second elongated body.

16. The system of claim 14, wherein the catheter body includes a terminal body coupled with the elongated body and the first binding medium occupies a volume between the ultrasound transducer and the terminal body.

17. The system of claim 1, wherein a lumen sized to receive a guidewire extends longitudinally through the catheter body.

18. A method of fabricating a catheter body, comprising:
providing an ultrasound transducer having a side between a first end and a second end;
positioning the ultrasound transducer over an elongated body having an external surface;
forming a first binding medium adjacent the first end of the ultrasound transducer; and
forming a second binding medium adjacent to the side of the ultrasound transducer, the second binding medium being more transmissive of ultrasound energy than the first binding medium.

19. The method of claim 18, wherein the first binding medium is more flexible than the second binding medium.

20. The method of claim 18, wherein delivering the second binding medium includes
positioning an assembly sheath over the ultrasound transducer, and
delivering the second binding medium into a volume between the ultrasound transducer and the assembly sheath.

21. The method of claim 20, wherein delivering the first binding medium includes
positioning a catheter sheath over the assembly sheath and delivering the first binding medium into a volume between the assembly sheath and the catheter sheath.

22. The method of claim 18, wherein delivering the second binding medium includes
positioning a transducer sheath over the ultrasound transducer,
positioning an assembly sheath over the transducer sheath, and
delivering the second binding medium into a volume between the transducer sheath and the external surface of the catheter body.

23. The method of claim 18, wherein delivering the second binding medium includes
positioning a catheter sheath over the ultrasound transducer, and
delivering the second binding medium into a volume between the ultrasound transducer and the catheter sheath.

24. The method of claim 18, wherein delivering the first binding medium includes
delivering the first binding medium into a volume between the external surface of the elongated body and the catheter sheath.

25. The method of claim 18, wherein the second binding medium is harder than the first binding medium.

26. The method of claim 18, wherein the second binding medium is at least 3 times harder than the first binding medium.

27. The method of claim 18, wherein the second binding medium is about 3 to 5 times harder than the first binding medium.

28. The method of claim 18, wherein the first binding medium has a hardness of at least about 10 Shore D.

29. The method of claim 18, wherein the first binding medium has a hardness of about 20 to 40 Shore D.

30. The method of claim 29, further comprising:
forming the second binding medium adjacent to the side of the second ultrasound transducer.

31. The method of claim 18, wherein the second binding medium has a hardness of at least 65 shore D.

32. The method of claim 18, wherein the second binding medium has a hardness from about 65 to about 120 Shore D.

33. The method of claim 18, wherein the first binding medium has a hardness of at least 10 and the second binding medium has a hardness of at least 65 Shore D.

34. The method of claim 18, wherein the first binding medium has a hardness from about 20 to about 40 Shore D and the second binding medium has a hardness from about 80 to about 100 Shore D.

35. The method of claim 18, further comprising:
positioning a second ultrasound transducer over the elongated body, the second ultrasound transducer having a side between a first end and a second end.

36. The method of claim 35 wherein forming the first binding medium includes delivering the first binding medium into a volume between the ultrasound transducer and the second ultrasound transducer.

37. The method of claim 18, further comprising:
coupling the elongated body with a second elongated body.

38. The method of claim 37, wherein coupling the elongated body with a second elongated body includes aligning a lumen within the elongated body with a lumen within the second elongated body.

39. The method of claim 37, wherein forming the first binding medium includes
delivering the first binding medium into a volume between the ultrasound transducer and the second elongated body.

40. The method of claim 18, further comprising:
coupling the elongated body with a terminal body.

41. The method of claim 40, wherein forming the first binding medium includes delivering the first binding medium into a volume between the ultrasound transducer and the terminal body.

42. The method of claim 40, wherein coupling the elongated body with a terminal body includes aligning a lumen within the elongated body with a lumen within the terminal body.

43. A catheter system comprising:
a catheter body having an exterior surface and including
an ultrasound transducer having an external side between a first end and a second end,
a first binding medium adjacent to the first end of the ultrasound transducer and having a hardness of at least about 10 Shore D, and
a second binding medium adjacent to the external side of the ultrasound transducer, the second medium being harder that the first binding medium.

* * * * *